(12) United States Patent
Coulombe et al.

(10) Patent No.: US 12,243,166 B2
(45) Date of Patent: Mar. 4, 2025

(54) SYSTEM AND METHOD FOR AUGMENTED INTELLIGENCE IN DENTAL PATTERN RECOGNITION

(71) Applicant: AICAD Dental Inc., Chelsea (CA)

(72) Inventors: Fabien Coulombe, Chelsea (CA); Akshaykumar Ketankumar Patel, Ottawa (CA)

(*) Notice: Subject to any disclaimer, the term of this patent is extended or adjusted under 35 U.S.C. 154(b) by 273 days.

(21) Appl. No.: 17/821,320

(22) Filed: Aug. 22, 2022

(65) Prior Publication Data

US 2023/0066220 A1 Mar. 2, 2023

Related U.S. Application Data

(60) Provisional application No. 63/256,790, filed on Oct. 18, 2021, provisional application No. 63/251,886, filed on Oct. 4, 2021, provisional application No. 63/243,866, filed on Sep. 14, 2021, provisional application No. 63/236,932, filed on Aug. 25, 2021.

(51) Int. Cl.
*G06T 17/20* (2006.01)
(52) U.S. Cl.
CPC .......... *G06T 17/20* (2013.01); *G06T 2210/41* (2013.01)
(58) Field of Classification Search
CPC ... G06T 17/20; G06T 15/06; G06T 2219/008; G06T 19/00; G06T 2210/41; G06V 2201/03; G06V 10/82; G06V 20/64
See application file for complete search history.

(56) References Cited

U.S. PATENT DOCUMENTS

| | | | |
|---|---|---|---|
| 8,496,474 B2 | 7/2013 | Chishti et al. | |
| 9,358,082 B2 | 6/2016 | Nilsson | |
| 10,076,389 B2 | 9/2018 | Wu et al. | |
| 10,149,744 B2 * | 12/2018 | Lior ....................... | A61C 13/34 |
| 10,206,757 B2 | 2/2019 | Pettersson | |
| 10,426,578 B2 | 10/2019 | Rubbert et al. | |
| 10,548,668 B2 | 2/2020 | Furrer et al. | |
| 10,568,722 B2 | 2/2020 | Kopelman et al. | |
| 10,959,815 B2 | 3/2021 | Chou | |
| 10,980,621 B2 | 4/2021 | Lancelle et al. | |
| 11,051,912 B2 | 7/2021 | Martz et al. | |
| 11,152,106 B2 | 10/2021 | Kopelman et al. | |
| 11,191,618 B1 | 12/2021 | Raslambekov | |
| 11,351,014 B2 | 6/2022 | Hasan et al. | |
| 2020/0405464 A1 | 12/2020 | Nikolskiy et al. | |
| 2021/0174604 A1 | 6/2021 | Long et al. | |

(Continued)

FOREIGN PATENT DOCUMENTS

WO 2021240290 A1 12/2021

*Primary Examiner* — Said Broome
*Assistant Examiner* — Donna J. Ricks

(57) ABSTRACT

A system and method for dental image file capture and manipulation for the purpose of dental, orthodontic, and periodontic tracking, diagnostics, and dental prosthetic and implant design. Augmented intelligence in dental file segmentation using descriptor matrixes with a common centroid or reference locus as a reference point describing related dental surface structures reduces the data size of dental image files such that dental images can be manipulated and compared to other dental files and can be used in machine learning and matching systems. This expedites the design and manufacture of dental prosthetics, appliances, and in dental monitoring and treatment.

21 Claims, 43 Drawing Sheets

(56) References Cited

U.S. PATENT DOCUMENTS

| | | |
|---|---|---|
| 2021/0321872 A1 | 10/2021 | Saphier et al. |
| 2022/0008175 A1 | 1/2022 | Öjelund et al. |
| 2022/0218452 A1* | 7/2022 | Gandrud ................. A61C 5/80 |
| 2022/0351829 A1* | 11/2022 | Xia ........................ G16H 50/50 |
| 2023/0149135 A1* | 5/2023 | Lipnik ................. A61C 9/0053 433/214 |

* cited by examiner

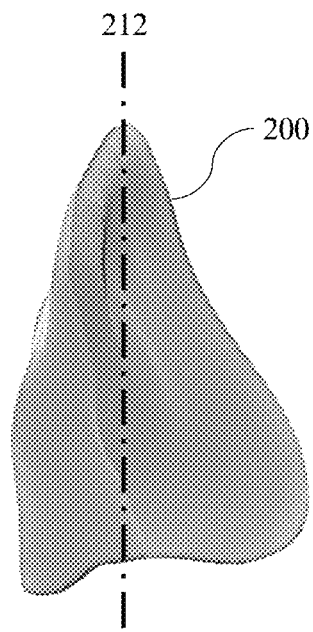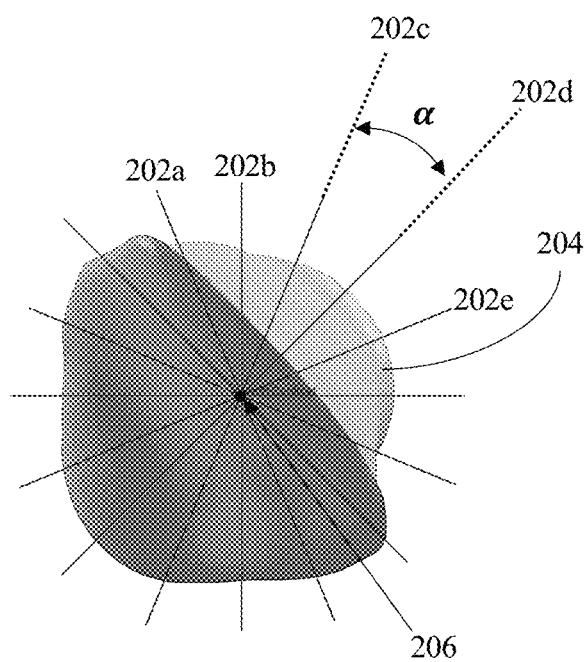
FIG. 6A  FIG. 6B
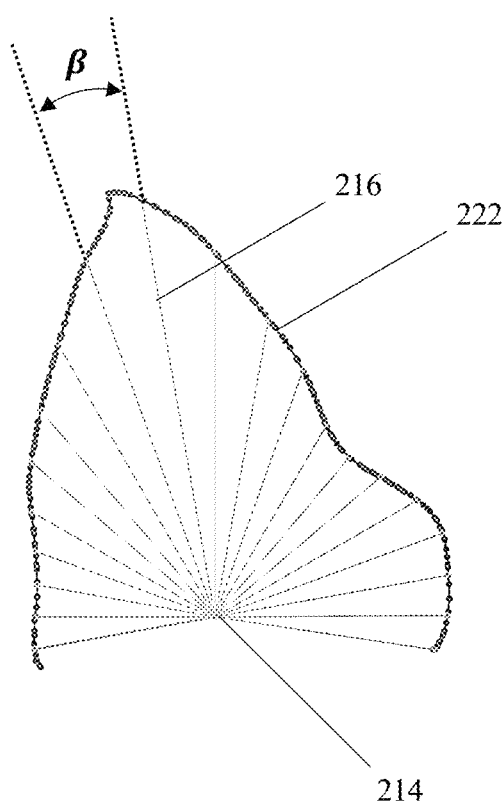
FIG. 6C

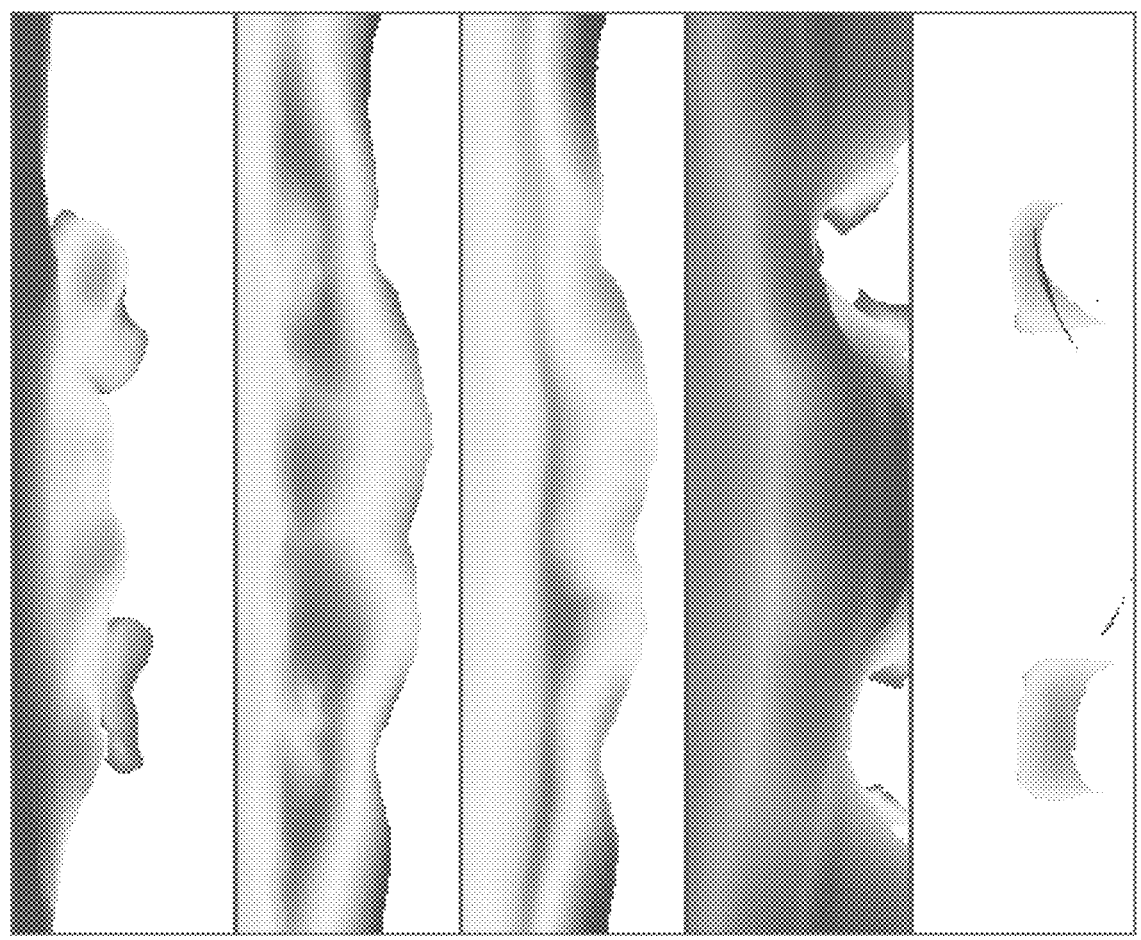
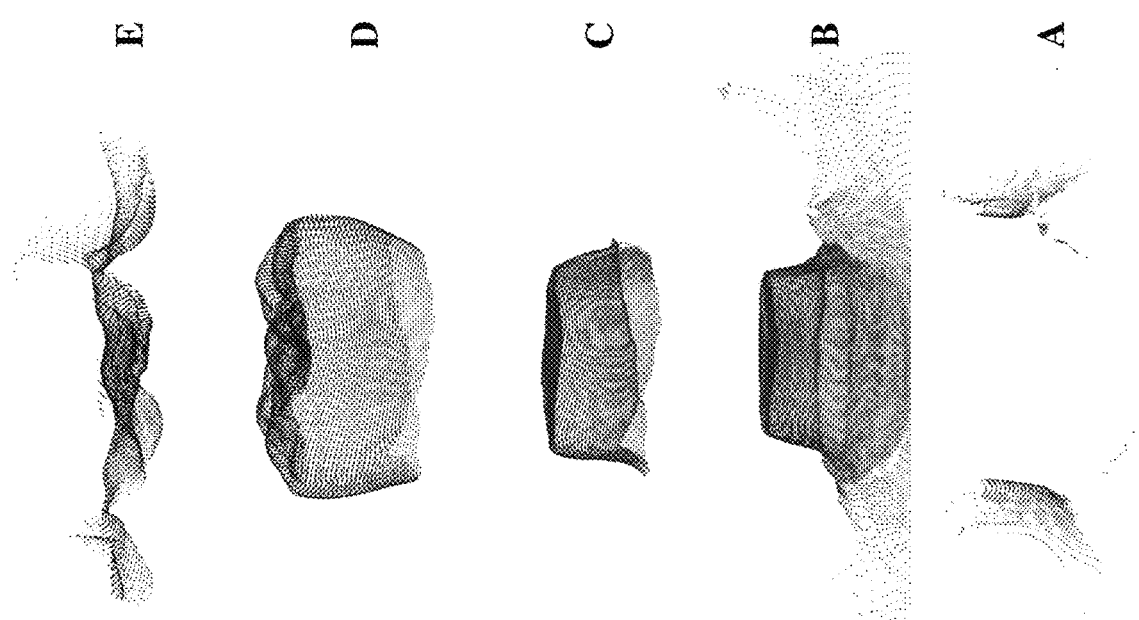
FIG. 9

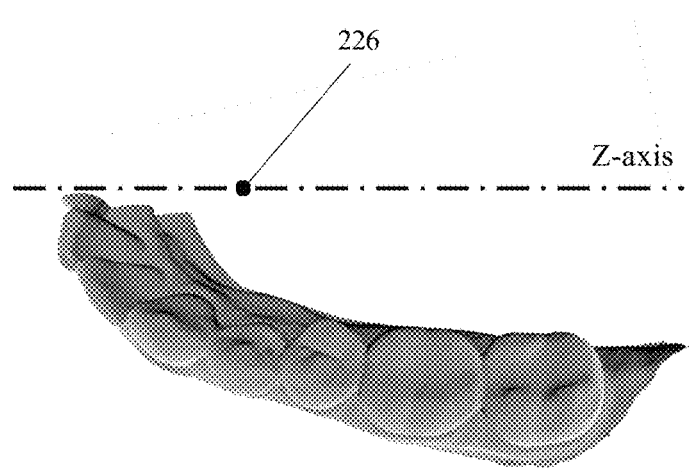
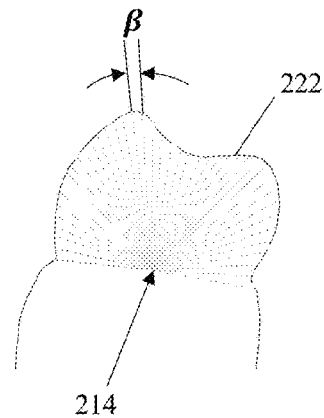
FIG. 18A  FIG. 18C
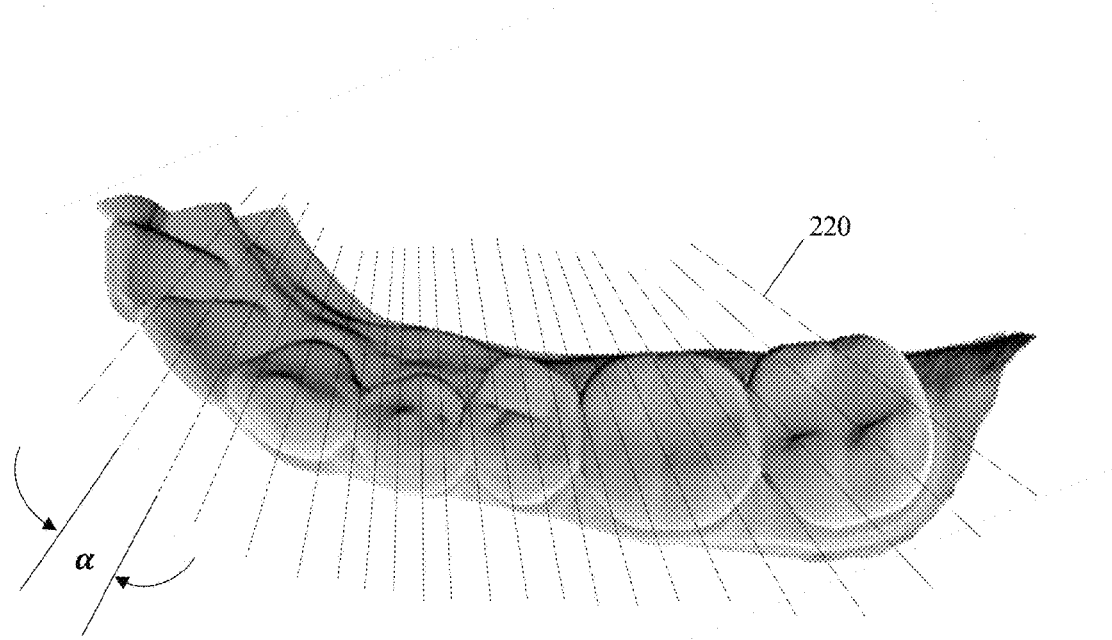
FIG. 18B

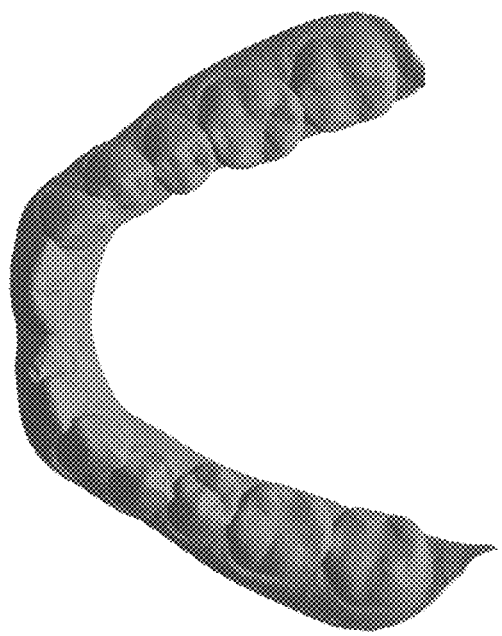
FIG. 20A
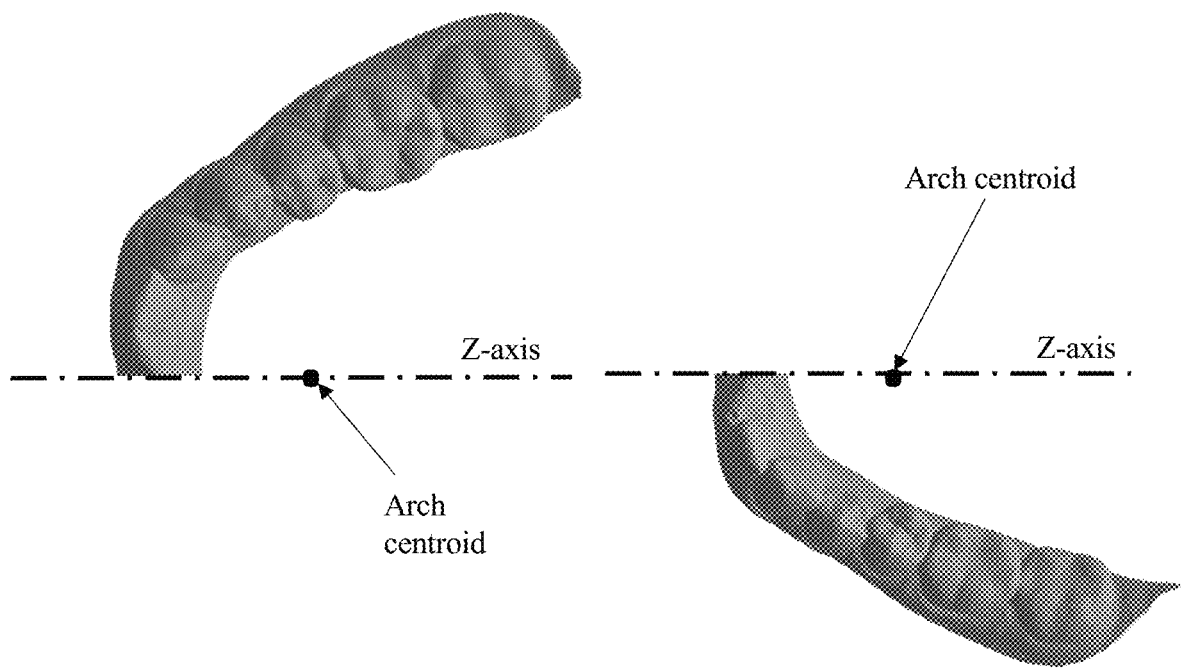
FIG. 20B  FIG. 20C

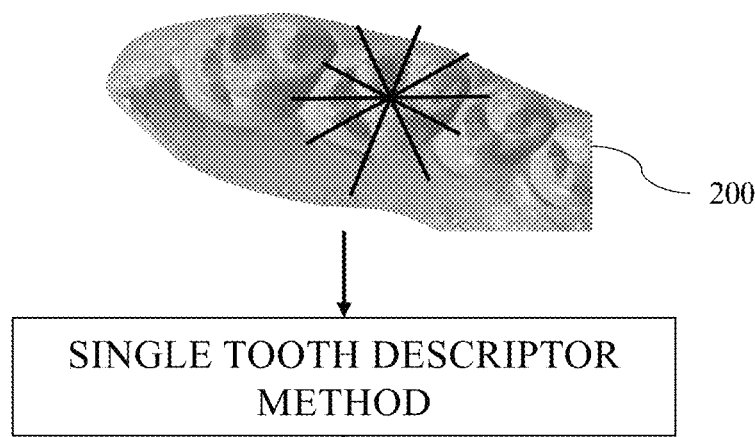
SINGLE TOOTH DESCRIPTOR METHOD
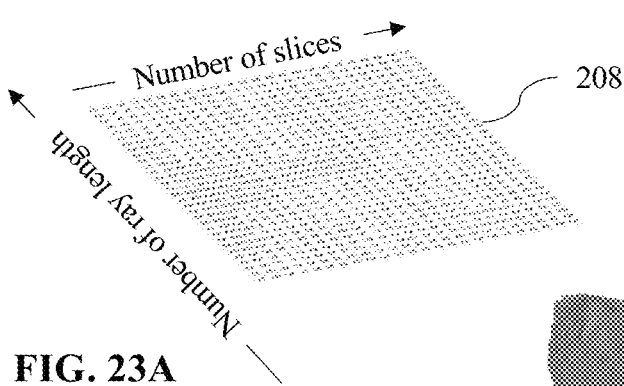
FIG. 23A
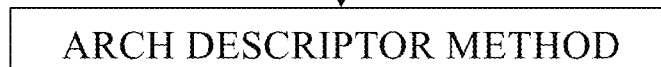
ARCH DESCRIPTOR METHOD
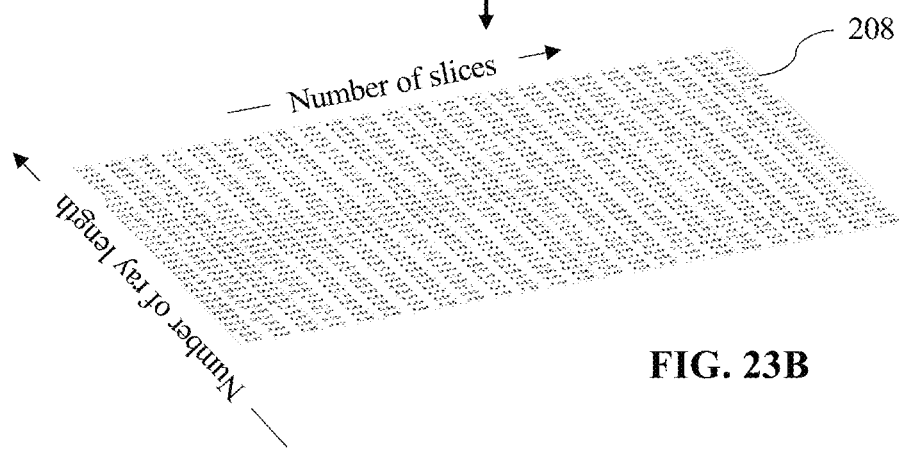
FIG. 23B

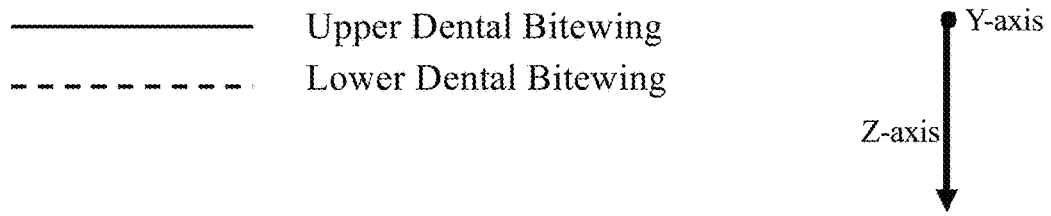
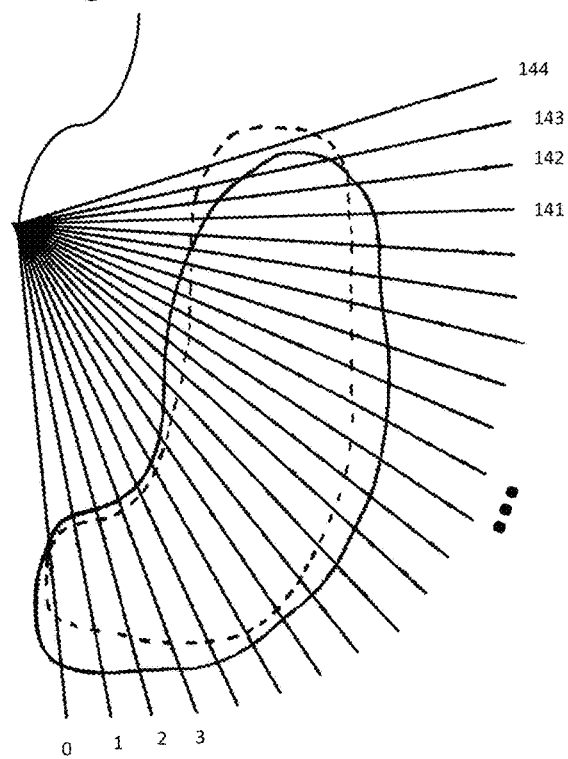
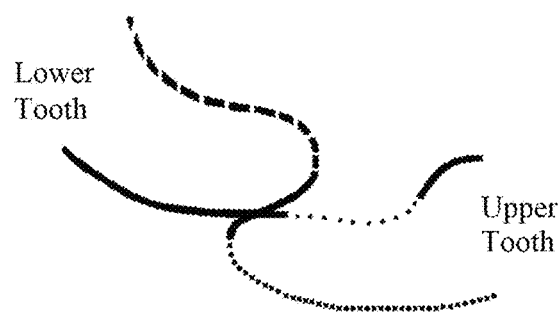
FIG. 29A                  FIG. 29B

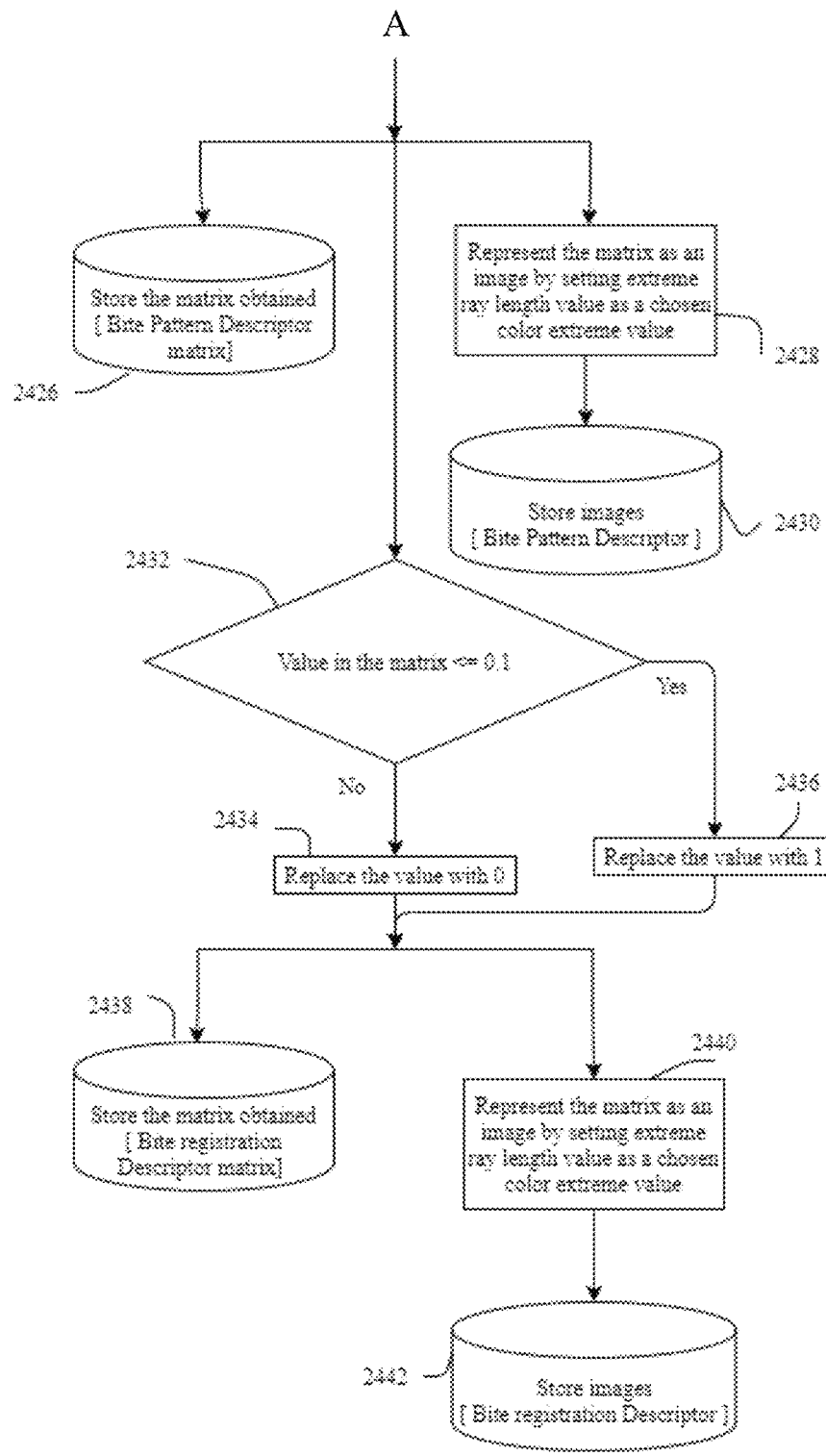
FIG. 30 ctd.

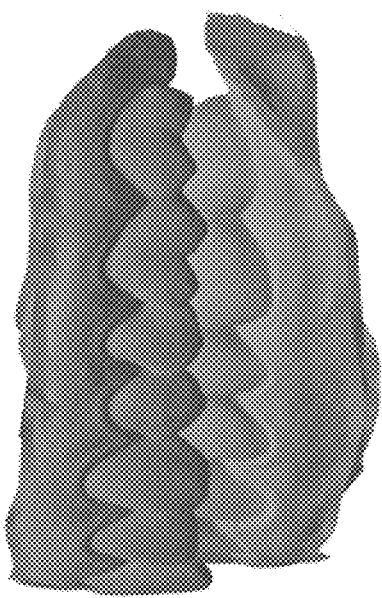
FIG. 32A
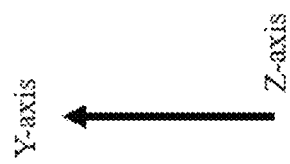
FIG. 32B
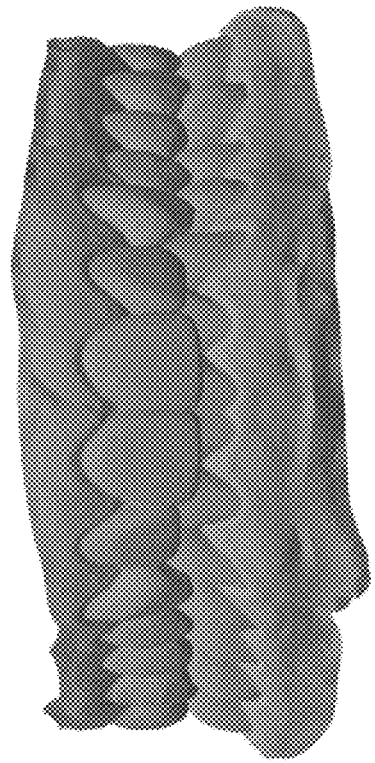
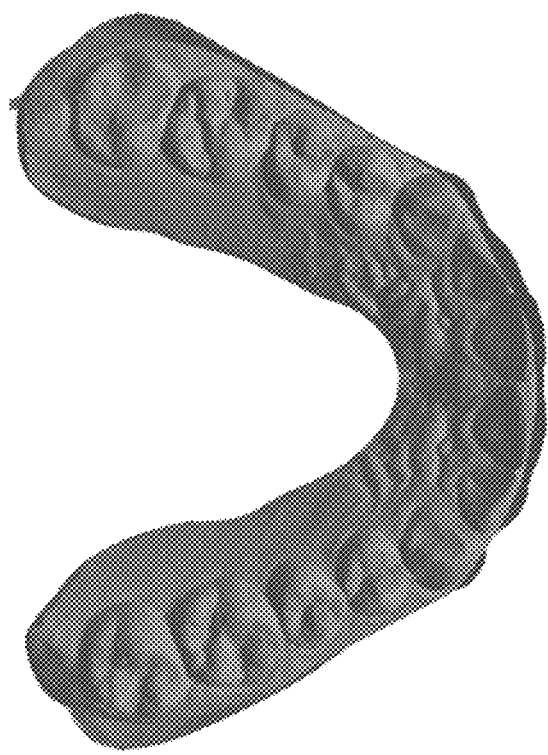
FIG. 32C

FIG. 33A
FIG. 33B
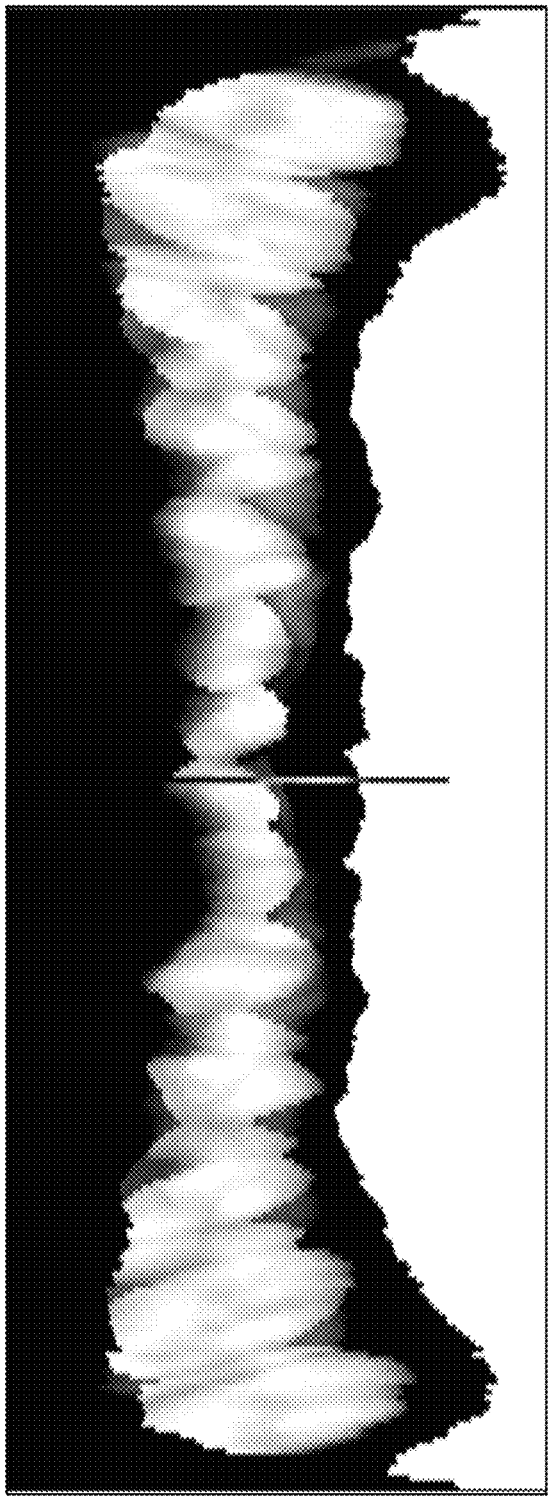
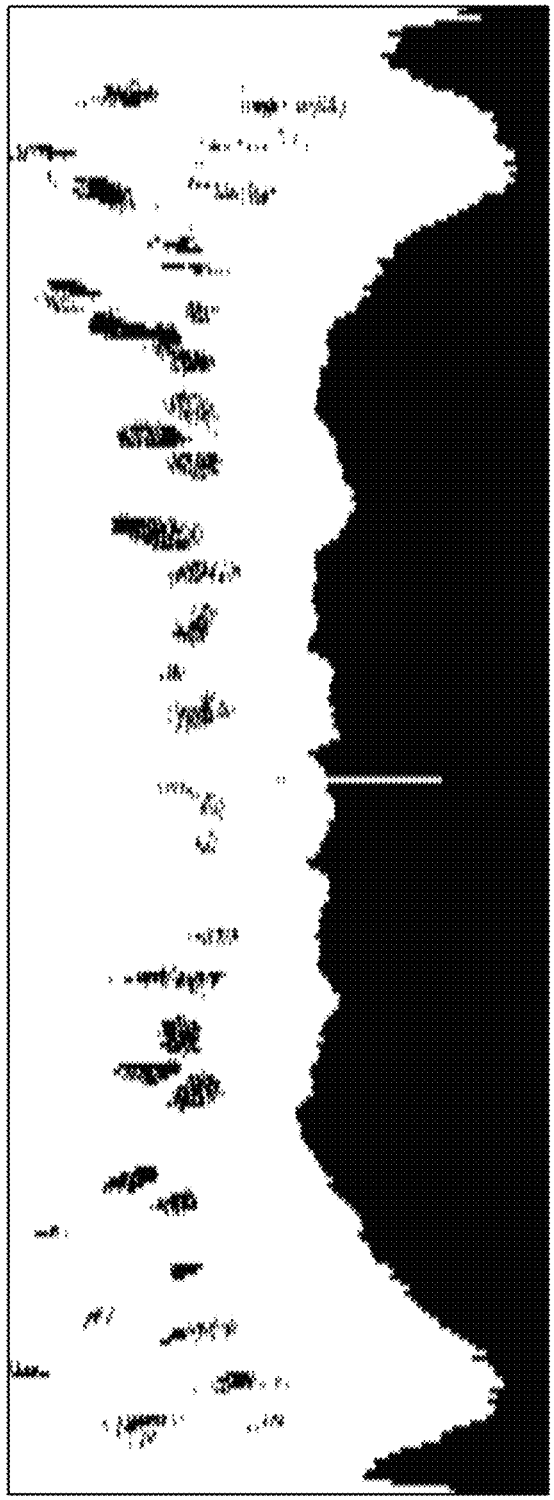

SYSTEM AND METHOD FOR AUGMENTED INTELLIGENCE IN DENTAL PATTERN RECOGNITION

CROSS-REFERENCE TO RELATED APPLICATIONS

This application claims priority to United States provisional patent applications U.S. 63/236,932 filed on 25 Aug. 2021, U.S. 63/243,866 filed on 14 Sep. 2021, U.S. 63/251,886 filed on 4 Oct. 2021, and U.S. 63/256,790 filed on 18 Oct. 2021, all of which are hereby incorporated by reference herein in their entirety.

FIELD OF THE INVENTION

The present disclosure generally relates to dental imaging technology, and in particular to a system and method for augmented intelligence in dental pattern recognition using specially formatted stacked data arrays.

BACKGROUND

Dental imaging technologies are used in a modern dental practice to image the mouth and teeth, as well as the underlying bone and jaw structure. Dental imaging can provide a wide range of information for improving the care of patients, including for monitoring tooth movement, gum changes, for designing dental implants and prosthetics, and for investigations prior to surgery. In orthodontics dental imaging is used to plan treatments for alignment of teeth, including designing and creating dental appliances, such as orthodontic aligners, to align the patient's teeth according to the treatment plan.

In the design of dental prosthetics and implants, for example, there are a variety of imaging technologies and associated dental computer aided design (CAD) software technologies that are used to provide 2D as well as 3D images of the teeth, gums, and mouth to enable a technician to design and build an implant that fits the patient. Imaging is generally done using one or more optical cameras, or using x-rays such as with computed tomography (CT) or radiography. By combining multiple 2D images or cross sectional images a 3D image of the mouth or teeth area can be constructed as a mosaic of 2D images. A dental implant or prosthetic can be designed based on this captured 3D image of the mouth.

In an example, U.S. Pat. No. 10,426,578 B2 to Rubbert et al. describes a dental implant system for a dental prosthesis/implant which includes a dental implant body having a prosthesis interface formed to receive an occlusal-facing dental prosthesis component. The prosthesis interface has a custom three-dimensional surface shape positioned and formed to create a form locking fit with respect to the occlusal-facing dental prosthesis component when positioned thereon.

A 3D image captured of the teeth and gums can be further converted by shaping 3D images in various tessellated data points format, also referred to as meshing, to create a stereolithography or "STL" format of the 3D image, and these mesh files can be used in dental computer-aided design (CAD) technologies by manipulating these three-dimensional (3D) images. In one example, U.S. Pat. No. 11,191,618 B1 to Raslambekov describes a method and a system for manufacturing an orthodontic appliance by receiving a 3D mesh including a plurality of inner vertices representative of an inner surface of an appliance, generating a plurality of outer vertices representative of an outer surface of the appliance, and causing the manufacturing of the appliance based on the appliance 3D representation. However, processing mesh or STL data is central processing unit (CPU) intensive and native file formats are very large.

In current digital workflows, computer-aided design for orthodontic, prosthetic, periodontic, and other dental modeling, is extremely labor-intensive step and often the most time-consuming and expensive step in the dental prosthetic manufacturing process. In contrast, computer-Aided Manufacturing (CAM) of dental frameworks using 3D printers and computer numeric control (CNC) is comparably faster than CAD, requires little skill labor, and the material used for prosthetics manufacturing is quickly getting less expensive. Therefore, CAD is a bottleneck for current dental CAD-CAM workflows.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

It is an object of the invention to provide a system and method for dental image file capture and manipulation for the purpose of dental, orthodontic, and periodontic tracking, diagnostics, and dental prosthetic and implant design. Augmented intelligence in dental file segmentation using descriptor matrixes with a common centroid or reference locus as a reference point describing and anchoring in space related dental surface structures reduces the data size of dental image files such that dental images can be manipulated and compared to other dental files and can be used in machine learning and matching systems. This expedites the design and manufacture of dental prosthetics, appliances, and in dental monitoring and treatment, and reduces the expenditure of data, processing time, and therefore cost of manufacturing dental prosthetics.

In an aspect there is provided a computer-implemented method for dental object description comprising: receiving, by a processor, a three dimensional (3D) mesh file representation of a dental object comprising a plurality of related surfaces; extending a plurality of indexing rays from a reference locus through the 3D mesh file such that the indexing ray intersects with the plurality of related surfaces at a surface boundary; creating a 2D descriptor matrix for each surface of the plurality of related surfaces by: for each of the plurality of indexing rays, measuring a length from the reference locus to the surface boundary to generate a plurality of indexing ray lengths; and storing the plurality of indexing ray lengths in a 2D matrix to create the 2D descriptor matrix of the surface; and storing the 2D descriptor matrix for each surface of the plurality of related surfaces as a matrix descriptor stack, wherein the cell of each row and column in each 2D descriptor matrix of the plurality of related surfaces corresponds with the same indexing ray such that the 2D descriptor matrix for each of the plurality of related surfaces is stacked in space.

In an embodiment, the method further comprises slicing the 3D mesh file into an plurality of two dimensional (2D) cross-sectional slicing planes, wherein the plurality of indexing rays are coplanar with a cross-sectional slicing plane.

In another embodiment, the slicing planes are parallel to the reference locus or extend radially from the reference locus.

In another embodiment, the reference locus is a common centroid or a common z-axis.

In another embodiment, the method further comprises training a convolutional autoencoder model using a convolutional neural network to identify matching 2D descriptor matrixes in a descriptor database.

In another embodiment, the method further comprises assigning a dental object type to each 2D descriptor matrix and matching the 2D descriptor matrix to a matched 2D descriptor matrix describing a matching dental object having the same dental object type.

In another embodiment, the related surfaces are one or more of gumline, gum surface, neighbouring tooth surface, occlusal tooth surface on an opposite jaw to the dental object, arch surface, inside prosthetic surface, post surface, outside prosthetic surface, and appliance surface.

In another embodiment, the reference locus is a common centroid or a reference axis.

In another embodiment, the dental object comprises one or more of a tooth, a plurality of teeth, a bitewing, a gumline, and a dental arch.

In another embodiment, the method further comprises applying a visualization scheme to visualize each 2D descriptor matrix.

In another embodiment, the method further comprises the matrix descriptor stack is used in dental tracking, orthodontic tracking, periodontic tracking, oral diagnostics, dental prosthetic design, orthodontic device design, dental implant design, or surgery planning.

In another embodiment, the dental object is a group of adjacent teeth described by a group descriptor matrix, and wherein the matrix descriptor stack comprises a tooth submatrix for each tooth in the group of adjacent teeth, each submatrix comprising the same dimensions as the group descriptor matrix and zero or null entries for the other teeth in the group of teeth.

In another embodiment, the method further comprises creating a visualization map for the overall group descriptor submatrix and for each tooth submatrix.

In another embodiment, the dental object is a an upper subset of adjacent teeth and a corresponding lower subset of adjacent teeth, the method further comprising: determining an absolute difference between an upper tooth and a corresponding point on a lower teeth; storing the plurality of absolute differences in a bite pattern descriptor matrix.

In another embodiment, the method further comprises rendering the bite registration descriptor matrix in a visualization map such that each entry in the bite registration descriptor matrix is replaced with a corresponding shade intensity.

In another aspect there is provided a method of measuring dental change comprising: obtaining a first mesh image of a dental object and a second mesh image of the dental object after a time lapse; aligning the first mesh image and the second mesh image and assigning a common reference locus; for each of the first mesh image and the second mesh image, extending a plurality of indexing rays from the reference locus to a surface boundary; creating a 2D descriptor matrix for each of the first mesh image and the second mesh image by: for each of the plurality of indexing rays, measuring a length from the reference locus to the surface boundary to generate a plurality of indexing ray lengths; and storing the plurality of indexing ray lengths in a 2D matrix to create the 2D descriptor matrix; and storing the 2D descriptor matrix for the dental object and the dental object after a time lapse as a matrix descriptor stack, wherein the cell of each row and column in each 2D descriptor matrix corresponds with the same indexing ray such that the 2D descriptor matrixes are stacked in space; and comparing the 2D descriptor matrixes to determine deviation after the time lapse.

In another embodiment, the dental change is one or more of orthodontic shift, periodontal change, and tooth degradation.

In another aspect there is provided a method of measuring dental occlusion comprising: obtaining an occlusal three-dimensional (3D) mesh image comprising a top bitewing and bottom bitewing in occlusal alignment, the mesh image comprising a top occlusal surface and a bottom occlusal surface; extending a plurality of indexing rays from a reference locus through the mesh such that each of the plurality of indexing rays intersects with the top bitewing and the bottom bitewing; creating a bite pattern descriptor matrix by: for each of the plurality of indexing rays, measuring a length from the reference locus to a surface of the bottom bitewing and a surface of the top bitewing to generate a plurality of indexing ray lengths; and storing the plurality of indexing ray lengths as a measurement of absolute distance between the surface of the bottom bitewing and the surface of the top bitewing to generate the bite pattern descriptor matrix of the occlusal surface.

In another embodiment, the method further comprises applying a threshold to the bite pattern descriptor matrix to identify loci below a certain threshold indicative of locations of good occlusal interaction between the upper bitewing and the lower bitewing.

In another embodiment the occlusal three-dimensional (3D) mesh image is obtained using occlusal radiography or computed tomography.

In another embodiment, the method further comprises matching the bite pattern descriptor matrix to similar the bite pattern descriptor matrixes in a descriptor database using a trained convolutional neural network to evaluate the degree of dental occlusion.

In another aspect there is provided a computer-implemented method of generating two-dimensional (2D) descriptors for three-dimensional (3D) objects, the method comprising: slicing a three-dimension (3D) representation of an object into an equal number of two-dimension (2D) cross-section slices; for each 2D cross-section slice: determining a centroid of that slice; and determining a plurality of radial lengths, each radial length between the centroid and a different point on a perimeter of the cross-section, each radial length separated by a same angle measured from the centroid; storing the plurality of radial lengths in a first descriptor matrix, wherein: a first dimension of the first descriptor matrix comprising a number of the plurality of cross-section slices; and a second dimension of the first descriptor matrix comprising a number of the plurality of radial lengths in each slice; and rendering the first descriptor matrix such that each entry in the first descriptor matrix is replaced with a corresponding color. Selected descriptors can then be stacked and processed through one or more convolutional auto encoders.

In an embodiment of the method, said slicing comprises radially slicing the object from its centroid. In another embodiment of the method, said slicing comprises slicing parallel cross-sections of the object.

In another embodiment of the method, the object comprises a tooth; and the first descriptor matrix comprises a tooth descriptor matrix.

In another embodiment, the method comprises generating a tooth descriptor stack, wherein the tooth descriptor stack comprises the tooth descriptor matrix and its corresponding rendering.

In another embodiment of the method, the object comprises a group of adjacent teeth.

In another embodiment of the method, said slicing comprises slicing parallel cross-sections of the group of adjacent teeth.

In another embodiment of the method, said slicing comprising radially slicing cross-sections of the group of adjacent teeth from a focal point outside the group of adjacent teeth.

In another embodiment, the method further comprises: generating a group descriptor stack for the group of adjacent teeth, wherein the first descriptor matrix comprises: a group descriptor matrix comprising: an overall group descriptor submatrix; and a tooth submatrix for each tooth in the group of teeth, wherein each submatrix for each tooth comprises: the same dimensions as the overall group descriptor submatrix; and zero or null entries for the other teeth in the group of teeth; and corresponding renderings of the overall group descriptor submatrix and each tooth submatrix. Different types of descriptors can also be stacked and passed through convolutional auto encoders to regenerate the descriptor again to train a convolutional auto encoder.

In another embodiment, the method further comprises generating a shade pattern descriptor stack, wherein the shade pattern descriptor stack comprises: the quadrant descriptor matrix rendered in full color; a red rendering of the overall quadrant descriptor matrix wherein only the red intensity values are rendered; a green rendering of the overall quadrant descriptor matrix wherein only the green intensity values are rendered; a blue rendering of the overall quadrant descriptor matrix wherein only the blue intensity values are rendered; and a monochromatic shading of the overall quadrant descriptor matrix wherein each color value in the overall quadrant descriptor matrix is converted to a single monochromatic intensity.

In another embodiment of the method, the object comprises a set of teeth comprising an upper subset of adjacent teeth and a corresponding lower subset of adjacent teeth, and the method further comprises: locating a centroid outside a 3D representation of the set of teeth; and for each 2D cross-section slice: locating an axis of the slice corresponding to a same axis of the set of teeth; determining a plurality of radial lengths between the centroid and a different point on a portion of the perimeter of the cross-section defined by an axis upper bounding value for the subset of upper teeth and an axis lower bounding value for the subset of lower teeth; determining an absolute difference between a distance determined for a point on the upper teeth and a distance determined for a corresponding point on the lower teeth; and storing the plurality of absolute differences in a bite pattern descriptor matrix, wherein: a first dimension of the bite pattern descriptor matrix comprising a number of the plurality of cross-section slices; and a second dimension of the bite pattern descriptor matrix comprising a number of the plurality of absolute differences in each slice; and rendering the bite registration descriptor matrix such that each entry in the bite registration descriptor matrix is replaced with a corresponding shade intensity.

In another embodiment of the method, absolute difference values greater than a predetermined distance are given a value of zero, thereby converting the bite registration descriptor matrix to a bite pattern descriptor matrix.

In another embodiment, the method further comprises adding a plurality of stacks to a neural network to get a smaller size data set.

In another aspect there is provided a system for generating two-dimensional (2D) descriptors for three-dimensional (3D) objects, the system comprising: at least one processor; and a memory storing instructions which when executed by the at least one processor configure the at least one processor to: slice a three-dimension (3D) representation of an object into an equal number of two-dimension (2D) cross-section slices; for each 2D cross-section slice: determine a centroid of that slice; and determine a plurality of radial lengths, each radial length between the centroid and a different point on a perimeter of the cross-section, each radial length separated by a same angle measured from the centroid; store the plurality of radial lengths in a first descriptor matrix, wherein: a first dimension of the first descriptor matrix comprising a number of the plurality of cross-section slices; and a second dimension of the first descriptor matrix comprising a number of the plurality of radial lengths in each slice; and render the first descriptor matrix such that each entry in the first descriptor matrix is replaced with a corresponding color. Selected descriptors can then be stacked and processed through one or more convolutional auto encoders.

In an embodiment of the system, the at least one processor is configured to radially slice the object from its centroid.

In another embodiment of the system, the at least one processor is configured to slice parallel cross-sections of the object.

In another embodiment of the system, the object comprises a tooth; and the first descriptor matrix comprises a tooth descriptor matrix.

In another embodiment of the system, the at least one processor is configured to generate a tooth descriptor stack, wherein the tooth descriptor stack comprises the tooth descriptor matrix and its corresponding rendering.

In another embodiment of the system, the object comprises a group of adjacent teeth.

In another embodiment of the system, the at least one processor is configured to slice parallel cross-sections of the group of adjacent teeth.

In another embodiment of the system, the at least one processor is configured to radially slice cross-sections of the group of adjacent teeth from a focal point outside the group of adjacent teeth.

In another embodiment of the system, the at least one processor is configured to: generate a group descriptor stack for the group of adjacent teeth, wherein the first descriptor matrix comprises: a group descriptor matrix comprising: an overall group descriptor submatrix; and a tooth submatrix for each tooth in the group of teeth, wherein each submatrix for each tooth comprises: the same dimensions as the overall group descriptor submatrix; and zero or null entries for the other teeth in the group of teeth; and corresponding renderings of the overall group descriptor submatrix and each tooth submatrix.

In another embodiment of the system, the at least one processor is configured to: generate a shade pattern descriptor stack, wherein the shade pattern descriptor stack comprises: the quadrant descriptor matrix rendered in full color; a red rendering of the overall quadrant descriptor matrix wherein only the red intensity values are rendered; a green rendering of the overall quadrant descriptor matrix wherein only the green intensity values are rendered; a blue rendering of the overall quadrant descriptor matrix wherein only the blue intensity values are rendered; and a monochromatic shading of the overall quadrant descriptor matrix wherein each color value in the overall quadrant descriptor matrix is converted to a single monochromatic intensity.

In another embodiment of the system, the object comprises a set of teeth comprising an upper subset of adjacent teeth and a corresponding lower subset of adjacent teeth; and the at least one processor is configured to: locate a centroid outside a 3D representation of the set of teeth; for each 2D cross-section slice: locate an axis of the slice corresponding to a same axis of the set of teeth; said determining of the radial length comprises determining a plurality of radial lengths between the centroid and a different point on a portion of the perimeter of the cross-section defined by an axis upper bounding value for the subset of upper teeth and an axis lower bounding value for the subset of lower teeth; determine an absolute difference between a distance determined for a point on the upper teeth and a distance determined for a corresponding point on the lower teeth; store the plurality of absolute differences in a bite pattern descriptor matrix, wherein: a first dimension of the bite pattern descriptor matrix comprising a number of the plurality of cross-section slices; and a second dimension of the bite pattern descriptor matrix comprising a number of the plurality of absolute differences in each slice; and render the bite registration descriptor matrix such that each entry in the bite registration descriptor matrix is replaced with a corresponding shade intensity.

In another embodiment of the system, absolute difference values greater than a predetermined distance are given a value of zero, thereby converting the bite registration descriptor matrix to a bite pattern descriptor matrix.

In another embodiment of the system, the at least one processor is configured to add a plurality of stacks to a neural network to get a smaller size data set.

Many further features and combinations thereof concerning embodiments described herein will appear to those skilled in the art following a reading of the instant disclosure.

BRIEF DESCRIPTION OF THE FIGURES

Embodiments will be described, by way of example only, with reference to the attached figures, wherein in the figures:

FIG. 6A illustrates an example single tooth mesh file;

FIG. 6B illustrates an example of a single tooth analyzed by an indexed slicer sliced radially into a plurality of radial portions;

FIG. 6C illustrates an example cross-sectional plane from the indexed slicer sliced into indexing rays;

FIG. 9 illustrates a selection of tooth descriptor surfaces of a single tooth object described in relation to a common centroid and associated visualization maps;

FIG. 18A illustrates an example of the z-axis position for a quadrant in a dental arch;

FIG. 18B illustrates planar slices of the dental arch where each slice intersects with the arch centroid;

FIG. 18C shows a single slicing plane and dental object cross sectional boundary;

FIG. 20A illustrates an example of a full arch;

FIG. 20B illustrates an example of a right-side half arch;

FIG. 20C illustrates an example of a left-side half arch;

FIG. 23A illustrates an example method of obtaining a tooth descriptor matrix;

FIG. 23B illustrates an example method of obtaining a quadrant descriptor matrix stack for a bitewing;

FIG. 29A illustrates an example of a bitewing with bitewing common centroid;

FIG. 29B illustrates an example of a cross-sectional slice of a bitewing;

FIG. 32A is a front view of a mesh file bite image;

FIG. 32B is a side view of mesh file bite image;

FIG. 32C is a top view of bottom dental arch mesh file bite image;

FIG. 33A illustrates an example bite pattern matrix descriptor visualization;

FIG. 33B illustrates an example bite pattern registration descriptor visualization;

It is understood that throughout the description and figures, like features are identified by like reference numerals.

DETAILED DESCRIPTION

Figure 1:
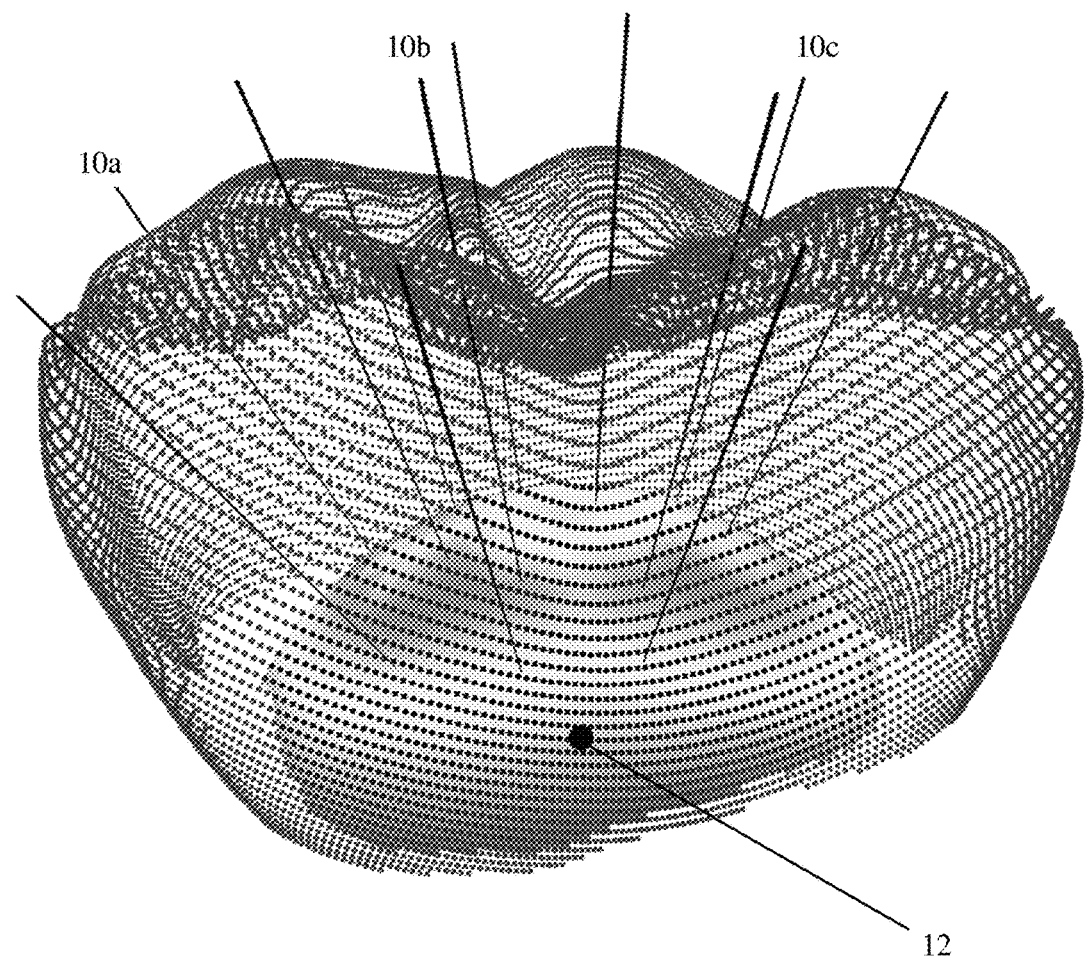
FIG. 1 illustrates a tooth object having an assigned centroid with rays originating from the centroid.

Embodiments of methods, systems, and apparatus are described through reference to the drawings. Applicant notes that the described embodiments and examples are illustrative and non-limiting. Practical implementation of the features may incorporate a combination of some or all of the aspects, and features described herein should not be taken as indications of future or existing product plans.

Herein is provided a method and system to process tessellated or mesh 3D file formats in dental applications. The described dental image file capture and manipulation can be used for the purpose of dental, orthodontic, and periodontic tracking, diagnostics, and dental prosthetic and implant design. Augmented intelligence in dental file segmentation as described herein converts standard STL or tessellated mesh file image formats into one or more two dimensional (2D) descriptor matrixes with a common reference point or reference locus. Multiple descriptor matrixes having the same common reference locus describing related dental surface structures enables the description of different dental surfaces around the common reference locus in a single patient. These can include, for example, gum surfaces, post surface, interior and exterior crown surfaces, and other occlusal surfaces in the mouth.

The conversion of the standard 3D image mesh files into one or more 2D descriptor matrixes reduces the data size of dental image files such that dental images can be manipulated and compared to other dental files and can be used in machine learning and matching systems. This expedites the design and manufacture of dental prosthetics and appliances because machine learning systems can more easily and quickly match related descriptor matrixes, thus reducing the cost of dental monitoring and treatment. Storage of dental files is also reduced in cost by reducing the file size, thus facilitating the tracking of dental patients for dental professionals. In addition, dental structures from the same patient can be compared over time, such as periodontic and tooth shifting to provide accurate dental tracking. Various orthodontic and periodontal patterns can be learned from specially formatted stacked arrays database using deep learning algorithms.

To be "stackable" for describing 3D patterns, each surface in the dental object is described by a unique descriptor matrix and all of the descriptor matrixes describing the same dental object have common reference locus or centroid from which all measurements are taken. The stacked descriptor matrixes contain data related to distances from a surface to the shared common reference locus, and each data point in each of the stacked descriptor matrixes represents a distance from the common reference locus describing a surface shape and is stored in the same location in the descriptor matrix such that they are anchored in space relative to one another. The plurality of surfaces in the dental object are thus each described by a separate descriptor matrix, however in relation to the same common reference locus. In particular, each data point in the same cell of related is stacked matrixes is related along the same indexing ray as the distance between the reference locus and the surface described by each individual descriptor matrix. This provides a descriptor stack which describes multiple surfaces in the same dental object, such as, for example, gumline, gum surface, neighbouring tooth surface, occlusal tooth surface on an opposite jaw to the dental object, arch surface, inside prosthetic surface, post surface, outside prosthetic surface, and appliance surface. A plurality of features can thereby be described with a single descriptor matrix stack, where each matrix visualizes a single feature or single surface of the dental object.

Data sets comprising descriptor matrix stacks describing orthodontic and periodontics patterns are between 10 and 100 times smaller than the data contained in the digital impression files in native format (STL or any meshing format) required for encoding all the stacked arrays. Due to the reduced size of the present data sets compared to their corresponding mesh files, orthodontic and periodontal patterns can be clustered in a very large database to match any specific patterns within seconds using a trained convolutional neural network to assist with treatment, for example surgery planning, orthodontic treatment planning, and prosthetic design. For example, when sub-optimal orthodontic or periodontal patterns can be recognized, optimal orthodontic or periodontal treatment patterns can be proposed as restorative solutions nearly instantly by matching the various descriptor matrixes in the descriptor stack with similar descriptor matrixes and orthodontic or periodontic restorative solutions can be recommended based on the similar descriptor matrixes and prognosis of similar cases. Periodontal patterns can be used to diagnose early gum disease based on a combination of gum thickness and gum height compare to the tooth height or gum recess. Periodontal patterns can also be used to plan restorative solutions including planned gum graft when gum recess is exceeding a set threshold.

Dental object matching, either with dental objects from different patients or in the same patient after a period of time or time lapse, can be done using the present method of dental file segmentation followed by representation of the three dimensional (3D) dental object as a two dimensional (2D) matrix. A computer-implemented system and method of generating two-dimensional (2D) descriptors for three-dimensional (3D) objects by the conversion of mesh files into descriptor matrixes and comparing and matching said descriptor matrixes is thereby provided. One example method comprises slicing a three-dimension (3D) representation of a dental object into a number of two-dimension (2D) cross-sectional slices, and for each 2D cross-sectional slice determining an indexing centroid and a plurality of radial lengths measured from the slicing centroid to the cross-sectional boundary. Each radial length is measured between the indexing centroid or reference locus and a different point on a perimeter or surface boundary of the cross-section and preferably each radial length is separated by a same angle measured from the indexing centroid. The plurality of radial lengths are then stored in a descriptor matrix. In one example, a first dimension or row of the resulting 2D descriptor matrix comprises an identification of the number of the plurality of cross-section slices or slicing planes, and the second dimension or column of the descriptor matrix comprises the number and lengths of each of the plurality of indexing rays in each slice or slicing plane. In another example the descriptor matrix dimensions can comprise, for example, declination angle from normal relative to a z-axis that extends through the dental object and a right ascension angle from a reference point perpendicular to the z-axis to define the dental object in a 2D descriptor matrix, referred to herein as an angular indexing method. Preferably, for the purpose of visualization, each descriptor matrix is converted into a visualized form or visualization map such that each entry in the descriptor matrix is replaced with a corresponding color or shade by parsing the length data into ranges and assigning a color or shade to each range.

The 2D descriptor matrix can be assigned a descriptor type based on the type or surface of dental object imaged and represented by the descriptor matrix, and a plurality of descriptor matrixes can be generated for the same dental object or dental object region. When the dental object is assigned a common centroid or reference locus and multiple descriptor matrixes are created using the reference locus, the plurality of descriptor matrixes of the same dental object or region can be stacked to provide a multi-dimensional view of the dental object, where each descriptor matrix can be independently matched with similar descriptor matrixes in a descriptor database. This can assist with, for example, dental prosthetic and appliance design, and in monitoring and prescribing change in the mouth for orthodontic and periodontic applications.

The present method and system provides a mechanism by which 3D objects can be represented using one or more 2D array or matrixes which have a smaller file size and comprise less data than their 3D image counterpart. Each array can describe a key feature of a complex object and can be used to match similar 3D objects and features in a database for a variety of applications, including but not limited to detection of change in shape over time, defect detection, comparison to a standard, computer-aided design, and computer-aided manufacturing. Once the 3D object is segmented, each descriptor matrix can be stacked and classified by key feature and compared against other key feature matrixes using a Convolutional Auto Encoders for matching and analysis. The system comprises at least one processor and a memory storing instructions which when executed by the at least one processor configure the at least one processor to carry out the presently described methods. Different types of descriptors can also be stacked and passed through a Convolutional Auto Encoder to regenerate the descriptor again and train the Convolutional Auto Encoder for augmented intelligence in 3D file matching and CAD. The present method will not only be helpful to the dental industry but may also have a significant impact for the CAD/CAM industry and other industries that use tessellated surfaces and tessellated or mesh file formats.

In various further aspects, the disclosure provides systems, methods, devices, and logic structures and machine-executable coded instruction sets for implementing such systems, devices, and methods. In some embodiments, five (5) STL autoencoders are proposed to process full dental arches digital impression files, followed by a stacking of these 2D arrays/matrices to describe the full dental feature or object which the corresponding 3D STL file describes. A compact dataset may thus be derived from the descriptor matrixes. A bite pattern and a bite registration descriptor matrix may also be generated from a 3D occlusal bite image for better bite analysis and comparison.

The present disclosure may be described herein in terms of various components and processing steps, and each component provides different features of dental anatomy. Some processing steps described herein include an indexed slicer, a radial encoder, a Fourier neural operator, and a visualization unit which converts the descriptor matrix into an image file format that can be viewed on a screen in a graphical user interface. The visualized output or visualization maps may also be stacked to facilitate imaging of a plurality of features into a single object. In some embodiments, an indexed slicer divides dental anatomy into slices so that a plurality of cross-sections can be created which can further be indexed and converted to a numerical representation in a radial encoder. In some embodiments, the radial encoder may map the cross-section from a particular slicing centroid. Once a mapping has been completed the next step is to store the data strategically. In some embodiments, this is achieved by a Fourier neural operator and an output visual rendering for each 2D array/matrix value mapping (visualisation) that allows a field expert (e.g. dentist, data scientist, software developer, etc.) to recognize each key feature described by each array. The set of descriptor matrixes may then be stacked to describe the full dental anatomy. For example, into a tooth descriptor stack, a quadrant descriptor stack, a dental arch descriptor stack, and/or a shade pattern descriptor stack. Furthermore, a bite pattern and a bite registration descriptor may be provided in a similar manner as the encoding method. These descriptors allow for two output formats: 2D array/matrix, and image format. With these descriptors, one can review the bite, compare before and after the dental implant or crown. A compact dataset is a small data set which represents more than one key features.

The herein mentioned components can be performed in a variety of hardware types. One skilled in the art understands that the methods described below may import meshes from various formats including binary/ASCII STL, Wavefront OBJ, ASCII OFF, binary/ASCII PLY, GLTF/GLB 2.0, 3MF, XAML, 3DXML, etc. For simplicity of the present description, STL or mesh format form will be used herein as an exemplary file format, however it is understood that other 3D file formats describing surface structures may also be used with the described methods. The methods described below are a few of the exemplary applications for the present disclosure. The principle, features, and methods discussed herein may be applied to any dental application that works with three-dimensional anatomy, or any 3D anatomy comprising a surface structure that can be imaged. It should be noted that the methods and descriptor stacks described herein can also have an application other than the dental industry and the embodiments are not limited in application to the details of construction and to the arrangements of the components set forth in the present description or illustrated in the drawings. The phraseology and terminology employed herein are for the purpose of description and should not be regarded as limiting. It should also be noted that for illustrative purposes, the various exemplary methods and systems may be described in connection with a single tooth or other oral or dental structure of a patient. However, such exemplary methods can also be implemented with another type of tooth or dental object within a patient such as molars, canines, premolars, etc. For example, an incisor tooth may be illustrated in a single tooth descriptor method, and the same method can also be performed with premolars, molars, and other teeth. In some embodiments, similar ideology may apply to other methods and descriptor stacks.

FIG. 1 illustrates a tessellated image or mesh file representing a tooth object. The image of the tooth object has an assigned common centroid 12 serving as a reference locus with rays originating from the common centroid. The common centroid 12 is selected or assigned relative to the image of the dental object at an approximately central location, and the distance from the common centroid to each layer in the tooth object can be index, mapped in a 2D format in a descriptor matrix, and the descriptor matrixes stacked such that they have a common centroid anchor or reference point. The black lines describe the paths of centroid indexing rays 10a, 10b, 10c being shot from or extending from a single common centroid 12 point. Rays are extended from the common centroid 12 at evenly spaced angle intervals in all directions. Each time a ray intersects with the surface of the mesh of the STL file describing the dental object or tooth, the distance that the ray travelled is stored in a two-dimensional array representing all rays shot. The dental object can be segmented in a few different ways to generate the set of 2D descriptor matrixes that describe the dental object, for example using parallel or radial slicing or by angular indexing. With a common centroid for each descriptor matrix the set of matrixes are indexed relative to one another, enabling independent segmentation, searching, and optimization of the surface described by each descriptor matrix.

Figure 2:
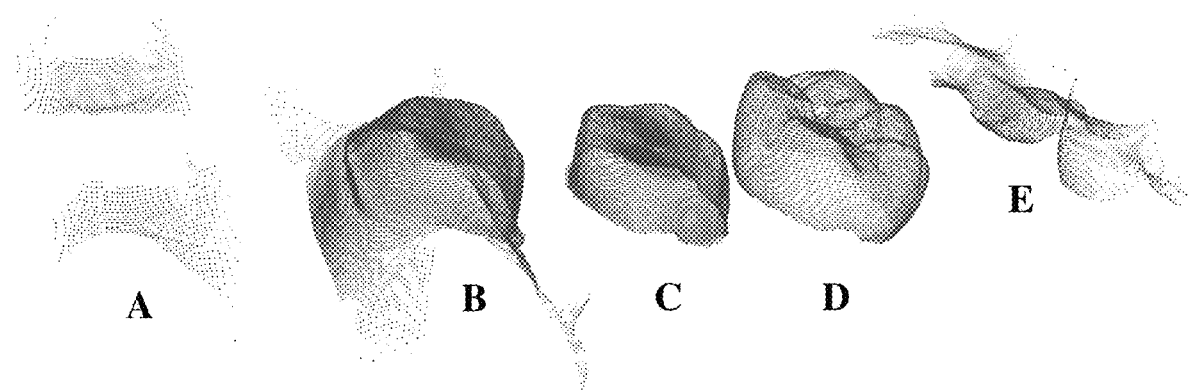
FIG. 2 illustrates a selection of tooth descriptor surfaces of a single tooth object described in relation to a common reference locus.

FIG. 2 illustrates a selection of tooth descriptor surfaces described in relation to a common reference locus. This figure illustrates that with this encoding method, 3D mesh representations of the dental object can be segmented into different features with each view related by a common reference locus or centroid such that they can be overlapped in space and independently searched and optimized. The features of a bottom jaw dental location illustrated are from left to right, where: feature A is the surface of a preparation site (adjacent tooth walls); feature B is the surface of the preparation site (the post); feature C is the inside surface of a fabricated crown (inside surface); feature D is the outside surface of the fabricated crown (outside surface); and feature E is the occlusal surface of neighbouring top teeth in the top jaw. In one application of the present invention a crown can be designed by matching the inside of the crown (feature C) to the patient's post (feature B), and independently designing the outside of the crown (feature D) to match the preparation site (feature A) as well as the occlusal surface (feature E), each with its own descriptor matrix. Computer-aided design (CAD) can be done by matching similar descriptor matrixes to the one being designed to a machine learning trained model to provide a complete crown that fits into the patient's mouth, taking into consideration all aspects of the crown environment.

Figure 3:
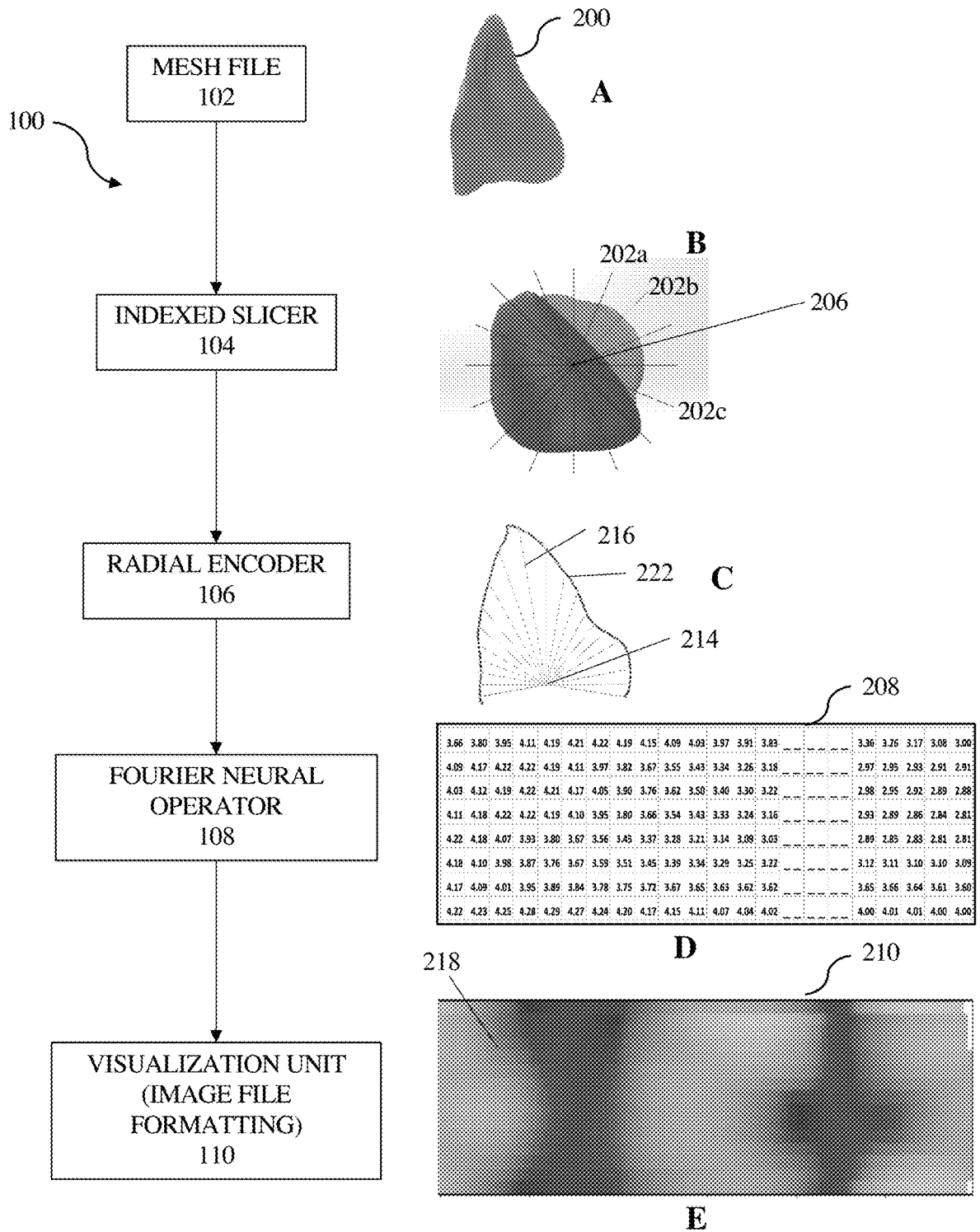
FIG. 3 illustrates, in a component and schematic diagram, an example of a descriptor generation platform and examples outputs of components of the descriptor generation system employing an example of a single tooth description method.

FIG. 3 illustrates, in a component diagram, an example of a descriptor generation system 100, in accordance with some embodiments. The system 100 comprises an indexed slicer 104, a radial encoder 106, Fourier neural operator 108, and a visualization unit 110 for image file formatting. The indexed slicer 104 receives an STL or mesh file 102 as an input source and the Fourier neural operator 108 in the system 100 generates a matrix/array output which can be visualized on visualization unit 110. The terms "matrix" and "array" are used interchangeably herein to refer to the two dimensional data structure comprising numerical measurements represented in a two dimensional x,y array, where each numerical measurement is a distance from a common reference locus to a dental surface. Each matrix may differ based on the method it is used for, and the visualization unit 110 can provide an output image on a graphical user interface on a display screen. The visualized output can simply be the array of numbers as shown adjacent Fourier neural operator 108, or can be a parsed output, for example where ranges of numbers are represented by colors or in greyscale, as shown adjacent visualization unit 110. The image output at the visualization unit 110 can be of any standard image file format capable of being visualized. Different descriptors may be generated using the descriptor generation system 100, including a single tooth descriptor method 1, a single tooth descriptor method 2, an arch descriptor method 1, an arch descriptor method 2, and a full arch descriptor, all described herein. Additionally, various different descriptor matrixes for a single dental object can be obtained, such as, for example, gumline, gum surface, neighbouring tooth surfaces, occlusal tooth surfaces adjacent to or on the opposite jaw of the dental object, arch surface, inside and outside of prosthetic surfaces, and appliance surfaces.

A single tooth descriptor method is illustrated as images A-E in FIG. 3, where images A-E illustrate example outputs of components of the descriptor generation system 100 employing an example of a single tooth description method, in accordance with some embodiments. This method comprises processing of three-dimensional single tooth files from their native 3D format to a two-dimensional (2D) matrix format shown as 2D matrix 208 in image D or visualization map 210 shown in image E. Image A illustrates an example of a dental object 200 in a native three-dimensional tooth file (e.g., STL file format). The present method can be achieved by slicing the three-dimensional tooth or dental object 200 into equally angled slicing planes by the indexed slider 104 shown in image B. The dental object 200 is passed through the indexed slicer 104 where, in this embodiment, the dental object 200 is sliced radially. In a preferred embodiment with radial slicing, each slice will pass through the dental object common centroid, however it is noted that slicing can also be done in, for example, parallel or near parallel planes, or using angular indexing. As shown in image B, the dental object is analyzed by the indexed slicer where, in the present example method, the dental object is sliced radially into a plurality of radial portions through the slicing centroid 206. In the embodiment shown, each radial slice will pass through the tooth common centroid or z-axis. As shown in image B, all radial slicing planes 202a, 202b, 202c that are generated have a consistently increasing angle alpha ($\alpha$) such that the difference in angle or degrees from one radial slicing plane to the next is the same. In some embodiments, increasing the number of radial slicing planes in the method will increase the accuracy of the descriptor generation such that the resulting 2D matrix provides more granularity on the 3D shape of the dental object. Radial slicing planes 202a, 202b, 202c that are generated are preferably equally angled to provide consistent density of distance data for the dental object surface. Each slicing plane 202a, 202b, 202c will generate a different cross-sectional view of the dental object 200 at a different angle. Image C shows a 2D cross section of one slicing plane shown in image B. As shown in image C, the distance from the indexing centroid 214 to the intersection of each cross-sectional point or tooth cross sectional boundary 222 on the circumference of the dental object slice, or the length of each indexing ray 216, may be measured by the radial encoder. The indexing centroid 214 is the centroid of the cross-sectional plane of a single radial slicing plane generated from radial slicing of the dental object through a radial slicing plane. The radial encoder will generate a plurality of indexing rays 216 originating at the indexing centroid 214, where the distance between the indexing centroid 214 and the circumference of the cross-section of the radial slicing plane at the edge of the dental object can be generated from the slicing plane is measured by the radial encoder 106 to map the circumference of the dental object in the slicing plane. In a radial slicing method, the slicing centroid 206 can also be at the same location as the indexing centroid of each cross-section generated from slicing plane 202a, 202b, 202c. The radial encoder 106 will generate indexing rays 216 from the indexing centroid 214 which maps the length of each indexing ray from the indexing centroid to the dental object cross-sectional boundary 222 in each radial slice. In some embodiments, all the indexing rays will be equally angled in space at an angle beta ($\beta$) such that the angle between each indexing ray 216 is constant. It should be noted that the cross section created by the indexed slicer 104 can also be measured and referenced from a different location or reference locus on the dental object, such as, for example, a bottom plane of the dental object instead of an indexing centroid as shown, producing a different orientation of the resulting descriptor matrix for the dental object at the described surface. Increasing the number of indexing rays generated will provide more detail about the dental object, for example the tooth anatomy, by capturing more data points around the tooth cross-section circumference. However, more circumferential data points as provided by the distances of the plurality of indexing rays will increase the 2D matrix file size, accordingly this should be kept in mind when determining the number of slicing planes as well as indexing rays required to provide adequate precision required for the desired purpose. To compare descriptor matrixes for the same dental object it is preferred that the location of the reference point for slicing as well as indexing, or the algorithm used to create the descriptor matrixes, is consistent to enable straight-forward comparison of similar dental matrixes.

Image D illustrates an example of a radial encoder output of the Fourier neural operator 108 as a 2D matrix 208 for the tooth object shown in images A and B. A 2D matrix 208 is generated for each radial portion or slicing plane 202a, 202b, 202c of the tooth dental object shown in image B. For each cross sectional slice or slicing plane the radial encoder measures the distance from the indexing centroid to the cross sectional boundary and generates a one dimensional list of distances (1D array) which describes the surface boundary 22 for the particular slicing plane. This is repeated for every slicing plane, and combining all of the 1D arrays for each slicing plane will create the 2D matrix 208 of the dental object 200 using a Fourier neural operator. Other mathematical functions can also be applied to the 1D arrays or 2D matrix to manipulate the numbers present in those array to a manageable range, such as by reducing the number of significant digits or by normalizing the numbers. Applying a normalization function can also result in reduction of the data or file size of the 2D matrix 208. In an example, if the indexing centroid is placed a significant distance away from the dental object slice, the neural operator can adjust the values in the 1D matrix by normalizing the offset distance of the indexing centroid. In a specific example, array (102, 103, 100) can be represented by array (2,3,1) with a base of 100. The 1D array (2,3,1) consumes less space as compared to (102,103,100) bytewise, but normalization of the values has not decreases the accuracy of the matrix. One open source method that can be used for such value normalization is Apache parquet. It should be understood that a full matrix describing the whole dental object may have many rows and columns, potentially on the order of hundreds or thousands of rows and columns to provide sufficient granularity for the entire anatomy of the dental object. The data in the 3D matrix represents the actual distance, for example in mm, and the smallest number from all the numbers in the 3D matrix can removed through normalization, such that the 3D matrix represents the relative difference or dental variation present in the mesh file. As will be shown, each entry in the matrix may be used as a pixel value in a visualization mapping/image.

In some embodiments, the number of rows is equal to the number of slicing planes generated from the indexed slicer 104 and the number of columns is equal to the number of ray lengths generated in each slicer in the radial encoder 106. Each element or cell in the 2D matrix represents a distance from the slicing centroid 206 to a cross-section boundary point of that slicing. The output of the Fourier neural operator is the 2D matrix 208 which can further be used in stacking applications as described below. Image E in FIG. 3 is an illustration of a visualization map 210 of the radial encoder output 2D matrix 208 visualized as a pixel array. The visualization map 210 of the radial encoder 106 output can be visualized on a graphical user, where each entry in the 2D matrix 208 is converted to a pixel value, referred to herein as a visualization map 210. The 2D matrix 208 may be visualized in this way as an aid to a dentist or lab technician for further analysis. In one way of converting the 2D matrix 208 into a visualization map 210, for example, the value of the Neural operator matrix may be mapped to a color mapping method (e.g., rainbow color, single color shading, multiple color shading, black and white or greyscale shading, etc.). The minimum and maximum values of the matrix may be identified and assigned to a selected color map value extreme point and the 2D matrix 208 may be represented as a color map or visualization map 210. Image E illustrates an example of a greyscale (black and white range) visualization mapping of matrix 208. The values in matrix 208 are represented as shading shown in pixel region 218. Again, a full matrix would correspond to the entire visualization mapping/image such that each conversion of a matrix entry to a colour/shading may be represented as a pixel in the visualization map 210.

Figure 4:
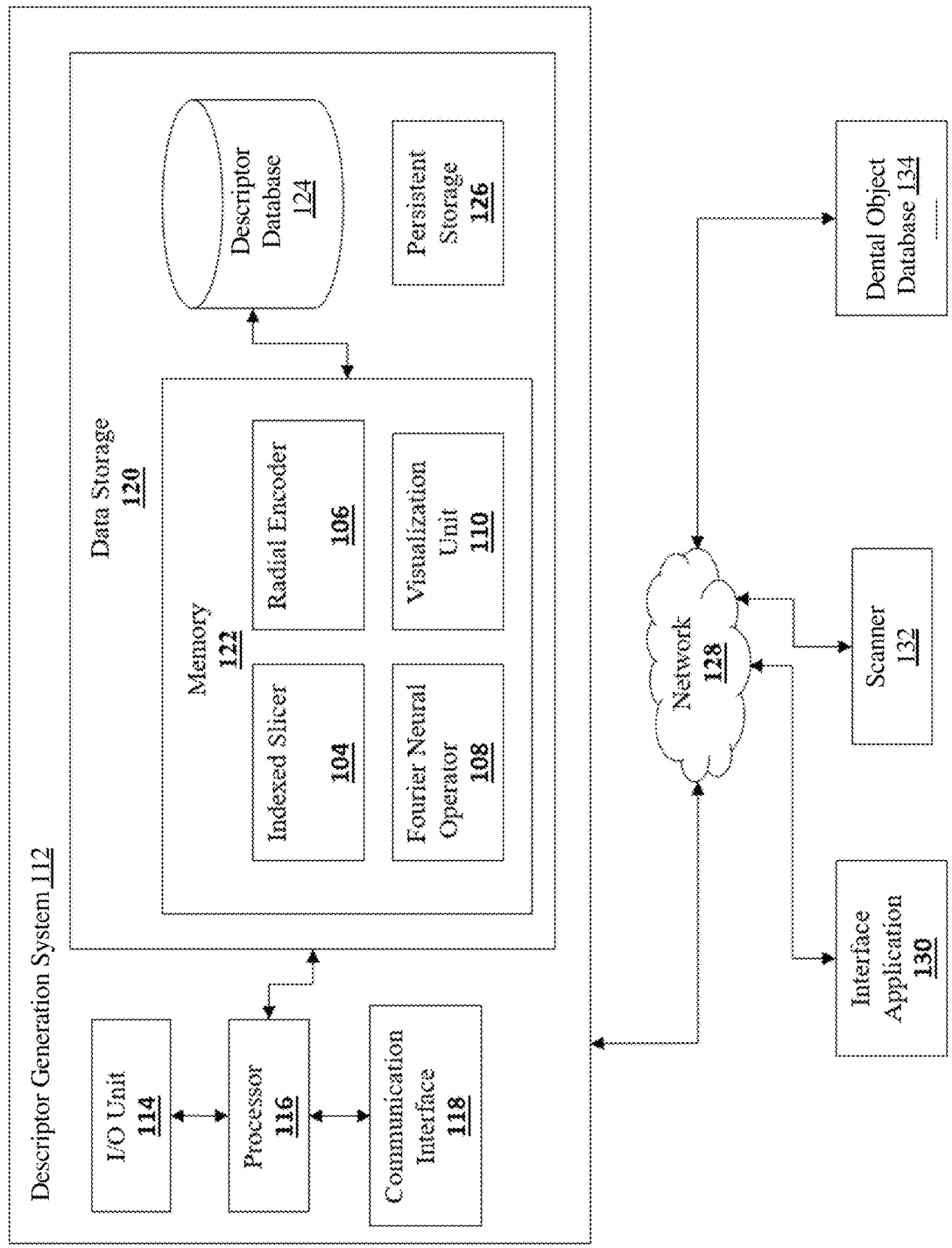
FIG. 4 illustrates, in a schematic diagram, an example of a descriptor generation system.

FIG. 4 illustrates, in a schematic diagram, is an example of a descriptor generation system 112 in accordance with some embodiments. The system comprises at least one processor and a memory storing instructions which, when executed by the at least one processor, configure the at least one processor to perform the method as presently described. The descriptor generation system 112 is implemented on a computer or equivalent electronic device connected, either wired or wireless, to an interface application 130, a dental scanner 132 such as a dental imaging device that produces STL/mesh images, and one or more dental object databases 134 such as dental records or other data, via network 128. The interface application 130 can be, for example, a dental assessment interface application on a personal computer, a dental assessment device interface, or a mobile device application, generally comprising a graphical user interface, which enables a dental professional to interact with the system. The descriptor generation system 112 can implement aspects of the processes and methods described herein. The descriptor generation system 112 can be implemented on a suitable computer or electronic device and can include an input/output (I/O) unit 114 and a processor 116 using a communication interface 118 and a data storage 120. The descriptor generation system 112 also has a memory 122 storing machine executable instructions to configure the processor 116 to receive files, for example from Input/Output (I/O) unit 114, one or more dental scanner 132 device, or from one or more descriptor databases 124. The dental descriptor database 124 can, for example, be a database comprising a plurality of dental descriptor mesh or mesh files and/or matrix data files that can be called upon for matching, comparison, diagnostic, artificial intelligence or machine learning training or testing sets, or for other comparative purposes.

The descriptor generation system 112 can also include a communication interface 118, and data storage 120. The processor 116 can execute instructions in memory 120 to implement aspects of processes described herein. The descriptor generation system 112 can connect with one or more interface applications 130, dental scanner 132 devices, or dental object databases 134. This connection may be over a network 128 (or multiple networks), either wireless or wired or a combination thereof. The descriptor generation system 112 may receive and transmit data from one or more of these via I/O unit 114. When data is received, I/O unit 114 transmits the data to processor 116. The I/O unit 114 can enable the descriptor generation system 112 to interconnect with one or more input devices, such as a keyboard, mouse, camera, touch screen and a microphone, and/or with one or more output devices such as a display screen and a speaker. The processor 116 can be or comprise, for example, one or more of any one or more type of general-purpose microprocessor or microcontroller, for example, digital signal processing (DSP) processor, integrated circuit, field programmable gate array (FPGA), a reconfigurable processor, or any combination thereof. The data storage 120 can include memory 122, one or more dental descriptor database(s) 124 containing a plurality of dental object 2D matrix representations along with their descriptor class/subclass, and one or more persistent storage 126. Memory 122 may include a suitable combination of any type of computer memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like.

The communication interface 118 can enable the descriptor generation system 112 to communicate to the network 128 as well as with other components, to exchange data with other components, to access and connect to network resources, to serve applications, and/or perform other computing applications by connecting to one or more network or multiple networks capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g., Wi-Fi, WiMAX), SS7 signaling network, fixed line, local area network, wide area network, and others, including any combination of these. The descriptor generation system 112 can also be operable to register and authenticate users using, for example, a login, unique identifier, and password, prior to providing access to applications, a local network, network resources, other networks and network security devices. The descriptor generation system 112 can also be enabled to connect to different machines or entities over one or more communication interface 118. The data storage 120 may be configured to store information associated with or created by the descriptor generation system 112. Storage 120 and/or persistent storage 126 may be provided using various types of storage technologies, such as solid state drives, hard disk drives, flash memory, and may be stored in various formats, such as relational databases, non-relational databases, flat files, spreadsheets, extended markup files, etc. The memory 122 may also include the indexed slicer unit 104, the radial encoder unit 106, the Fourier neural operator 108, and the visualization unit 110 as described herein.

Figure 5A:
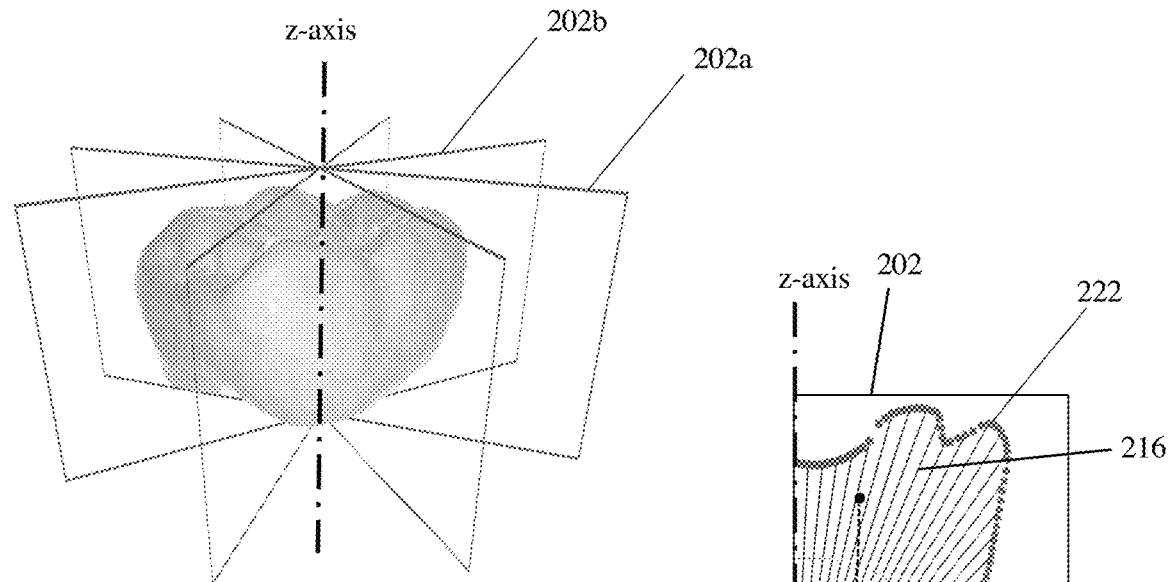
FIG. 5A illustrates a mesh file of the exterior surface layer of a tooth crown with a common z-axis.
Figure 5B:
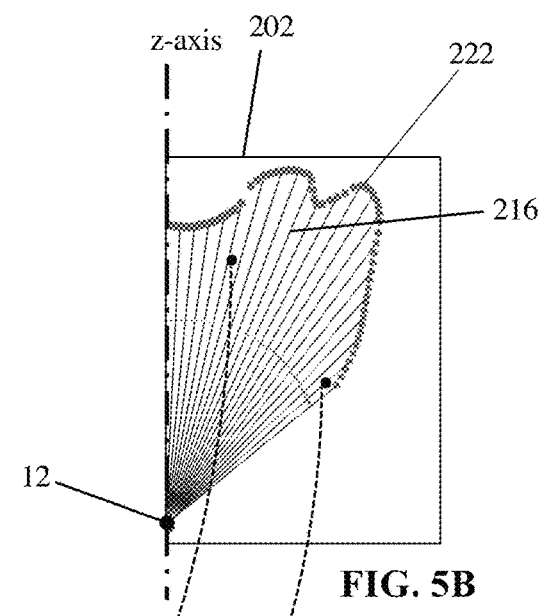
FIG. 5B illustrates half of a slicing plane describing the cross-section of a dental crown.
Figure 5C:
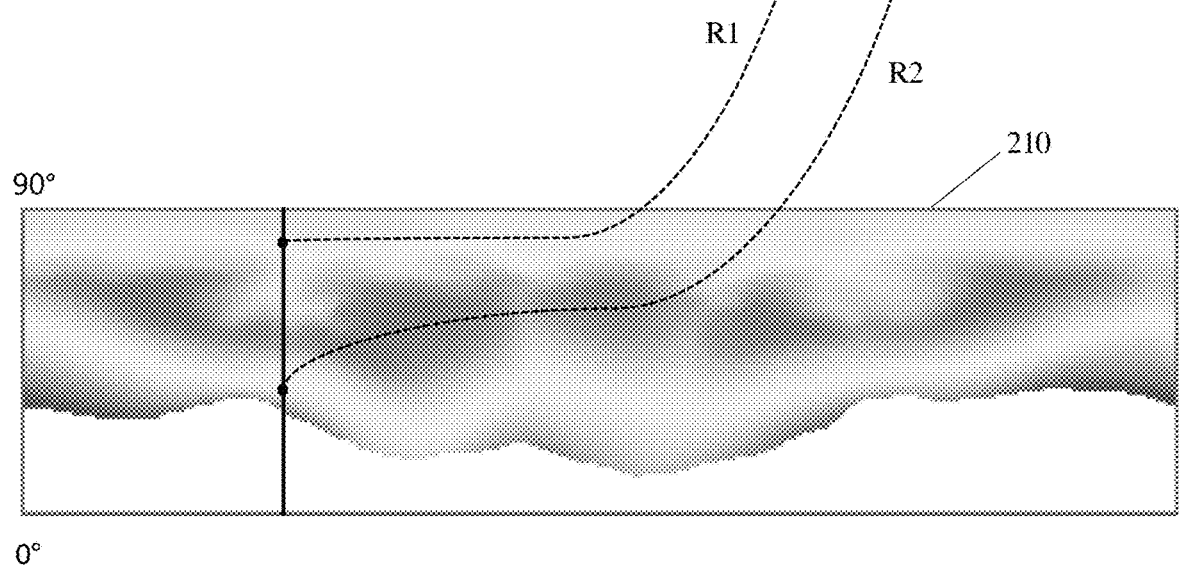
FIG. 5C illustrates a visualization map of the dental crown in FIG. 5A.

FIGS. 5A-5C describe a method of tooth segmentation to produce a visualization map of one layer of a tooth object, which in this case is the exterior surface of a dental crown. FIG. 5A illustrates a mesh file of the exterior surface layer of the tooth crown with a centroid z-axis that runs through the common centroid of the dental object, in this case a molar crown. Radial slicing planes 202a, 202b slice the tooth crown through the common centroid which is on the z-axis. FIG. 5B shows half of a single slicing plane which describes the cross-section of the dental crown showing the periphery of the crown at that slice as cross sectional boundary 222. Indexing rays 216 are extended out at evenly spaced angle intervals from common centroid 12 in all directions on the slicing plane 202 and measured using a radial encoder. It is noted that in this case the common centroid 12 lies on the z-axis, however well below the bottom surface of the dental crown object in space. This positioning of the common centroid 12 enables improved resolution control of the surface boundary. The common centroid 12 can be positioned anywhere inside the dental object or outside of the dental object, and even at a large or distance from the dental object, in which case the indexing rays will be effectively parallel to one another. At a large distance normalization of the indexing rays during processing reduces the file size of the resulting 2D matrix. Positioning of the common centroid 12 on the z-axis which serves as a reference locus enables descriptor matrix stacking and matching for different layers in the same dental object, for example the interior of the crown, post, and other features in the dental environment. Each time an indexing ray 216 intersects with the surface cross sectional boundary 222 of the mesh representing the crown, the distance that the ray travelled is stored in a 2-dimensional array matrix representing all rays extended and measured in the method. FIG. 5C illustrates a visualization map 210 of this array under the point cloud or mesh surface of the crown, shown as a heatmap of indexing ray distances travelled from the common centroid. The mapping of two particular indexing rays R1 and R2 is shown in dashed lines on visualization map 210, which indicate the distance of the outer surface of the crown to the common centroid 12 at the slicing plane 202 shown in FIG. 5B. The dark line in FIG. 5C shows the location of the slicing plane 202 shown in FIG. 5B and the locations in the slice where indexing rays are represented as their relative position in the 2D matrix. Using the distances represented by the indexing rays, a sampled point cloud representation of the original surface can be rebuilt as a 2D matrix from multiplying the rays by the stored distances, and the 2D matrix can be represented as a visualization map 210 as shown.

FIGS. 6A to 6C illustrate stages of obtaining slices of a tooth in a dental file segmentation single tooth description method, in accordance with some embodiments. Processing of three-dimensional single tooth files can be achieved from their native 3D format as created by a dental scanner and converted to a two-dimensional (2D) format. This can be achieved by slicing the three-dimensional tooth into an equally angled slicing plane and converting the slicing data into a matrix for 2D representation of the 3D dental object, as described. Preferably a graphical processing unit (GPU) is used to expedite the CAD design by processing the converted 2D matrixes in one or more GPU to accelerate and optimize processing for pattern matching. FIG. 6A illustrates an example of a dental object 200 in a native three-dimensional tooth file (e.g., STL mesh file format), obtained as a scanned image of a tooth from one or more dental scanner. The dental object 200 is shown with z-axis 212 which serves as the reference locus and preferably goes through the highest point, centre, or a high point on the tooth to ensure the data is generated and stored uniformly. Each mesh file has a bounding box, and the common centroid is generally assigned as on the z-axis at the center of that bounding box, or the bounding box can have the same z-axis as the volumetric centroid of the mesh file. The z-axis usually refers to the longest axis out of the potential axes, and it is through the z-axis that the dental feature to represent is aligned. Generally the z-axis will be assigned through a single tooth from the occlusal plane toward the jaw.

FIG. 6B is an image of the dental object shown in FIG. 6A viewed from the top through the z-axis. The slicing centroid 206 is preferably on the z-axis, but may also be in another location outside of or not explicitly on the z-axis. As shown in FIG. 6B, the dental object is analyzed by the indexed slicer where, in the present example method, the dental object is sliced radially into a plurality of radial portions 204 through the slicing centroid 206. In the embodiment shown, each radial slice will pass through the tooth centroid or z-axis. As shown in FIG. 6B, all radial slicing planes 202a, 202b, 202c, 202d, 202e that are generated preferably have a consistently increasing angle alpha ($\alpha$) such that the difference in angle or degrees from one radial slicing plane to the next is the same. Each radial slicing plane 202 will generate a cross-sectional view of the dental object 200 through the plane. The number of slices needed is selected to ensure that all features of the tooth or dental object are adequately captured by the 2D matrix descriptor method, as the number of radial slices determines the quality or resolution of the resulting matrix and the image provided by the visualization map. For example, if the number of slices are too few, then the space between slices may be large enough so that their cross-sections do not show an anomaly or feature of the anatomy. Increasing the number of radial slicing planes will increase the accuracy of the descriptor generation such that the resulting 2D matrix provides more granularity on the 3D shape of the dental object.

As shown in FIG. 6C, the distance from the indexing centroid 214 to the intersection of each cross-sectional point or tooth cross sectional boundary 222 on the circumference of the dental object slice, or the length of each indexing ray 216, may be measured by the radial encoder. The indexing centroid 214 is the assigned centroid of the cross-sectional plane of a single radial slicing plane generated from radial slicing of the dental object through a radial slicing plane and should be the common centroid if the encoding method is being used in a descriptor stack or compared with other matrixes. To encode the tooth image the radial encoder will generate a plurality of indexing rays 216 originating at the indexing centroid 214. The distance between the indexing centroid 214 and the circumference of the cross-section of the radial slicing plane at the edge of the dental object, referred to as the cross sectional boundary 222, can be generated from the slicing plane to map the circumference of the dental object in the slicing plane. In some embodiments, all the indexing rays will be equally angled in space at an angle beta ($\beta$) such that the angle between each indexing ray 216 is constant. It should be noted that the cross section created by the indexed slicer of the dental object from an indexing centroid 214 positioned at a bottom plane or at a large or infinite distance from the cross sectional boundary 222 can be used, resulting in a substantially infinite beta angle. Increasing the number of indexing rays generated will provide more detail about the dental object, for example the tooth anatomy, by capturing more data points around the tooth cross-section circumference. However, more circumferential data points as provided by the distances of the plurality of indexing rays will increase the 2D matrix file size, accordingly this should be kept in mind when determining the number of indexing rays required to provide adequate precision required for the desired purpose.

Figure 7:
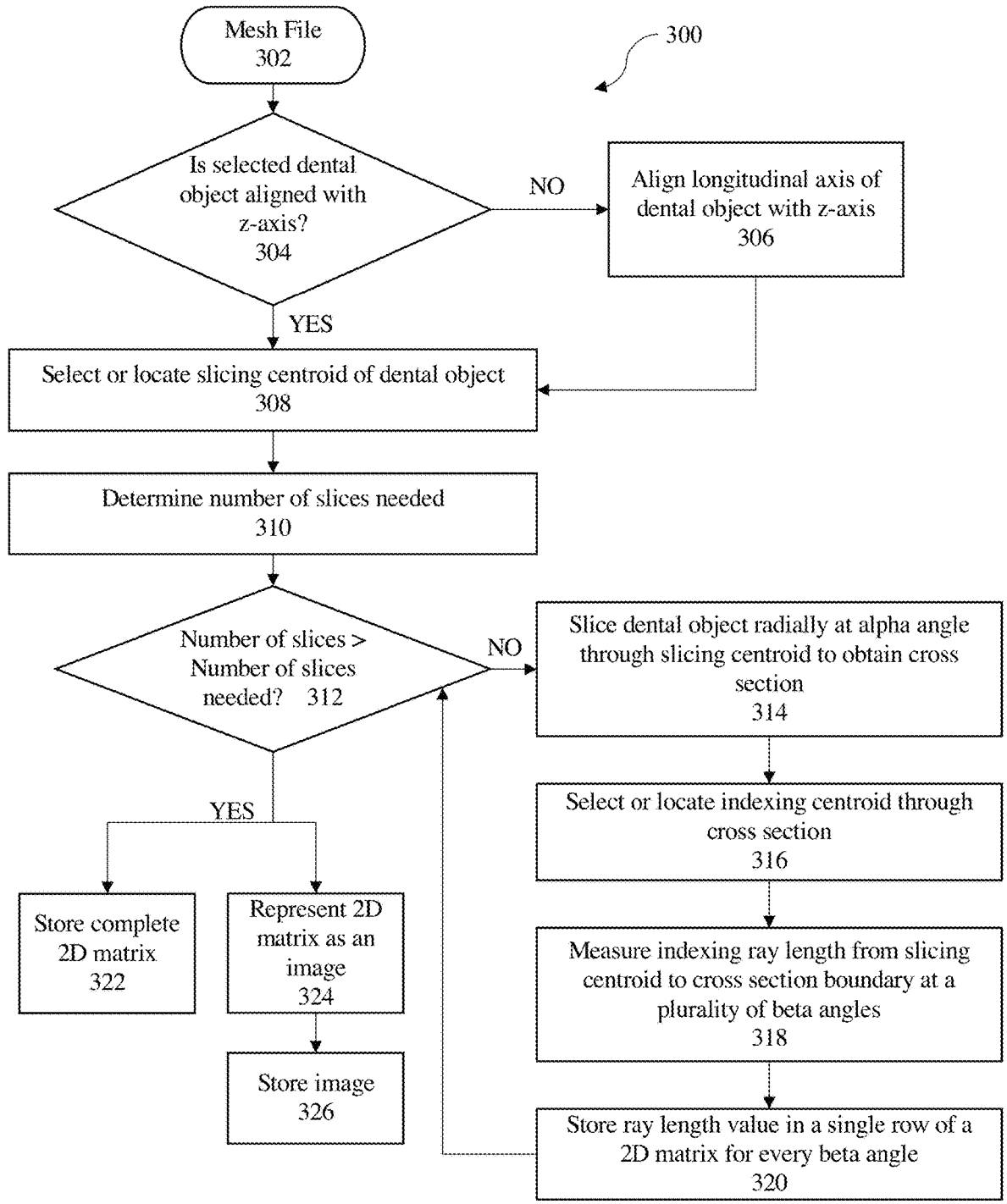
FIG. 7 is a flow chart of an example method of generating a single tooth descriptor.

FIG. 7 illustrates, in a flow chart, an example computational of a method of generating a single tooth or dental object descriptor 300, in accordance with some embodiments. The method of generating a single tooth descriptor 300 takes a 3D single tooth mesh file 302 (e.g., in an STL format) as an input. In some embodiments, the file may represent a dental object or dental anatomy such as a tooth as shown in FIG. 5A. In other embodiments, the file may represent a group of teeth that include the tooth for which the descriptor is generated, multiple teeth, dental arch, occlusal or bite pattern, soft tissue structures, or other dentition or dental structure. In some embodiments, the z-axis should be aligned with the anatomy's (e.g., object or tooth) longitudinal axis. The system queries whether the selected dental object is aligned with the z-axis 304. If the selected tooth is not aligned with the z-axis then the anatomy's longitudinal axis is aligned with the z-axis 306. In some embodiments, the system automatically aligns the dental anatomy's longitudinal axis to the z-axis. For example, the system may generate a transformation matrix which moves the center of a bounding box of the input STL to the origin. This aligns the dental anatomy's longitudinal axis aligned with the z-axis. The alignment with the z-axis may be performed to ensure the data is generated and stored uniformly. Once the anatomy or selected tooth is aligned with the z-axis, a slicing centroid, or the centroid of a group of teeth that includes the selected tooth, is located 308. Next, the number of slices needed to ensure that all features are covered is determined 310. For example, if the number of slices is too few, then the space between slices may be large enough so that the cross-sections provided by the plurality of slices does not show a particular anomaly or feature of the anatomy. The step of determining the number of slices through the slicing centroid 310 will determine the quality or granularity of the 2D matrix representation and resulting visualization map of the dental object or tooth. Next, if the number of slices created is not greater than the number of sliced needed 312, then the tooth or dental object may be sliced radially at an alpha angle as a plane normal in a clockwise or anti-clockwise direction with the slicing centroid as a plane origin 314. At this point, the process provides a cross-section view for each slice. To do this, the system locates or selects the indexing centroid 316 for each cross-section, and then measures the length of the indexing ray from that indexing centroid to the cross-section boundary 318 in a clockwise or anti-clockwise direction, preferably at an approximately equal beta angle. The measurements comprise indexing ray length values for each slice or slicing plane and can be stored as a single row unit 320. Steps 312 to 320 may be repeated in a loop to obtain single row units for each slice, which can then be stored in a 2D matrix 322 format one after another until a sufficient number of slices has been processed. The generated 2D matrix may also be stored in a data repository such as a matrix database. In some embodiments, the method for generating a single tooth or dental object descriptor may be performed for another tooth anatomy for example another incisor, molar, premolar three-dimensional teeth. The matrix obtained for each output of method may be stored in as a 2D matrix 322, optionally in a matrix database. This method also allows the storage of the plurality of created 2D matrices in an image format 324 or as a stored image 326, such as a visualization map. The image format or visualization map may be stored by, for example, representing the maximum and the minimum value in the matrix to a chosen color extreme values, representing an image file for that corresponding tooth matrix 324. It should be noted that the image visualization map file format is not limited to any single file format, which can include but is not limited to JPEG, GIF, PNG, TIFF, PSD, PDF, EPS, AI, INDD, RAW, etc. The 2D matrix, which can be represented as one or more image or visualization map images, can be stored 326 with the same method described above for the tooth database and can be linked with each other.

Figure 8:
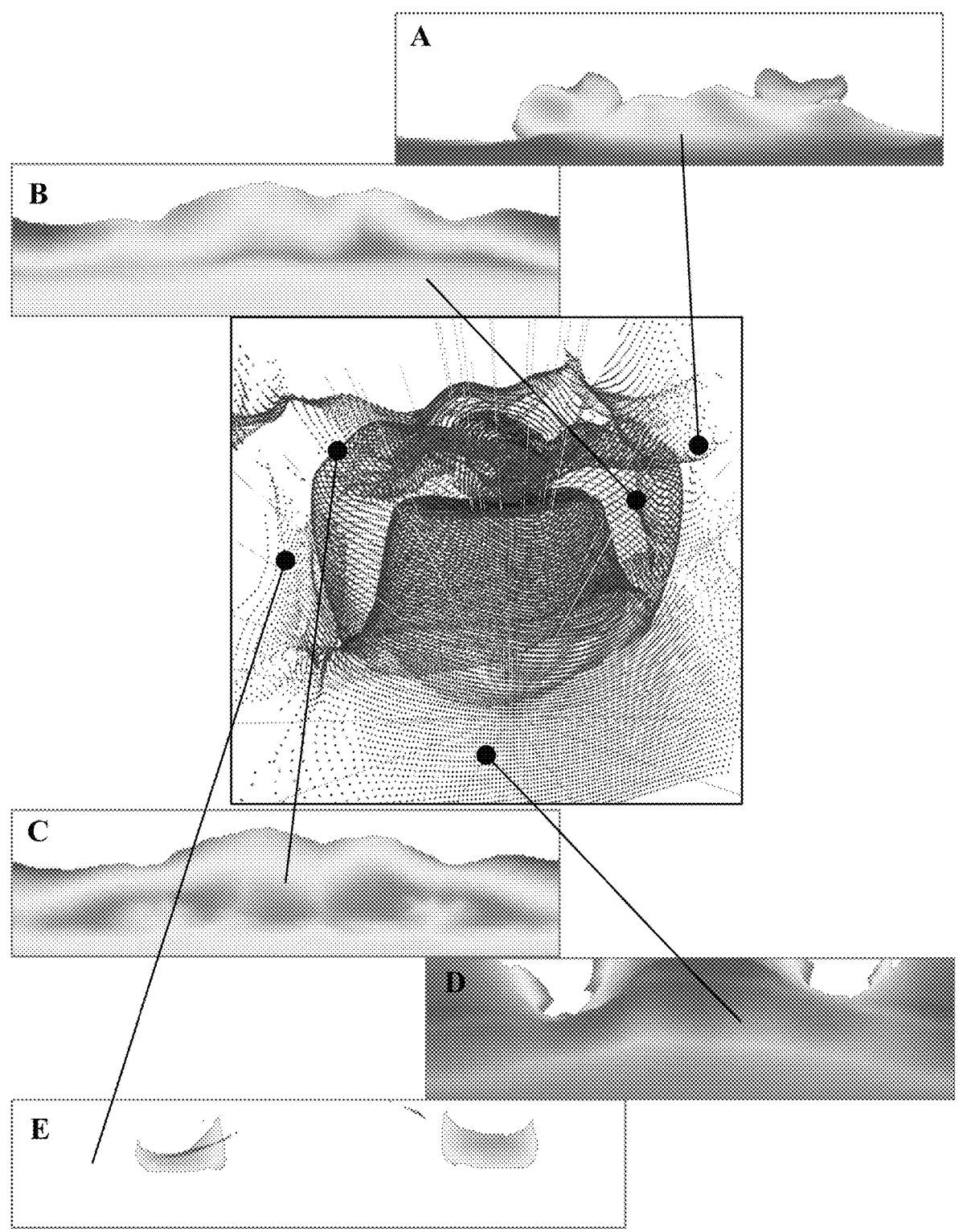
FIG. 8 illustrates a tooth object with multiple 2D matrixes recorded at different tooth object locations.

FIG. 8 illustrates a mesh image of a tooth object, specifically a multi-layer dental object molar comprising gum structure, prosthetic post, crown structure, top jaw occlusal surface, and dental environment with adjacent teeth. Each layer in the dental object is converted into a 2D matrix representation where each layer shares a common centroid such that the layers are stacked or anchored in space with respect to one another. To create the descriptor matrix stack in accordance with the present method, indexing rays are cast from the common reference locus using the radial encoder and multiple 2D matrixes are recorded at each different tooth object location or boundary surface. To create the multiple descriptor matrixes for a single tooth object, rays are cast from the reference locus and travel outwards from the centroid in all directions towards the outer surface of the triangulated mesh of the tooth object for each outer surface in the dental object. In addition to inner and outer surfaces of the triangulated mesh image of the tooth object, for example the inner and outer surfaces of a crown shown as visualization maps B and C respectively, there may be multiple additional surfaces that the ray can traverse. Each intersection of the indexing ray with a boundary surface results in a distance measurement from the centroid to that surface and is recorded in a 2D matrix corresponding to the specific boundary surface. With a dental tooth object some surfaces that can exist include but are not limited to, listed outward from the centroid, an outer post surface, an internal crown surface (B), an outer crown surface (C), an occlusal surface to neighbouring teeth (E), an opposite jaw occlusal surface (A), and a gum surface (D). Each of these surfaces can be described in a different 2D array and the arrays can be stacked based on distance from the common centroid, with the common centroid or reference locus aligning the arrays in space as they are related to the same dental object. A single ray from a common centroid can also intersect with or hit a triangulated mesh surface multiple times and record the distance travelled for each hit in a separate matrix for each surface intersection, for example when a common centroid is used in the case where there is an overhang, for example with a gum structure. All boundary intersections of the same order can be recorded in the same two-dimensional matrix, meaning the distance travelled to the first boundary intersection is recorded in the first matrix, and the distance travelled to the second boundary intersection is recorded in the second matrix, etc. In a case where there are multiple ray intersection points, such as in an overhang, a radial or parallel slicing method is preferably used instead of an angular indexing method. In this example, there are multiple overlapping mesh images in the scene, and the preparation scan comprises the gumline, post, and occlusal surfaces, and the unfitted fabricated crown. All mesh images are anchored at the same common centroid. When indexing rays intersect the inside surface of the crown this produces a 2-dimensional matrix describing the inside surface of the crown; the same indexing ray continues travelling and records a 2-dimensional matrix recording the distance to the outside surface of the same crown. The same process can be used, for example, in a dentist's scan of a surgical preparation site, where the first ray intersection describes the preparation site and the second ray intersection describes the adjacent tooth walls.

FIG. 9 illustrates a selection of tooth descriptor surfaces of a single tooth object described in relation to a common reference locus. This figure exhibits how each segmented feature corresponds to one 2-dimensional matrix of distances. Each 3D surface can be reconstructed with just the data encoded in the 2D matrix and represented as a unique 2D matrix which can be searched and matched in a matrix descriptor database. Each 2D matrix can also be converted into a visualization map, where, as shown: A is a mesh image of neighboring teeth to a dental object and its associated visualization map; B is a mesh image of a dental post and its associated visualization map; C is a mesh image of an internal crown surface and its associated visualization map; D is a mesh image of an external crown surface and its associated visualization map an outer crown surface; and E is a mesh image of an opposite jaw occlusal surface and its associated visualization map.

Figure 10:
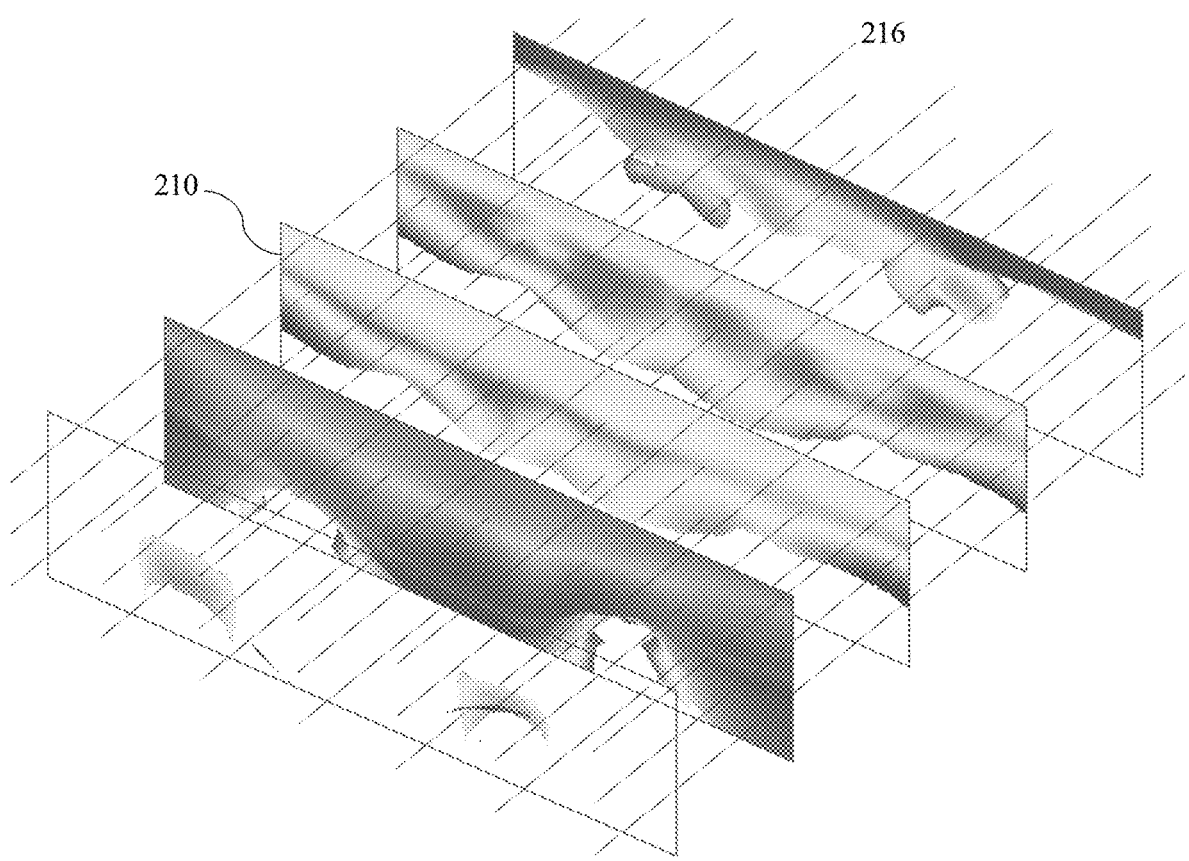
FIG. 10 illustrates a set of aligned two-dimensional tooth descriptor matrixes.

FIG. 10 illustrates the set of aligned two-dimensional tooth descriptor matrixes as shown in FIG. 9. Due to each pixel or cell in each descriptor matrix corresponding to the same indexing ray 216 and sharing a common reference locus, the visualization maps of all 2D descriptor matrices are aligned relative to each other. This figure exhibits that each cast indexing ray 216 intersects with the same array cell for each related visualization map 210 for every 2D descriptor matrix.

Figure 11:
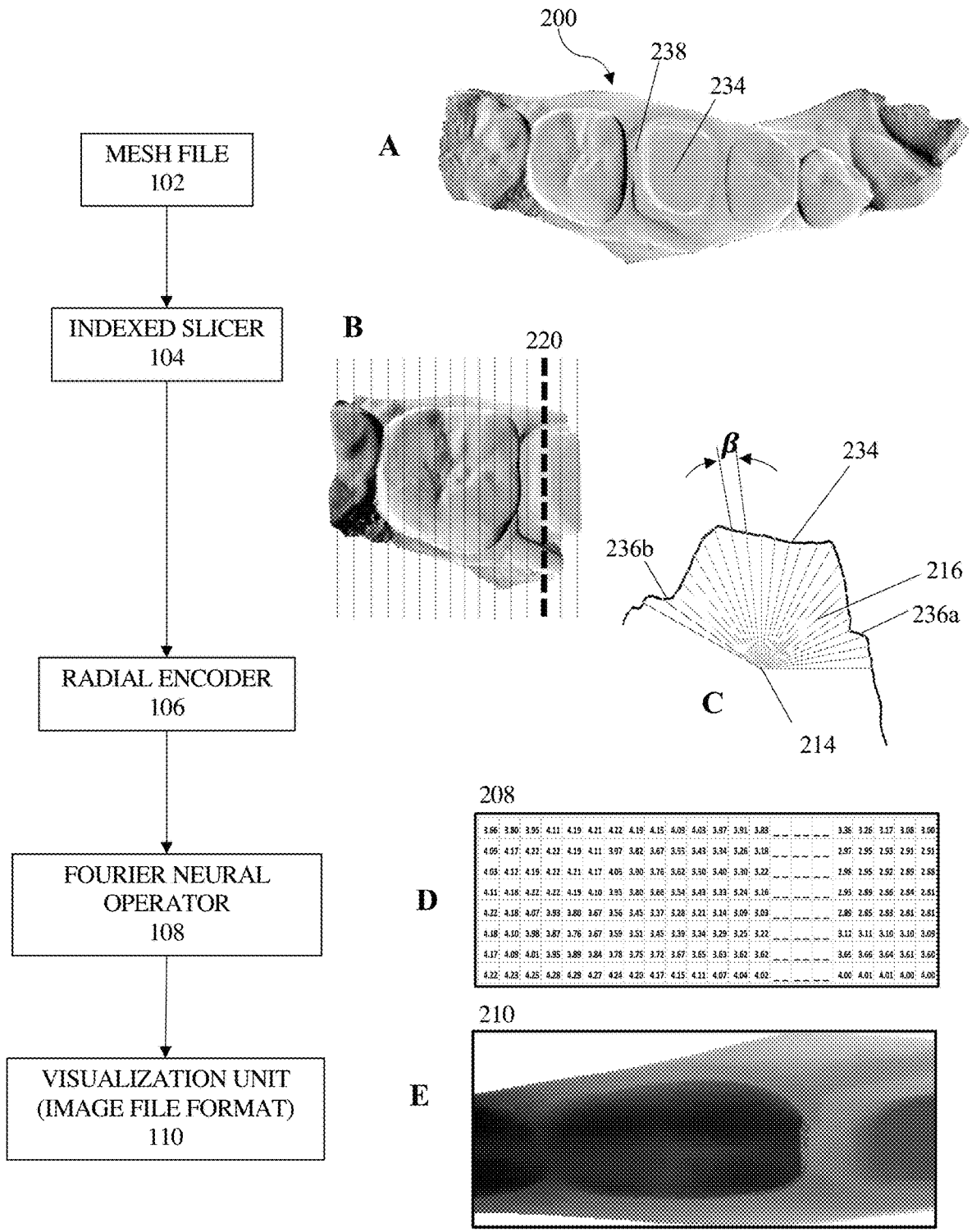
FIG. 11 illustrates examples outputs of components of the descriptor generation system employing an example of another single tooth description method.

FIG. 11 illustrates an example method of the descriptor generation system employing an example of another single tooth description method, in accordance with some embodiments. This method is related processing of three-dimensional single tooth files from their native 3D format to a 2D format. This method is different than the previously discussed method based on the input, which is a complete bitewing or plurality of teeth scanned as a group, and not just a single tooth. A group of teeth may be called a "bitewing" if it is three or four teeth together, or a quadrant if is almost half of a dental arch. The entirety of the upper or lower set of teeth may be called the "dental arch". Step A illustrates an example of a dental object 200 in a three-dimensional tooth anatomy in a mesh or STL file format 102. In this example, a quadrant of teeth is shown. In some embodiments, a tooth or teeth for which a descriptor is to be generated may be located in this anatomy. The image can be received by a scanner as a set of photogrammetry or camera images and converted into an STL file format, also referred to as a mesh file format, or may be scanned directly in an STL file format by a dental scanner. In some embodiments, a tooth or teeth for which a descriptor is to be generated may be located in this anatomy. The method shown can be utilized for the design of a crown, or fabricated crown, that can fit on post 234. Post 234 is the remainder of a tooth that has been shaved down during dentistry, and the present method is used to visualize the post and surrounding gum tissue as well as neighbouring teeth in order to design a suitable crown that will fit onto the post 234. As shown, gumline margin 238 around the post will be the seating surface for the final crown, and it is important that the crown edge, or crown margin, be designed to fit the gumline margin.

Step B illustrates an example of a portion of the three-dimensional quadrant that is cut by the indexed slicer 104 in such a manner that it shows one tooth and 25% of both of its adjacent teeth (without slicing planes). A single longitudinal slicing plane 220 is also shown. One way of slicing the 3D STL or mesh file is to locate a slicing centroid at an infinite distance away from the dental object, such that the slicing planes are substantially parallel. This is in contrast to the radial slicing planes when the slicing centroid is inside or near the 3D image of the dental object. Other indexed slicing techniques and methods may also be used with the slicing centroid at various locations relative to the dental object. For example, instead of slicing radially, the teeth may be sliced in a parallel manner or using angular indexing. As shown in Step B, all slices that will be generated are preferably approximately equally spaced and each slicing plane generates a cross-sectional view of that location of the dental object. The more slices there are, the better the accuracy that can be achieved however the more data will be generated as part of the 2D descriptor matrix that results.

Step C illustrates an example of a radial encoding of a cross section of a post 234 through a slicing plane, as described above. The indexing centroid location can be selected depending on what features of the dental object are desired for imaging or focusing on or on the selected array value mapping algorithm. The user can also have the freedom to select the index centroid, or the indexing centroid can be automatically selected by the system either by dental object shape, descriptor, or by the descriptor dental file segmentation algorithm. The distance from an indexing centroid 214 to an endpoint of an indexing ray 216 on a tooth perimeter in the slicing plane may be measured using a radial encoder 106. In some embodiments, the slicing centroid may be the same as the indexing centroid of the cross-section generated from the slicing plane. The radial encoder generates the indexing rays of segments in the slicing plane which maps the distance from the indexing centroid 214 to the circumference of the dental object cross-section generated from the slicing plane to the indexing centroid 214. In some embodiments, all the indexing ray 216 segments may be approximately equally angled in space, meaning that they are separated at the same angle, shown here as angle β. As an alternative, the common centroid can be at the intersection of the z-axis or central axis of a dental object and a reference plane normal to the central axis, and indexing rays can be extended normal to the indexing plane toward the dental object. Accordingly, the cross section created by the indexed slicer can also be measured from the bottom plane or below, for example, by placing the indexing centroid 214 at a large or infinite distance from the dental object circumference on the reference plane to provide essentially an infinite beta angle such that the indexing rays 216 are substantially parallel. The more indexing ray segments are generated, then the better details will be provided about the tooth anatomy and surface structure. However, file size should also be kept in mind with respect to how many ray segments are feasible. The sides of the margin or margin shoulders 236a, 236b are shown which provide geographical structure of the post and surrounding gum tissue such that the crown can be designed to securely but comfortably fit both the post 234 and the gum.

Step D illustrates an example of the output 2D matrix 208 of the Fourier neural operator 108 for the plane of the tooth, gum features, and post shown in A as a data set from each slicing plane. A Fourier neural operator 108 can generate a 2D matrix 208 from the radial encoding. Only the matrix values for each slicing plane is shown in 2D matrix 208 for ease of presentation. It should be understood that a full matrix may have many hundreds or thousands of rows and columns to provide sufficient granularity to describe the entire anatomy. In this example, the number of rows of 2D matrix 208 is equal to the number of slicing plane generated from the indexed slicer, and the number of columns is equal to the number of indexing rays generated in each slice by the radial encoder 106. Each element of the 2D matrix 208 represents the distance from the indexing centroid to the cross-section boundary of the dental object in that slicing plane. The output of the Fourier neural operator is the desired 2D matrix 208 which can further be used in stacking applications. At step E the matrix 208 is visualized and each entry in the matrix may be represented as a pixel value in a visualization mapping/image. An example of a visualization map 210 or matrix visualization image is shown using a black and white greyscale mapping. The visualization map 210 can be useful to dentists or lab technicians for further analysis. In particular, in the present case where the radial slicer sliced the dental objects in parallel slices, where the slicing centroid is effectively an infinite distance away and the slices are effective parallel, the resulting visualization map is discernable as a pixelated representation of the dental object in relief. In some embodiments, such visualization may be generated via a mapping of the values of the neural operator matrix to a rainbow color, black and white shading or greyscale, or any other color mapping methods. The minimum and maximum values of the 2D matrix may be identified and assigned to the selected color map value extreme points. The values in the 2D matrix are represented as shading shown in each slicing plane. Again, a full matrix would correspond to the entire visualization mapping/image such that each conversion of a matrix entry to a colour/shading may be represented as a pixel in the visualization map 210.

Figure 12:
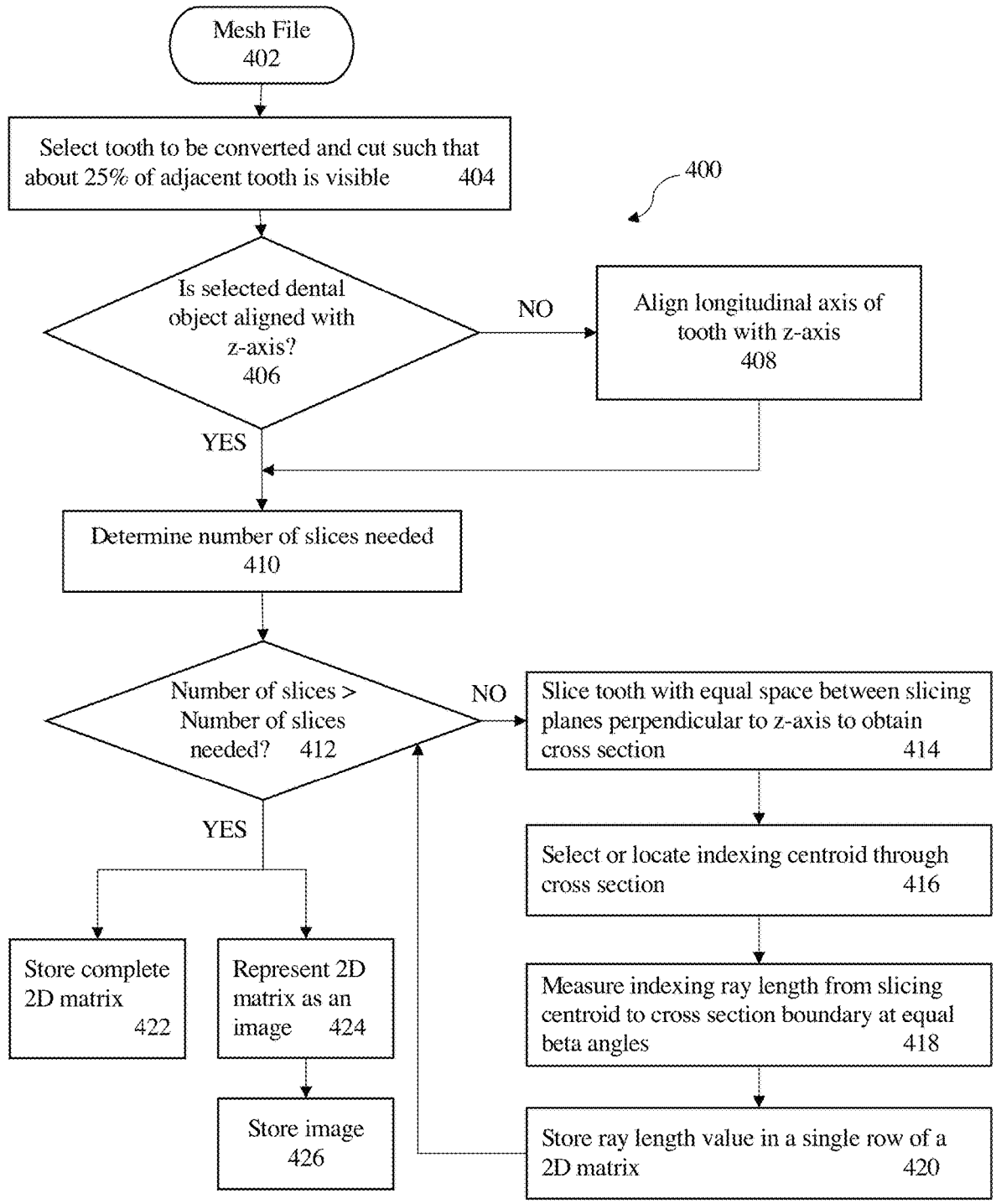
FIG. 12 illustrates, in a flow chart, another example of a method of generating a single tooth descriptor.

FIG. 12 illustrates, in a flow chart, another example of a method of generating a single tooth or dental object descriptor 400, in accordance with some embodiments. The method begins with taking a three-dimensional (3D) single tooth file in an STL format 402 as an input, either as a raw STL or mesh file from a dental scanner or as an STL or mesh file created from a different type of scan, such as a visual scan or mosaic of images, video, or photographs. In some embodiments, the file may represent an object or anatomy such as a tooth crown as shown in FIG. 11 in image A. In other embodiments, the file may represent a group of teeth that include the tooth for which the descriptor matrix is generated. Next, the targeted tooth is selected in 404. Preferably, a z-axis is aligned with the anatomy's (e.g., object or tooth) longitudinal axis. In some embodiments, the selected toot is converted and isolated from the quadrant in a manner where 25% of the adjacent teeth are visible. The system then queries whether the longitudinal axis of the selected tooth is aligned with a z-axis 406. If the z-axis is not aligned, then the anatomy (e.g., tooth) is aligned with the z-axis 408. In some embodiments, the system automatically aligns the dental anatomy's longitudinal axis to the z-axis. For example, the system may generate a transformation matrix which moves the center of a bounding box of the input STL or mesh file to the origin to align the dental anatomy's longitudinal axis with the z-axis. The number of slices needed to ensure all features are covered is then determined 410. For example, if the number of slices is too few, then the space between slices may be large enough so that their cross-sections do not show an anomaly or feature of the anatomy. This step will determine the quality of the 2D matrix and the resulting image or visualization map. The method may now go into a loop based on condition 412 such that the number of slices obtained is equal or greater to the number of slices needed. If the number of slices is not greater than the number of slices needed 412 then the tooth is sliced at approximately equal spacing, as a plane normal to the z-axis 414, for example in left to right direction, to obtain a cross-section view for each slice. It should be noted that the slicing can be from right to left as long as all teeth are sliced consistently in the same manner (i.e., always from left to right, or from right to left). Next, a slicing centroid is selected or located 416 for each cross-section, and the radial lengths between the slicing centroid and a cross-section boundary point are measured 418. It should be noted that the same features can be obtained in a clockwise or with an anti-clockwise direction, with the only resulting difference being that the resulting matrix will be in opposite direction as compared to one obtained from clockwise direction at an approximately equal beta angle. Performing the same algorithm with the same alpha and beta angles, including the same number of slices and rays, creates a normalized value map for the 2D matrix to enable descriptor comparison across many different dental objects such as in a machine learning model. The output ray length values for a slice are measured 418, and the ray length values are stored as a single row unit 420 in a 2D matrix. By running this loop (steps 412 to 420) a single row unit for each slice can be obtained and stored in the 2D matrix format one after another. The complete 2D matrix comprising all of the ray lengths and locational attributes on the dental object may then be stored in the matrix database 422. The method may then be performed for another part of the tooth or dental object anatomy, for example another targeted incisor, molar, or premolar three-dimensional teeth, interior crown surface, post, or other dental feature. The matrix obtained for each output of method 400 may be stored in the matrix database 422, where each dental feature or surface is stored in a different descriptor matrix. Each 2D matrix may also be stored in an image format 424 as a visualization map, which may be generated by representing the maximum and the minimum values in the 2D matrix to chosen color or hue extreme values and saving an image file 426 corresponding to the tooth matrix. The image file format is not limited to any single file format and can be stored in an image repository. One or more of the tooth or dental object database and the descriptor database may also be linked with the image repository, and multiple related descriptor matrixes may also be stored in a linked format to indicate their relationship to one another.

Figure 13A:
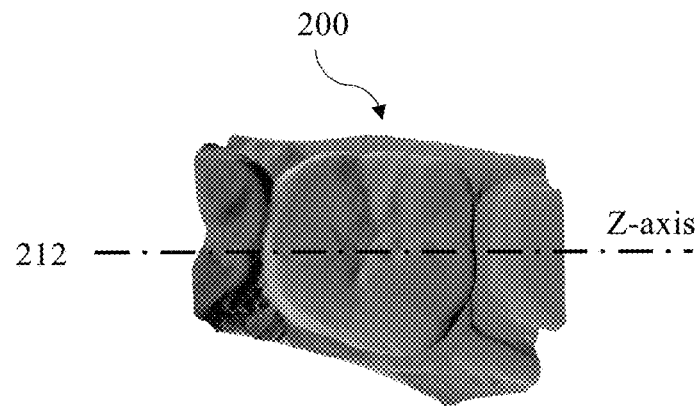
FIG. 13A illustrates the alignment of a dental object with a single tooth and adjacent teeth along a z-axis.
Figure 13B:
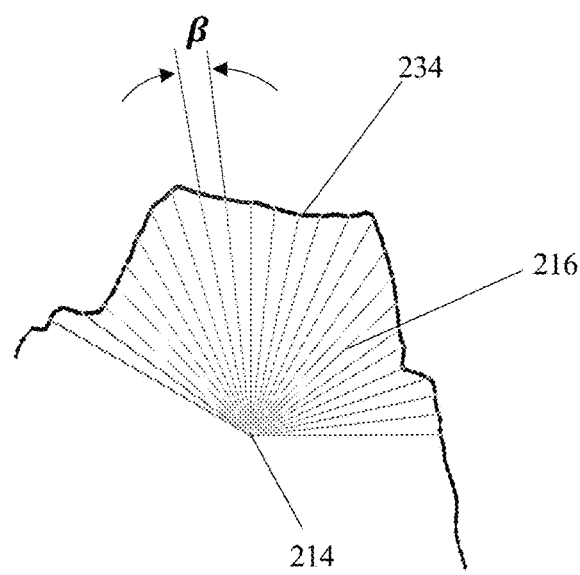
FIG. 13B illustrates the indexing of one cross section plane of a tooth at a near indexing centroid.
Figure 13C:
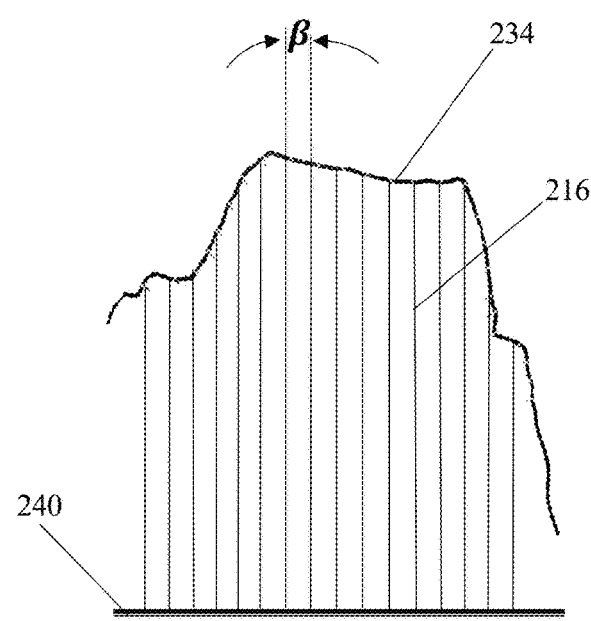
FIG. 13C illustrates the indexing of one cross section plane of a tooth at a far indexing centroid.

FIGS. 13A-C illustrate stages of obtaining slices of a tooth, in accordance with some embodiments. FIG. 13A illustrates an example z-axis 212 position for the dental object 200 and the alignment of the dental object. Aligning the anatomy's axis to the z-axis helps ensure that the data is collected and stored uniformly. When the teeth are sliced in parallel each slicing can be arranged normal to the z-axis with the indexing reference locus placed at a reference location relative to the intersection of the z-axis and each slicing plane. Accordingly the z-axis can serve as a common reference locus for each slicing plane and there is no need to locate a single common centroid for the dental object as a whole. FIG. 13B illustrates the indexing of one cross section plane of a crown post 234 at a near indexing centroid 214 with a plurality of indexing measurements taken at indexing rays 216 from a near indexing centroid on the slicing plane to the tooth cross sectional boundary at a plurality of beta ($\beta$) angles.

FIG. 13C illustrates the indexing of one cross section plane of a crown post 234 at a far indexing centroid serving as the reference locus. In this method each slicing plane is processed by an indexing centroid positioned at a relatively infinite distance from the dental object inside a bounding box. By positioning the indexing centroid far from the tooth or dental object at an effectively infinite beta angle the indexing rays 216 defined by from the indexing centroid to the cross sectional boundary of the dental object in the slicing plane will be substantially parallel and the array value mapping can be done from the bottom of the bounding box. In addition, the length of the indexing rays will be longer than if the centroid is closer to the tooth or dental object, however the distances can be normalized for processing using a Fourier neural operator or other normalization procedure. As such, instead of slicing radially, the teeth or post 234, for example, may be sliced in a parallel manner as shown, and the ray length distances can be recorded in the 2D matrix as starting from the bottom of the bounding box or at a reference plane 240. Other ways that can be used change the centroid position target the different dental anatomy features like margin, occlusal plane, etc. Preferably all substantially parallel slices that are generated will be approximately equally spaced to provide consistency and continuity across the resulting 2D matrix representations of the tooth or dental object. The more slices are done then the better the accuracy of the 2D matrix that can be achieved, however the more data is collected, as each slicing plane generates its own unique cross-section view and results in an individual row in the matrix. As such, the algorithm is tailored to provide a balance between data file size and surface feature granularity and accuracy. If the dental object or anatomy is sliced in parallel, there is no need to locate a teeth centroid and the z-axis can serve as the reference locus. However, consistency in parallel slicing with regard to distance between slicing planes is preferred such that the dental file segmentation algorithm used is consistent across dental objects having the same descriptor classification so that similar dental anatomy can be compared.

Figure 14:
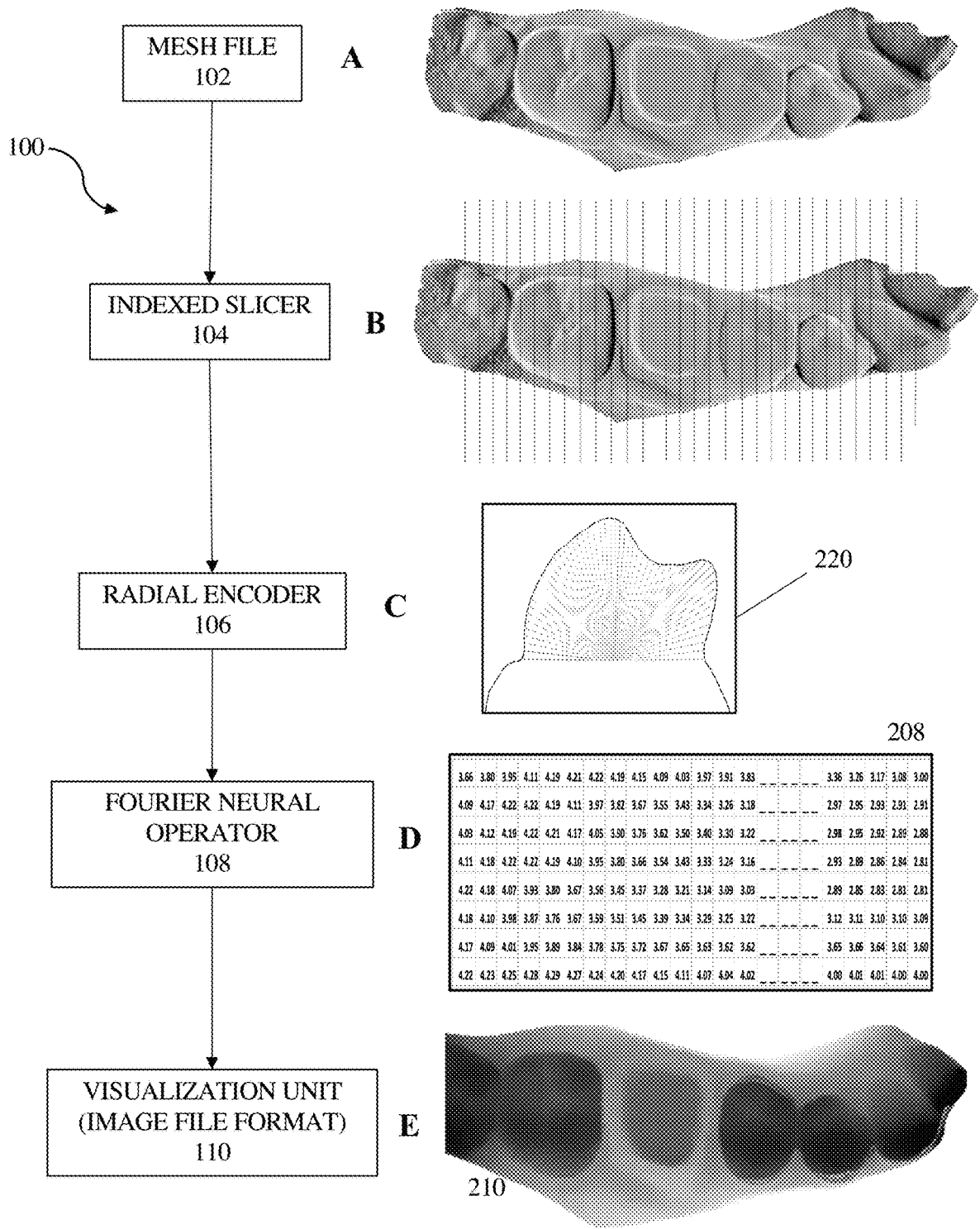
FIG. 14 illustrates an examples outputs of components of the descriptor generation system employing an example of an arch description method.

FIG. 14 illustrates example outputs of components of the descriptor generation system 100 employing an example of an arch description method, in accordance with some embodiments. This method is related processing of a three-dimensional dental arch file from its native 3D format to a 2D format. The term "bitewing" is generally used if the dental object is three to five teeth together, and the term "quadrant" can be used if the dental object is half or almost half of the dental arch. The same notation applies to both upper and lower anatomy. Step A illustrates the quadrant in an STL or mesh file format 102. This method is similar to the previously discussed method single teeth descriptor method as the methods both slice the dental anatomy in parallel. As shown in Step B, all slices generated by the indexed slicer 104 that will be generated are approximately equally spaced, and an increase in the number of slices or slicing planes improves accuracy. Each slicing plane will generate a cross-section view, and the distance from a slicing centroid to endpoints of the perimeter of the cross-section view are measured by the radial encoder 106. The slicing centroid is the centroid of the cross-section generated from the slicing plane. The radial encoder 106 will generate the ray segments which maps the distance of the cross-section generated from the slicing plane to the slicing centroid. In some embodiments, all ray segments will be approximately equally angled in space. It should be noted here that the cross section created by the indexed slicer 104 can also be measured from the bottom plane as the anchor point, in other words the beta angle can be effectively infinite. The higher the number of ray segments that are generated, the better the details about the tooth anatomy will be. However, file size requirements may result is limiting the number of ray segments. Step C illustrates an example of the radial encoding as described above. A slicing plane 220 is also shown, which is a single slicing plane through the dental object which is parallel or substantially parallel to the other slicing planes through the dental object. This method is similar to the previously discussed method of a single tooth descriptor method as the methods both slice the dental anatomy in parallel. Each longitudinal slicing plane 220 will generate a cross-sectional view of the dental object. The radial encoder encodes the cross section of the dental object in the slicing plane as indexing ray lengths from an indexing centroid. In Step D a descriptor matrix 208 is generated from the radial encoding by the Fourier neural operator 108. An example of the Fourier neural operator 108 for the bitewing shown in step B is shown as descriptor matrix 208. Only some of the matrix values for the portion of the bitewing in B is shown in descriptor matrix 208 for ease of presentation. It should be understood that a full matrix may have many rows and columns to provide sufficient granularity for the entire anatomy. Each entry in the matrix may be used as a pixel value to create a visualization map 210 using a visualization unit 110 as shown in E to assist dentists and/or lab technicians for further analysis. The descriptor matrix 208 can also be visualized and values of the Neural operator descriptor matrix 208 may be mapped to rainbow colour, black and white shading, or any other colour mapping method In some embodiments, the number of rows is equal to the number of slicing planes generated by the indexed slicer 104, and the number of columns is equal to the number of ray lengths generated in each slice by the radial encoder 106. Each element of the matrix represents the distance from the slicing centroid to the cross-section boundary of that slice. The output of the Fourier neural operator 108 is the descriptor matrix 208 which can further be used in stacking applications described below. The values in descriptor matrix 208 are represented as shading shown in visualization map 210. A full descriptor matrix would correspond to the entire visualization mapping/image such that each conversion of a matrix entry to a colour/shading may be represented as a pixel in the visualization map 210 image.

Figure 15:
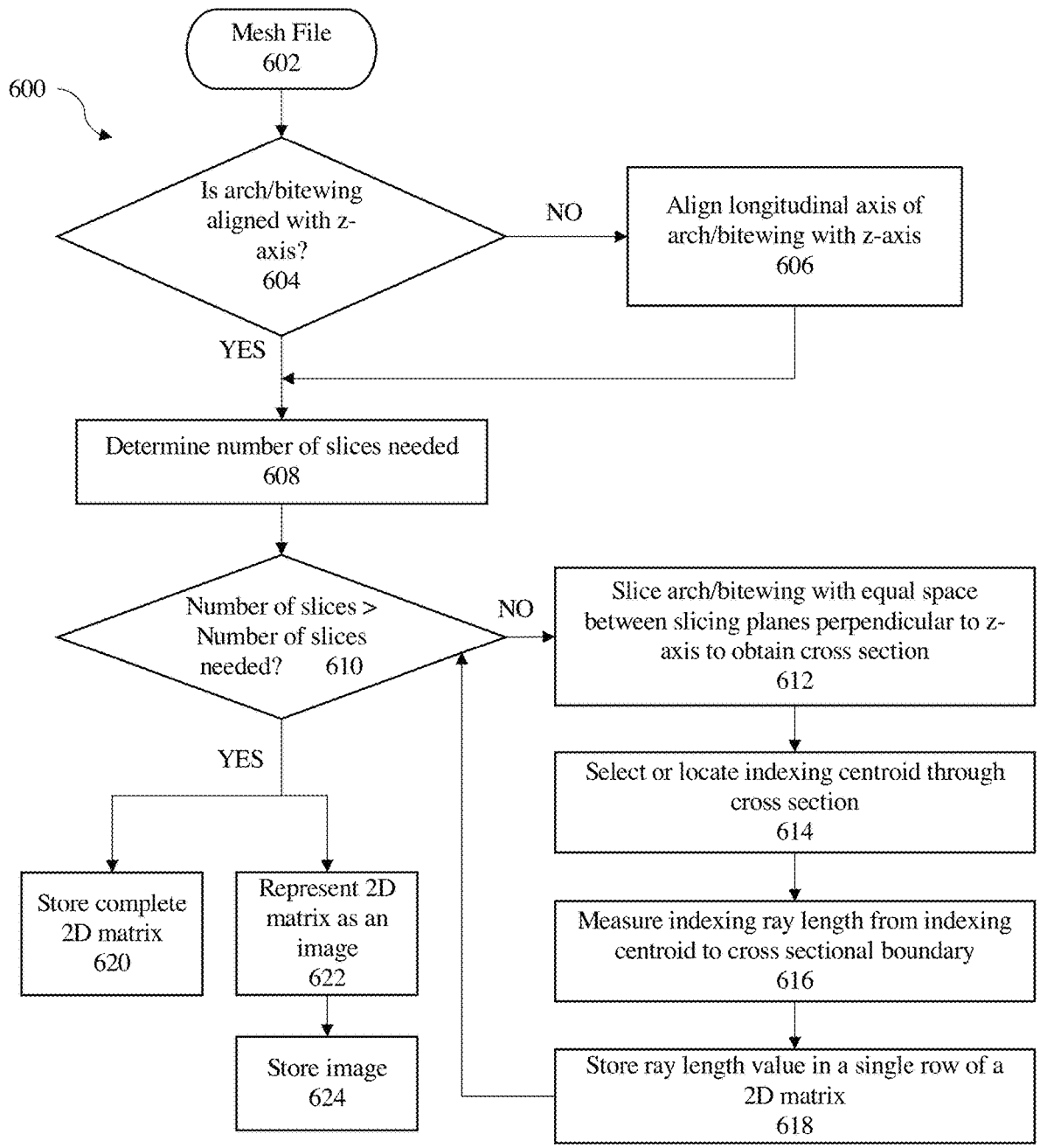
FIG. 15 illustrates, in a flowchart, an example of a method of generating a dental arch descriptor.

FIG. 15 illustrates, in a flowchart, an example of a method of generating a dental arch descriptor 600, in accordance with some embodiments. The method 600 begins by taking a three-dimensional quadrant file 602 as an input. The mesh file 602 representing a quadrant, arch, or bitewing, is a triangulated representative of the image of the quadrant file. The system queries whether the arch or bitewing is aligned with the z-axis of the image 604, and if not, the z-axis of the mesh file is aligned with the anatomy's longitudinal axis 606. In some embodiments, the system automatically aligns the dental anatomy's longitudinal axis to the z-axis. For example, the system may generate a transformation matrix which moves the center of a bounding box of the input STL or mesh file 602 to the origin. This aligns the dental anatomy's longitudinal axis with the z-axis 606. The number of slices needed to make sure all features are covered is determined 608. For example, if the number of slices are too few, then the space between slices may be large enough so that their cross-sections do not show an anomaly or feature of the anatomy. This step of determining the number of required slicing planes 608 determines the quality of the 2D matrix datafile produced by the method, and its accuracy relative to the original image file of the dental object. A recursive loop is then entered based recursive slicing the dental object, here an arch or bitewing, along a plurality of slicing planes, each slicing plane having an incremental distance to the next slicing plane, until the number of slicing planes or slices reaches the desired number. If the number of slices is not greater than the number of slices needed 610 then the arch or bitewing is sliced at approximately equal spacing, as a plane normal to the z-axis 612 to obtain a cross-section view for each slice. In this example, the arch or bitewing is sliced with equal space between slicing planes perpendicular to z-axis to obtain a cross section 612. The slicing operation can go from left to right, right to left, or in any other reasonable direction through the dental object. One reason for standardizing the slicing algorithm for a particular class of dental descriptors is to provide a basis for comparison of the resulting 2D descriptor matrix to other 2D descriptor matrices with the same descriptor in a descriptor database. Next, for each slicing plane, an indexing centroid is selected or located for each cross-section 614, and for each cross-section or slice, a plurality of indexing rays are assigned from the indexing centroid to the cross-sectional boundary of the slicing plane, and each indexed ray length is measured from the indexing centroid to the cross sectional boundary 616. The radial or indexing ray lengths between the indexing centroid and a cross-sectional boundary point on the slicing plane are measured in a clockwise or anti-clockwise direction, with an increasing beta angle between each indexing ray. It should be noted that the same features can be obtained with the anti-clockwise direction as a clockwise direction; the only difference is it will be in opposite direction as compared to one obtained from clockwise direction, at an approximately equal beta angle. As previously mentioned, standardization of the algorithm for converting the dental object into a 2D matrix file enables easier comparison and matching between 2D matrix files in the same descriptor class. The output measured ray length values for each slicing plane can then be stored as a single row unit 618 in a 2D descriptor matrix. By running this loop (steps 610 to 618) single row units for each slice can be obtained and stored in the 2D descriptor matrix datafile format one after another. This resulting 2D descriptor matrix may be stored 620 for example in a matrix database with other 2D matrices of dental objects. The same or similar method of generating a 2D matrix descriptor of a dental object may be performed for any another tooth anatomy or dental object, for example a single tooth such as a targeted incisor, molar, or premolar three-dimensional teeth. The 2D matrix may be visualized or converted into an image 622, for example by setting color or hue values for each range of numerical indexing ray length values, and the same can be stored 624 in an image file format. A visualization or image representation of the 2D matrix may be generated, for example, by representing the maximum and the minimum values in the 2D matrix to chosen color or shading extreme values and saving the image file corresponding to the 2D matrix of the dental object. The image file format is not limited to any single file format and can be stored in an image repository, which can be in the same or different location as where the related 2D matrix is stored. The dental object database may also be linked with or connected to the image repository.

Figure 16A:
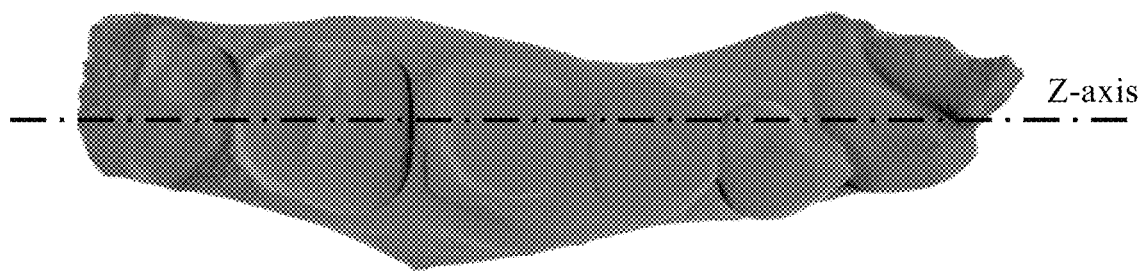
FIG. 16A illustrates an example of the z-axis position of a bitewing with crown post.
Figure 16B:
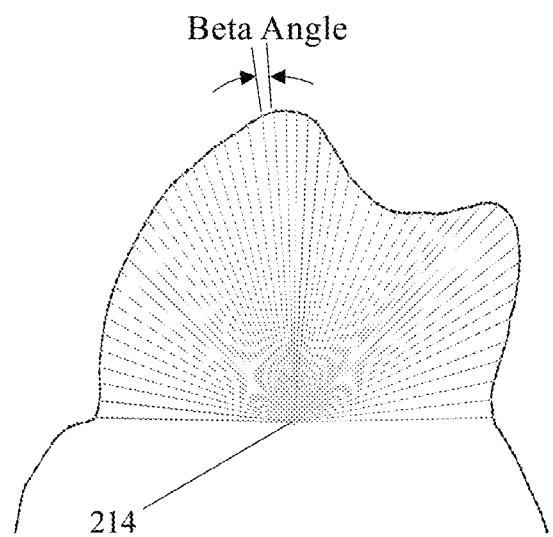
FIG. 16B illustrates a single slicing plane through a tooth.

FIGS. 16A and 16B illustrate stages of obtaining slices of a dental arch, in accordance with some embodiments. FIG. 16A illustrates an example of the z-axis position of a bitewing with crown post. The alignment of the z-axis is performed to ensure the data is generated and stored uniformly. As the anatomy is sliced in parallel, there is no need to locate a teeth centroid for the bitewing as a whole. FIG. 16B illustrates a single slicing plane through a tooth with the indexing centroid 214 positioned inside the dental object and a plurality of indexing rays separated at a consistent beta angle.

Figure 17:
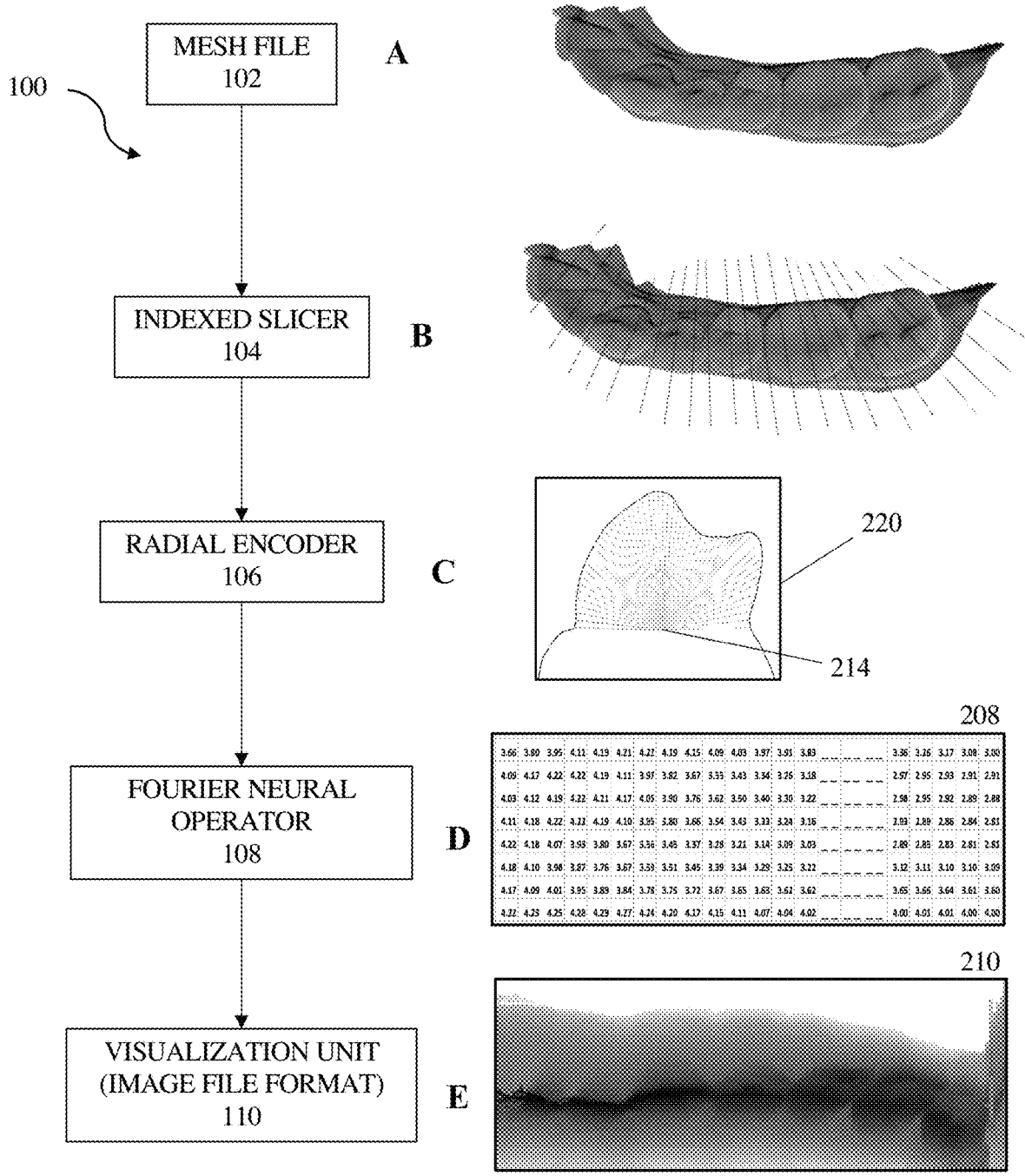
FIG. 17 illustrates an example output of components of the descriptor generation system employing another example of an arch description method.

FIG. 17 illustrates an example descriptor generation system 100 employing another embodiment of an arch description method, in accordance with some embodiments. The reference locus for slicing this bitewing in descriptor generation is a common centroid which is peripheral to the bitewing. One particular use case for this method is in a bite pattern recognition and analysis which does not require a common centroid anchoring multiple embedded descriptor matrixes, such as with crown design. In a bite analysis a mesh file 102 is obtained using, for example, occlusal radiography, where the upper and lower bitewings are images in relation to one another and a single mesh file 102 is recreated which has the top and lower bitewings positioned as they would be during an occlusal interaction. This method is related processing of a three-dimensional dental arch file from its native 3D format to a 2D format. This method can also function with different dental anatomies such as a bitewing or a quadrant. Step A illustrates an example of a quadrant dental object in a mesh or STL file format. Step B illustrates a quadrant or dental object which has been passed through an indexed slicer 104. In this case, it is sliced radially to produce a plurality of slicing planes 202. In this embodiment each slicing plane 220 passes through an arch centroid, which in this case is outside and at a distance from the dental object. Each slicing plane 220 generated by the indexed slicer is at an approximately equal angle to the next slicing plane. Increasing the number of slices increases the accuracy. Step C shows a single slicing plane 220 and dental object cross sectional boundary. Each slicing plane will generate a cross-sectional view, and the distance from an indexing centroid 214 to endpoints of the perimeter of the cross-section view, or the cross sectional boundary 222, are measured by radial encoder 106. The indexing centroid 214 can be considered to be the centroid of the cross-section generated from the slicing plane, however the indexing centroid can be anywhere inside or outside the dental object, providing that indexing of each indexing ray is assigned relative to the selected indexing centroid and cross sectional boundary 222. The radial encoder 106 will generate the ray segments which maps the distance from the cross sectional boundary of the dental object in the slicing plane 220 to the indexing centroid. In some embodiments, all ray segments will be approximately equally angled in space, meaning that the angle between each indexing ray is constant, however this is not necessary as previously described. In particular, the cross section created by the indexed slicer can also be measured from a bottom plane or indexing plane at a distance away from the slicing plane to provide a substantially infinite beta angle. The greater the number of indexing ray segments that are generated, the better the details about the tooth or dental object anatomy will be, however, file size requirements may result in limiting the number of indexing ray segments. The greater the number of ray segments that are generated, the better the details about the tooth anatomy will be, however file size requirements may result in limiting the number of ray segments, and standardization of the dental file segmentation algorithm across all patients facilitates matching of similar matrixes in the descriptor database.

Step D is an example of an output 2D descriptor matrix 208 of the Fourier neural operator for the portion of the dental object shown in B. The 2D descriptor matrix 208 may be generated from the radial encoding by the Fourier neural operator 108. Only the matrix values for the matrix portion shown in the visualization map 210 is shown in 2D descriptor matrix 208 for ease of presentation. It should be understood that a full matrix may have many rows and columns, on the order of hundreds or thousands, to provide sufficient granularity for the entire dental object anatomy. The output of the Fourier neural operator 108 is the descriptor matrix 208 which can further be used in stacking applications where multiple descriptor matrixes are anchored in space. Step E illustrates an example of a matrix visualization using black/white greyscale mapping to provide a visualization map 210. Each entry in the matrix may be used as a pixel value in a visualization map 210 shown on visualization unit 110. In some embodiments, the number of rows is equal to the number of slicing planes generated by the indexed slicer 104, and the number of columns is equal to the number of ray lengths generated in each slice by the radial encoder 106. Each element of the matrix represents the distance from the slicing centroid to the cross-section boundary of that slice. The values in each descriptor matrix may be mapped to rainbow colour, black and white shading, or any other colour mapping method. The minimum and maximum values of the 2D matrix may be identified and assigned to the selected colour map value extreme points to generate the colour map. The values in the 2D matrix are represented as shading shown in matrix portion 224. A full matrix would correspond to the entire visualization mapping/image such that each conversion of a matrix entry to a colour/shading may be represented as a pixel in the visualization map 210.

FIGS. 18A to 18C illustrate stages of obtaining slices of a dental arch, in accordance with some embodiments. FIG. 18A illustrates an example of the z-axis position for a quadrant in a dental arch. The alignment of the z-axis is performed to ensure the data is generated and stored uniformly. Next, arch centroid 226 is located or selected. Each mesh file has a bounding box, and the slicing centroid is preferably set as the volumetric centre of the bounding box. Alternatively, the slicing centroid can be assigned as the same as the volumetric centroid of the mesh file. In an arch description method, the arch centroid is preferably assigned as the volumetric centroid of the full dental arch. Selecting the slicing centroid in this way allows the comparison with similar full dental arches, which also have the same descriptor classification. FIG. 18B illustrates planar slices of the dental arch where each slice intersects with the arch centroid. The number of slices and slicing planes 220 needed to ensure all features are covered is determined to provide the data density required for characterizing the dental arch. For example, if the number of slices is too few, then the space between slices may be large enough so that their cross-sections do not show an anomaly or feature of the anatomy that is desired for visualization and modeling. This step will determine the quality and size of the matrix and the resulting quality and density of the image or visualization map. If the number of slices is not greater than the number of slices needed then the arch is sliced radially at an approximately equal alpha (α) angle, as a plane normal in a clockwise direction with the arch centroid as a plane origin to obtain a cross-section view for each slice. It should be noted that the slicing can be, for example, from right to left or from left, as long as all teeth are sliced consistently in the same manner or direction (i.e., always from left to right, or from right to left) in accordance with a dental file segmentation algorithm defining the slicing methodology and distances such that the resulting matrix values and array value mapping is comparable for similar dental anatomy in with the same descriptor classification.

FIG. 18C shows a single slicing plane and dental object cross sectional boundary. An indexing centroid 214 is located for each cross-section, and the radial encoder divides the plane with a plurality of indexing ray. Each indexing ray has a radial length measured between the indexing centroid 214 and a cross-section boundary 222. The indexing rays can be assigned in a clockwise direction from a first indexing ray, or in an anti-clockwise direction. The beta angle between indexing rays can be approximately equal, or it can vary based on the area of the dental object that required the highest resolution. An output 2D matrix of the Fourier neural operator can be generated for the dental object. An output ray length value for each indexing ray the slicing plane is provided, and the values can be stored as a single row unit in a 2D matrix. The 2D matrix obtained can be stored in the matrix database. The matrix may also be stored in an image format. A visualization map may also be generated by representing the maximum and the minimum values in the matrix to chosen color extreme values and saving an image file corresponding to the tooth matrix. The image file format is not limited to any single file format and can be stored in a repository. The tooth database may also be linked with the image repository.

Figure 19:
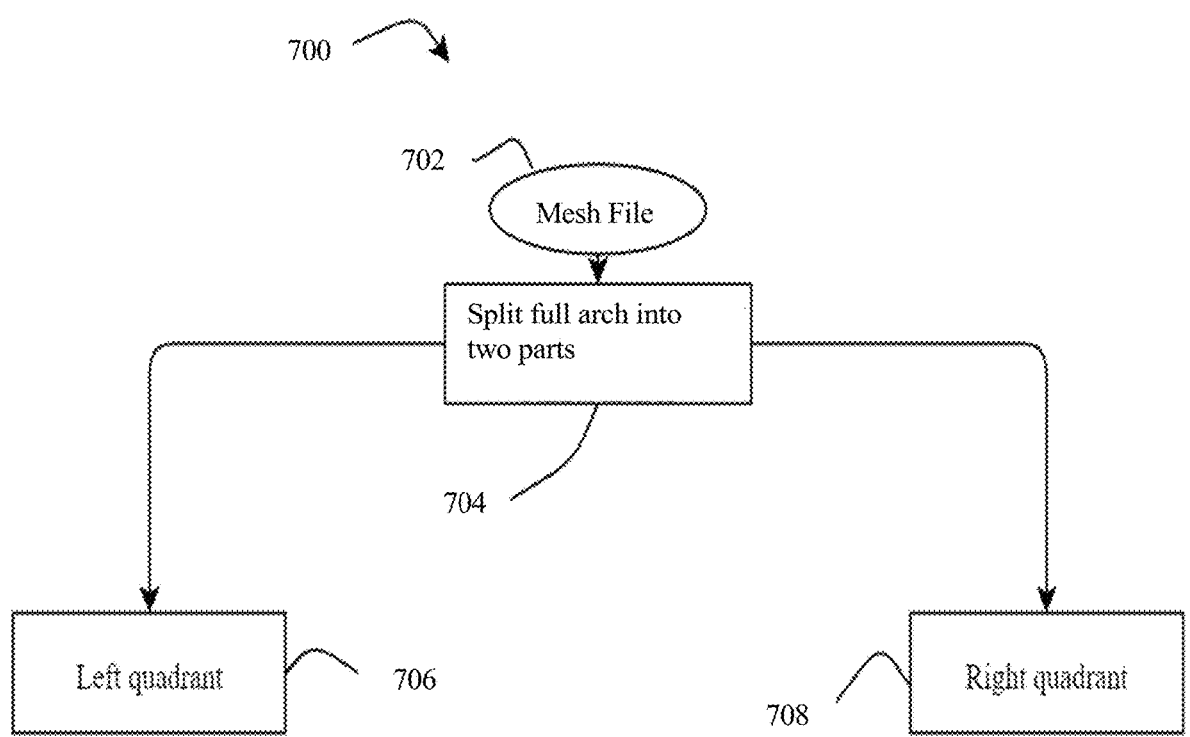
FIG. 19 illustrates a flowchart of an example method of generating a full arch descriptor.

FIG. 19 illustrates, in a flowchart, an example of a method of generating a full arch descriptor 700, in accordance with some embodiments. This method of generating a full arch descriptor 700 employs an arch descriptor method as described above. In use the method starts with an STL or mesh file 702 of a full dental arch. The full arch is split into two parts 704, preferably around the central incisor. This gives two different quadrants, namely left quadrant 706 and right quadrant 708 as per where the quadrant is located. Each of the left quadrant 706 and right quadrant 708 can be treated as a separate independent quadrant, and an arch descriptor method may be applied to each of the two quadrants to obtain one or more 2D descriptor matrix and/or visualization map of the full arch or subset thereof, depending upon the method selected.

FIG. 20A illustrates an example of a full arch, in accordance with some embodiments. In this example, a lower arch of the patient is shown. It is understood that the same method can also be applied to the upper full arch. The method of generating a full arch descriptor splits a full arch STL or mesh file into two parts, preferably around the central incisor teeth. This gives two different quadrants, namely left quadrant and right quadrant as per where the quadrant is located. FIGS. 20B and 20C each illustrate examples of half of the full arch after splitting the full quadrant, in accordance with some embodiments. Each quadrant can be treated as a separate independent quadrant. Once collected, the 2D matrix describing each dental object processed is added to a descriptor database. Using matching algorithms, machine learning, and artificial intelligence, the 2D matrix representation of dental objects can be classified and matched to other dental objects in the descriptor database. By assigning descriptor classes to each 2D matrix data file, each 2D matrix can be passed through a neural network and a model is created for dental objects in the same descriptor class using the 2D matrix descriptions of the 3D dental object for matching. Using this method of algorithmic matching, similar pattern prediction can be accomplished, with classification of similar groups of 2D matrixes into related descriptor classes. By creating descriptor classes for the 2D matrixes in the descriptor database new dental features can be identified and patterns can be use in anomaly detection, diagnostics, and prosthetic design. In the area of diagnostics, for example, identification of patterns in a descriptor class which suggest disease or degradation will help dental professionals to identify problems more easily and earlier. In one example, gum recession can be measured and monitored, and patterns of gum recession from gum descriptors around the same tooth or teeth in the descriptor database, either from the same patient or a different patient, can assist in providing early diagnosis of gum disease. Diagnosing gum disease early can also more quickly initiate treatment which can prevent or delay progression.

Dental features and dental objects can be classified into groups such that matching descriptor matrixes can be more easily searched. In one schema a class one dental feature can be defined as a feature encapsulated by a single tooth and a class two dental feature can be defined as a feature that encompasses more than one tooth or complex dental object such as a gumline or dental arch. Additional descriptor classes can be assigned by patient age, as the teeth and jaw grow and change from birth to adulthood. In an example, a class one set of descriptors describing single teeth features can include, for example, a crown descriptor, gumline descriptor, margin line descriptor, occlusal face descriptor, side walls descriptor. For single tooth descriptor classes, a single descriptor subclass can be created for each individual tooth, for example, by tooth number and/or tooth name. In particular, descriptor subclasses can be assigned for each of: upper right teeth 1—Central incisor, 2—Lateral incisor, 3—Canine/Cuspid, 4—First Premolar/1st Bicuspid, 5—Second Premolar/2nd Bicuspid, 6—First Molar, 7—Second Molar, 8—Third Molar/Wisdom tooth; upper left teeth 9—Central incisor, 10—Lateral incisor, 11—Canine/Cuspid, 12—First Premolar/1st Bicuspid, 13—Second Premolar/2nd Bicuspid, 14—First Molar, 15—Second Molar, 16—Third Molar/Wisdom tooth; lower left teeth 17—Central incisor, 18—Lateral incisor, 19—Canine/Cuspid, 20—First Premolar/1st Bicuspid, 21—Second Premolar/2nd Bicuspid, 22—First Molar, 23—Second Molar, 24—Third Molar/Wisdom tooth; and lower right teeth, 25—Central incisor, 26—Lateral incisor, 27—Canine/Cuspid, 28—First Premolar/1st Bicuspid, 29—Second Premolar/2nd Bicuspid, 30—First Molar, 31—Second Molar, 32—Third Molar/Wisdom tooth. The present system can automatically classify each tooth using the 2D matrix, or the tooth can be classified manually using metadata accompanying the 2D matrix. Class two descriptors can work in a similar way and can include descriptors which describe the features of several teeth, for example including full arch descriptor, quadrant descriptor, bitewing descriptor, bite registration descriptor, bite pattern descriptor, gum pattern descriptor. Each 2D matrix can be further classified by a descriptor subclass that specifies location of the dental object, such as upper right quadrant, upper left quadrant, lower right quadrant, lower left quadrant, bitewing location, occlusal surface and location, gumline and location, and dental arch.

Figure 21:
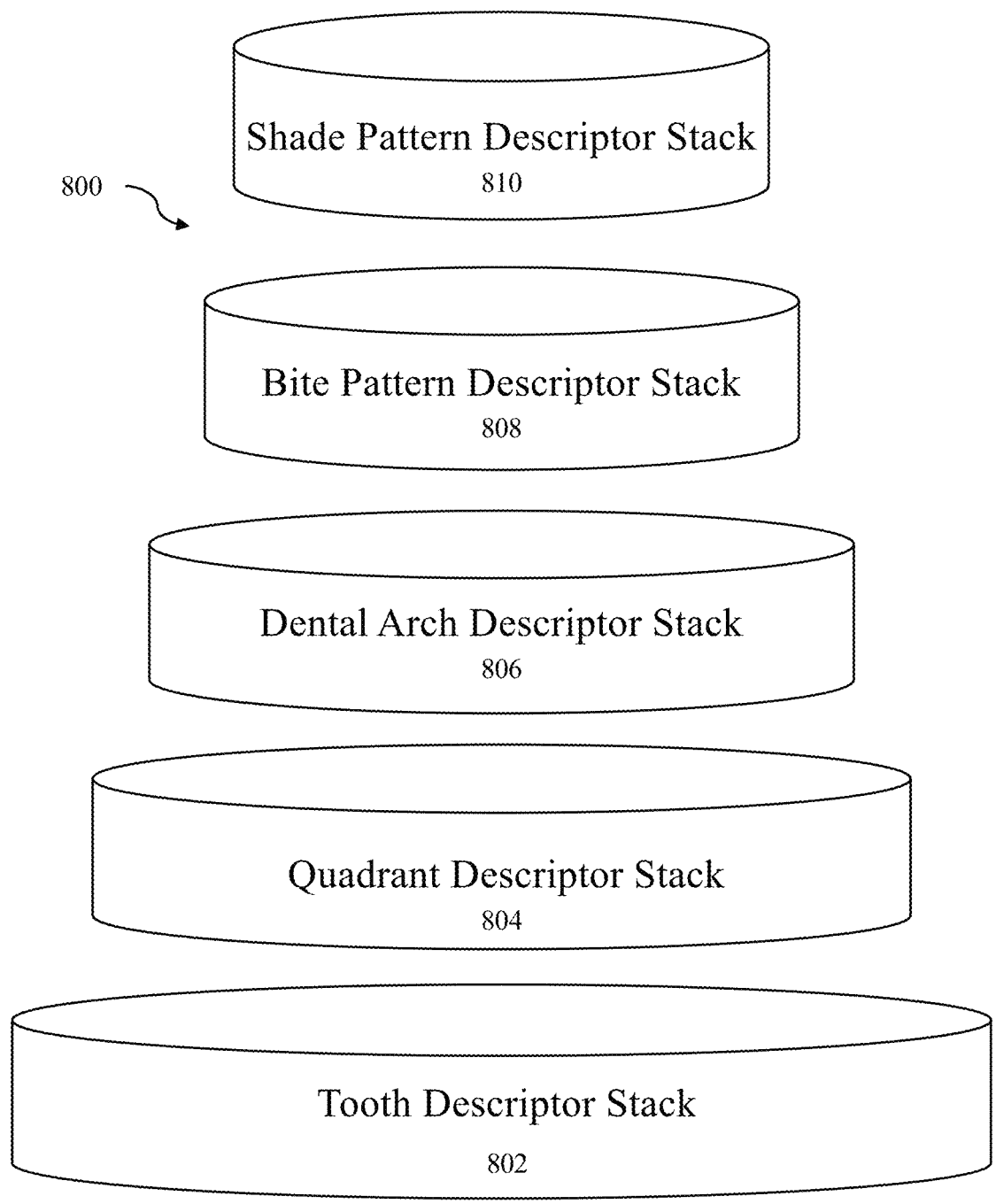
FIG. 21 illustrates an example of a neural descriptors stack.

FIG. 21 illustrates an example of a neural descriptors stack 800, in accordance with some embodiments. A descriptor stack is a stacking of different types of matrices obtained from the above-mentioned descriptor methods, one on top of another. To aid in the readability and parsing of the resulting descriptor matrix or visualization map produced from the mesh file of the dental object, a variety of descriptor matrixes and descriptor stacks can be obtained of the dental object to provide additional granularity and detail around the shape of the dental object. These include but are not limited to a single tooth descriptor stack 802, a quadrant descriptor stack 804 of teeth in a quadrant, a dental arch descriptor stack 806, a bite pattern descriptor stack 808, and a shade pattern descriptor stack 810. Each output comprises one or more matrixes describing the dental object, and a descriptor stack is generally understood as a plurality of descriptor matrixes that correspond to the same dental object image and are anchored in space. In some cases, a new descriptor method (e.g., a bite pattern descriptor) may be obtained depending upon the feature requirement. The complexity level increases from the bottom-level stack 802 to the top-level stack 810. It is noted that there is no direct relationship between the number of matrices stacked on a particular descriptor stack and the complexity of that descriptor stack.

Figure 22A:
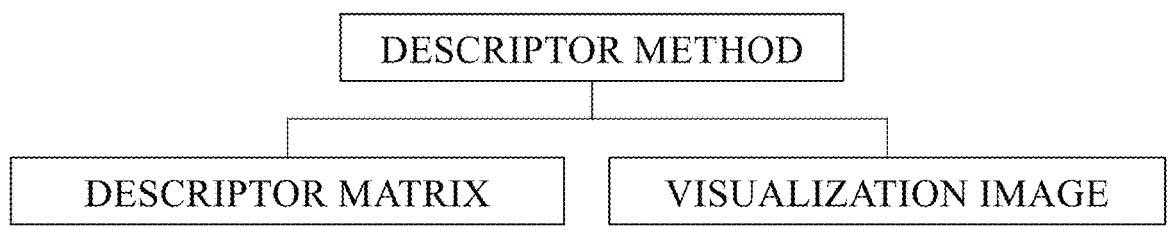
FIG. 22A is a tree diagram of the relationship between descriptor methods and output.
Figure 22B:
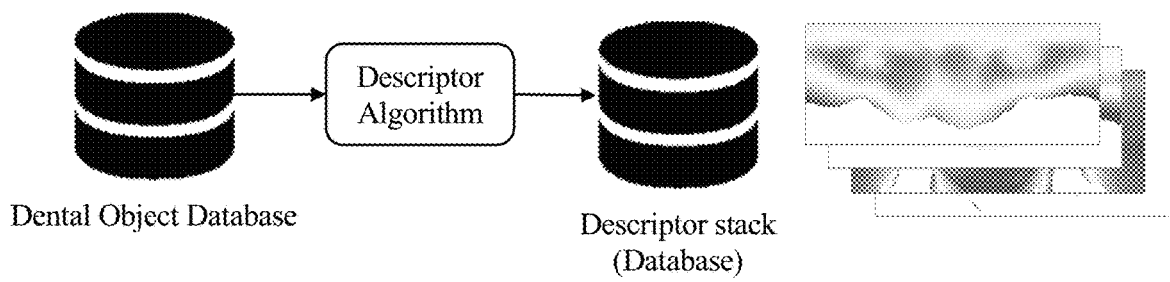
FIG. 22B illustrates a method for converting a dental object database comprising mesh files of dental objects into a 2D dental descriptor stack database.

FIG. 22A illustrates, in a tree diagram, an example of a relationship between descriptor methods and output in a neural descriptors stack, in accordance with some embodiments. Descriptor generation methods give mainly two types of output, a first output descriptor matrix and a second output as an image file or visualization map. FIG. 22B illustrates a method for converting a dental object database comprising mesh files of dental objects into a dental descriptor stack database comprising two-dimensional descriptor matrixes. Dental object databases exist which store a plurality of mesh file images of dental objects, and the entire database can be converted en masse to a descriptor stack database such that the dental images can be classified and matched.

Figure 22C:
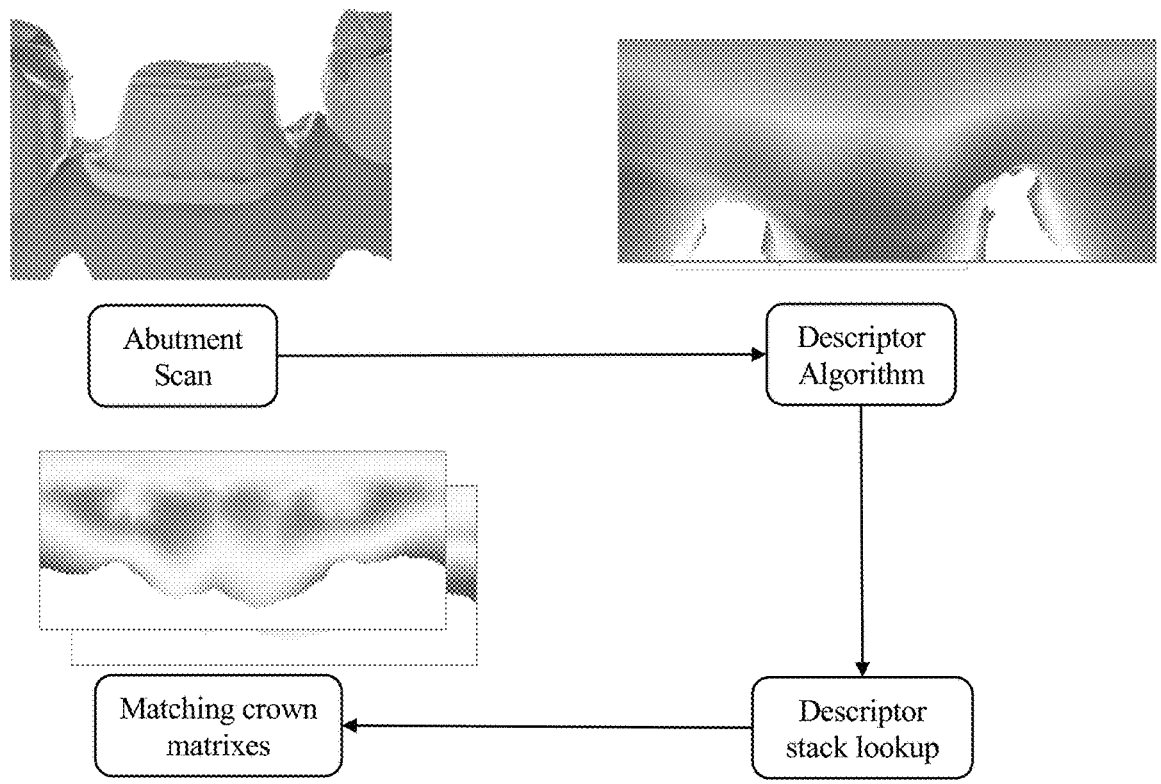
FIG. 22C illustrates a method of matching a dental post to a matching crown in a dental object database comprising dental objects represented as two-dimensional descriptor matrixes.

FIG. 22C illustrates a method of matching a dental post to a matching crown in a dental object database comprising dental objects represented as two-dimensional descriptor matrixes. In a descriptor stack database both the descriptor matrix stack and the visualization map for each descriptor matrix can be easily scanned to identify matching descriptor stacks. In this example an abutment scan of a crown post is converted into a descriptor matrix stack comprising a descriptor matrix for the outside of the crown post, gumline, and neighboring tooth environment using a descriptor algorithm. Each descriptor matrix in the complete descriptor stack can then be searched in the descriptor database in the descriptor matrix classification of that matrix and one or more matching matrixes can be brought forward as matching to a minimal degree as set by the algorithm. In the example shown the matching crown matrixes are brought forward as matching the abutment scan, however concurrent matching gumline matrixes and matching neighbor tooth matrixes can simultaneously be brought forward based on the original descriptor stack. In crown design, design of the gumline abutment of the crown can be automated based on matching descriptor matrixes of the gumline, and simultaneously design of the exterior surface of the crown can be automated by using the matching descriptor matrixes to the neighbor teeth stack to obtain the fit of the crown adjacent to neighboring teeth. By using the various descriptor matrixes each describing a different aspect of the crown and crown environment the crown design can be automated.

A tooth descriptor is a matrix outcome of either single tooth descriptor method. FIG. 23A illustrates an example of a method of obtaining a tooth descriptor matrix 208 of a dental object 200, in accordance with some embodiments. Dental anatomy represented as a mesh or STL file image type of a dental object 200, in this case a bitewing of a patient, may be any quadrant or full dental arch. First, the targeted tooth is identified and, depending upon the descriptor method selected, the mesh file at the location of the single tooth is sliced radially or in parallel. For illustration purposes radial slicing is shown. The tooth descriptor matrix 208 may be obtained following the method steps as set out above.

A descriptor stack is a stack of descriptor matrices that describe the dental object and are aligned or anchored in space relative to the dental object. Each descriptor matrix in the descriptor stack is aligned using a common centroid during conversion of the dental object into the descriptor matrixes which enables comprehensive stacking of the resulting descriptor matrixes. This results in each descriptor matrix in the descriptor stack being anchored or aligned such that the descriptor stack describes different aspects of the dental object or parts thereof with the same alignment on the dental object. In a specific example, a descriptor stack may comprise a single crown post descriptor matrix and an aligned bitewing descriptor matrix. In some embodiments the descriptor stack is a combination of an dental arch descriptor method to provide a dental environment and a corresponding single tooth descriptor method for each tooth in the arch, where the location of each single tooth descriptor matrix is anchored or referenced relative to the descriptor matrix of the dental arch. This descriptor stack method can be applied to any quadrant or bitewing of either of the upper or lower jaws. FIG. 23B illustrates an example of a method of obtaining a quadrant descriptor stack for a bitewing, in accordance with some embodiments. A bitewing with four teeth is shown. The bitewing STL/mesh file goes through an arch descriptor method to obtain a descriptor matrix output. As there are four teeth in this bitewing, the result of a descriptor stack method can have four single tooth descriptor matrices 208.

Figure 24:
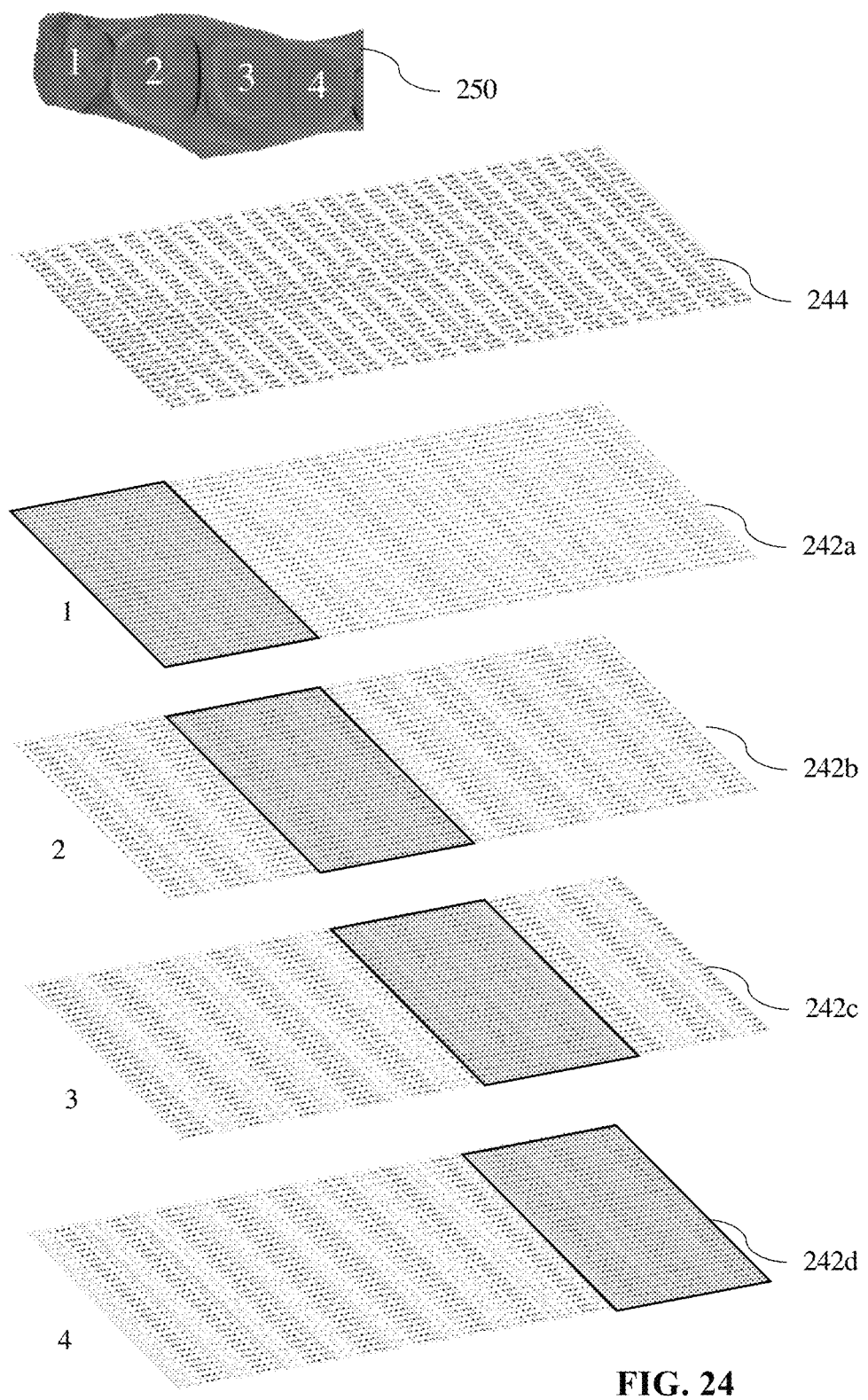
FIG. 24 illustrates an example of a quadrant descriptor stack.

FIG. 24 illustrates an example of a dental quadrant 250 descriptor stack output of the present method. This example quadrant descriptor stack comprises five (5) descriptor matrices, a quadrant descriptor matrix 244 and four single tooth descriptor matrices 242*a*, 242*b*, 242*c*, 242*d* each individually describing teeth 1, 2, 3, 4 in the quadrant, respectively. Each of matrices are single tooth descriptor matrices 242*a*, 242*b*, 242*c*, 242*d*, with zero padding entries to ensure that they are the same size as quadrant descriptor matrix 244. The resulting quadrant descriptor stack provides a visual representation of a 2-dimensional descriptor matrix that represents the distance travelled by each indexing ray onto the surface of a dentist's preparation surgery scan. In each descriptor matrix each pixel corresponds to a single ray intersecting the exterior surface of the dental object that it describes, and the intensity of the pixel color corresponds to the distance the ray travelled from the common centroid before hitting or intersecting with the triangulated mesh surface. On this array we can see bold lines on the surface of the 2-dimensional matrix. The bolded or shaded areas in each single tooth descriptor matrices 242*a*, 242*b*, 242*c*, 242*d* are unique 2-dimensional descriptor matrices that each represent a specific feature on the surgical preparation or quadrant for each tooth. In each matrix it is noted that the bottom line represents the margin line, the middle line represents the location where the preparation shoulder meets the preparation wall, and the top line represents the transition to the occlusal surface on the preparation. By isolating each feature to its own matrix, data can be gathered from each dental object and an artificial intelligent/machine learning matching engine can be trained to make assessments about how the crown should be designed for any specific preparation.

Figure 25:
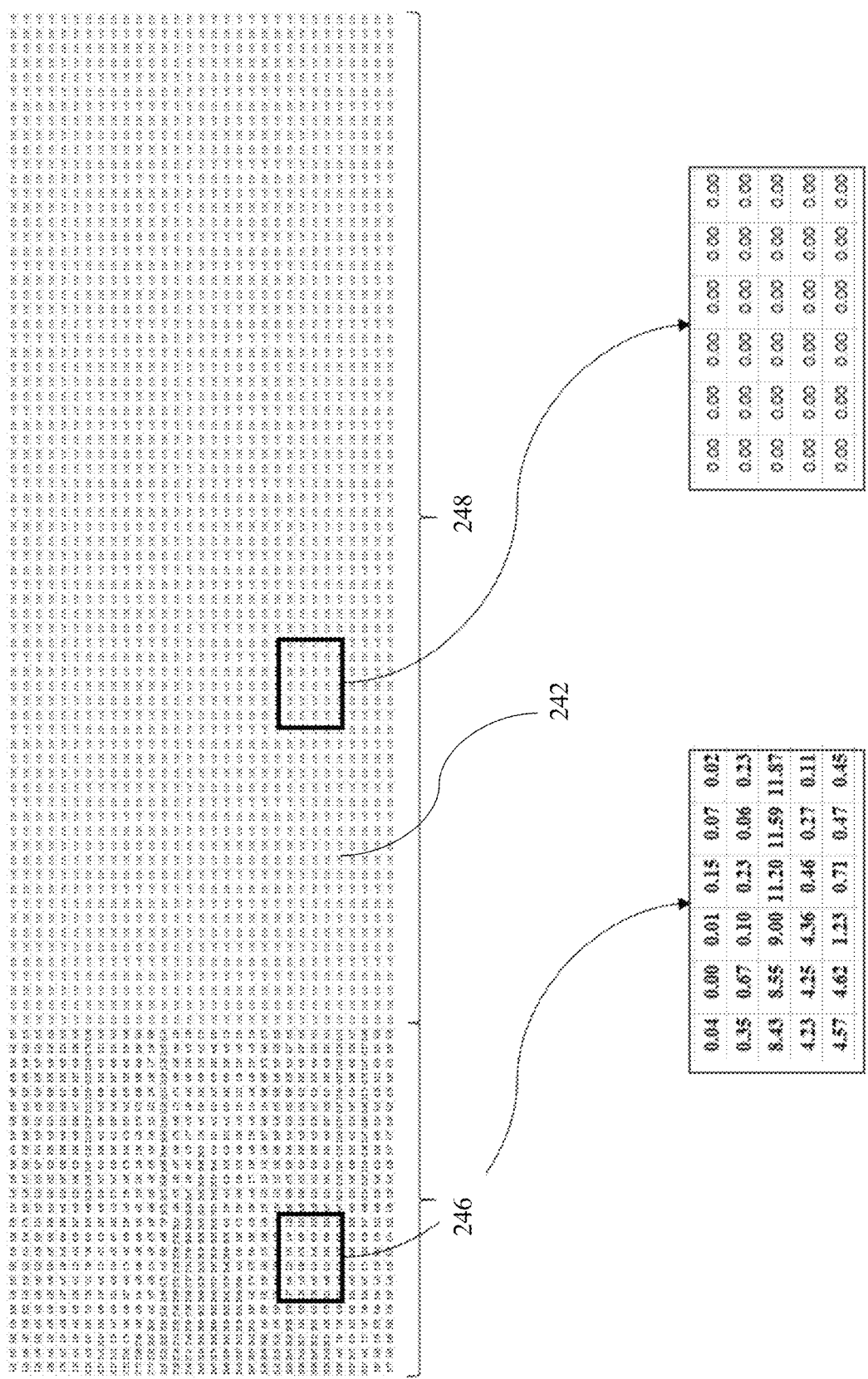
FIG. 25 illustrates an example of a single tooth descriptor matrix inside a quadrant.

FIG. 25 illustrates an example of a single tooth descriptor matrix 242, in accordance with some embodiments. The first tooth descriptor matrix has encoded region 246 describes, for example, the first tooth in a dental quadrant as shown in FIG. 24 of the above-mentioned single tooth descriptor matrices. This single tooth descriptor matrix 242 which comprises encoded region 246 describing the single tooth is modified by adding a zero or non-encoded matrix padding region 248 to make it the same size as the quadrant descriptor matrix shown in FIG. 24. It should be noted that both quadrant descriptor matrix and single tooth descriptor matrix should have the same number of ray lengths. The number of slices in the quadrant descriptor matrix should be equal to several teeth of the quadrant multiplied by the number of slices of the single tooth descriptor matrixes, with all teeth preferably having about the same number of slices or slicing planes. The single tooth descriptor matrix 242 may be placed in the first portion 1 of the whole quadrant descriptor matrix as encoded region 246 as this matrix represents the first tooth labeled 1 of the dental quadrant shown in FIG. 24. The remaining three portions are filled by zeros in padding region 248 as shown. The matrixes for teeth 2-4 as shown in the quadrant in FIG. 24 may be generated in a similar manner.

Figure 26A:
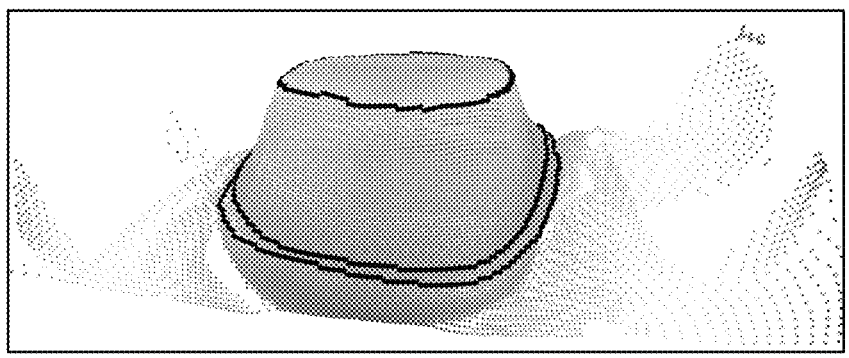
FIG. 26A illustrates a 3D mesh file image of a dental post with three circumferential surface lines.
Figure 26B:
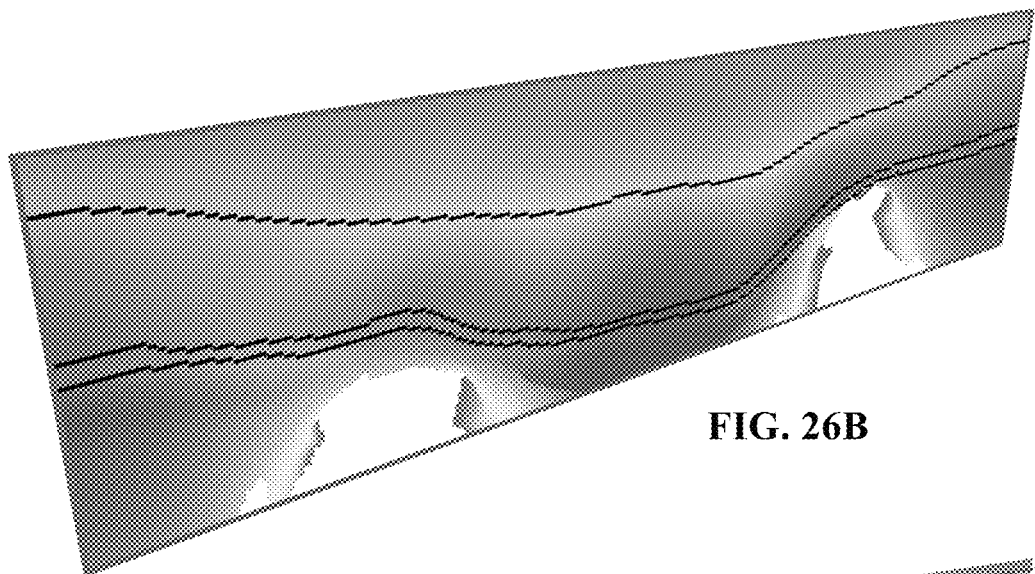
FIG. 26B illustrates the dental post of FIG. 26A showing the three circumferential surface lines superimposed on a two-dimensional descriptor matrix.
Figure 26C:
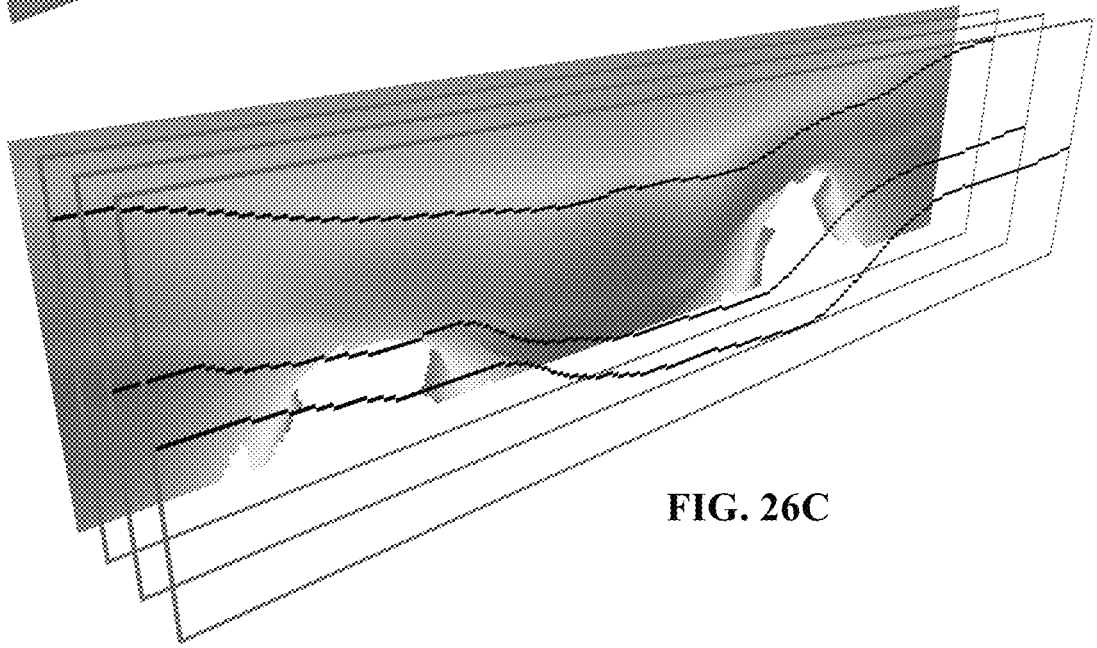
FIG. 26C illustrates the superposition of the three circumferential surface lines in FIG. 26B on the descriptor matrix.

FIG. 26A illustrates a 3D mesh file image of a dental crown post with three circumferential surface lines. FIG. 26B illustrates the dental post of FIG. 26A showing the three circumferential surface lines superimposed on a two-dimensional descriptor matrix of the crown post. FIG. 26C illustrates the superposition of the three circumferential surface lines on the descriptor matrix. As shown, each circumferential surface feature is its own descriptor matrix and all the 2-dimensional matrices can be stacked since each pixel represents the same indexing ray extended from the same reference location or centroid, meaning that each feature is aligned relative to one another.

Figure 27:
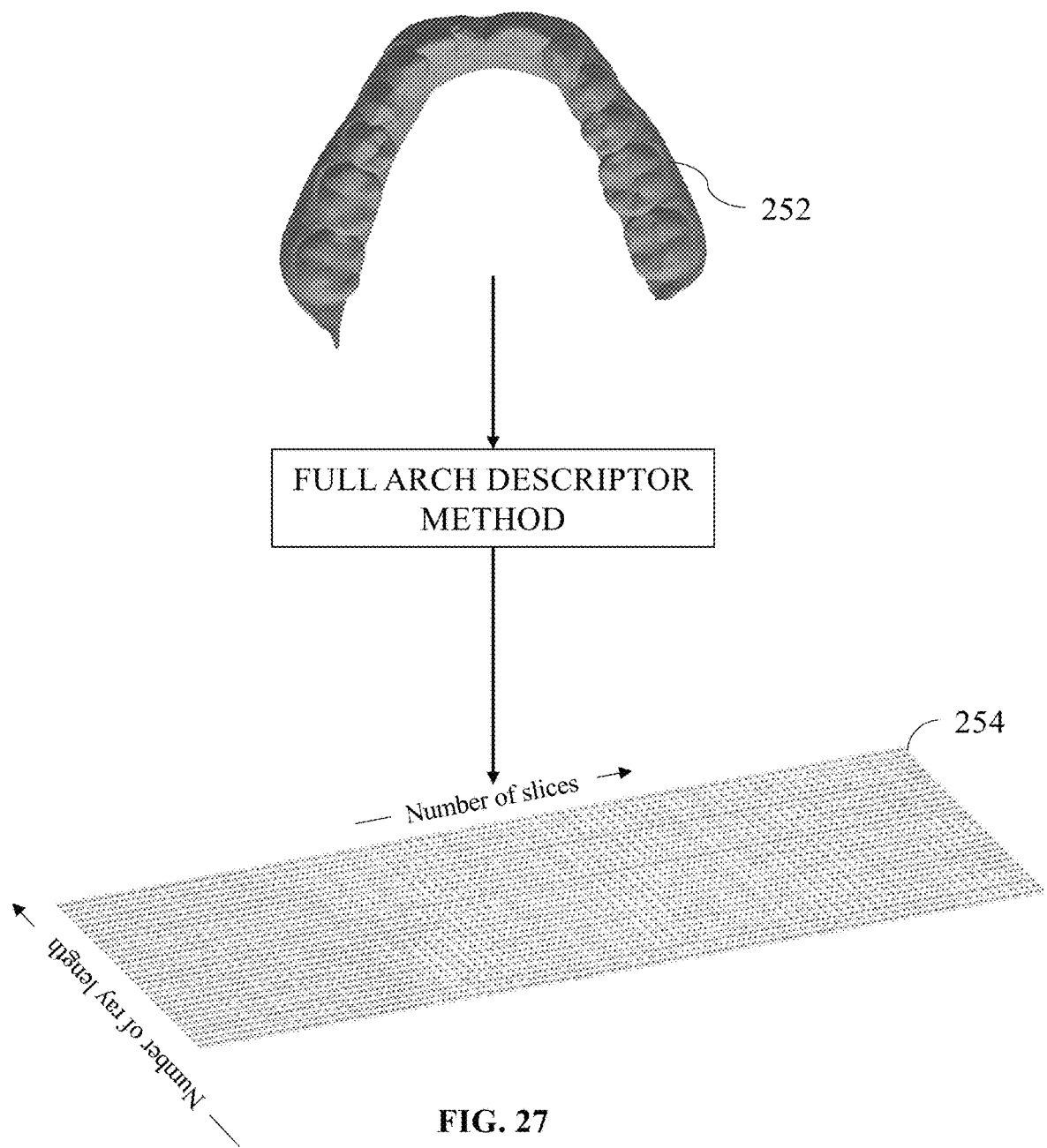
FIG. 27 illustrates an example method of obtaining a dental full arch descriptor stack.

FIG. 27 illustrates an example of a method of obtaining a dental arch descriptor stack. A dental arch descriptor stack is a stack of matrices. The dental arch descriptor stack is a combination of the output of multiple arch descriptor methods output as a single arch descriptor matrix 254 with corresponding single tooth descriptors outputs as multiple single tooth descriptor matrixes for each tooth in the dental arch 252. This full dental arch descriptor stack can be applied to either of upper or lower jaw full arch. Shown is an example mesh file image of a lower dental arch 252 which has fourteen teeth that is passed through an arch descriptor method to generate output as a single arch descriptor matrix 254. As there are fourteen teeth in this arch the resulting arch descriptor matrix 254 can be comprised of fourteen distinct single tooth descriptor matrices.

Figure 28:
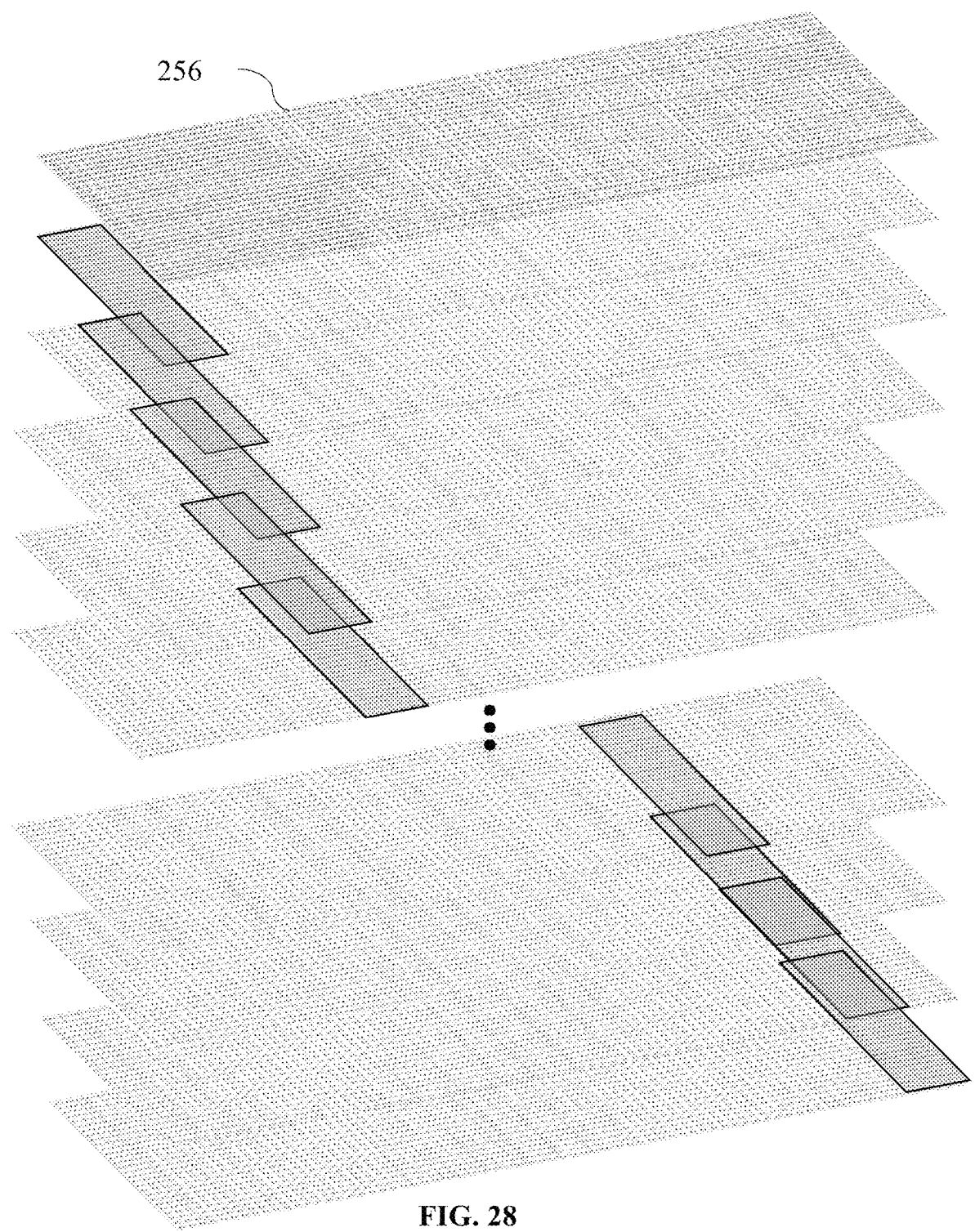
FIG. 28 illustrates an example of a dental arch descriptor stack.

FIG. 28 illustrates an example of a dental arch descriptor stack 256, in accordance with some embodiments. This descriptor stack 256 comprises fifteen individual related matrices which are each anchored to one another in space by a reference locus, such as a common reference point, reference axis, or common centroid. All single tooth descriptor matrices are represented differently to ensure they have the same size as the dental arch descriptor matrix 256. The position and the structure of the modified single tooth descriptor matrices are the same as mentioned above in the quadrant descriptor stack. The position of each tooth descriptor stack is determined by where it is in the dental arch.

A bite pattern descriptor stack can be assembled to model a patient's bite and for the purposes of evaluating whether their bite is good, for example whether upper and lower teeth have sufficient occlusion surface to provide surface for mastication or chewing. Using the present method an electronic bite registration can be obtained in a mesh or STL filetype and converted to a descriptor stack to automatically evaluate a patient's bite. A bite registration in dentistry is an impression or image of a patient's upper and lower teeth in the bite position and can also be used in dental prosthetic design for a better fit for designing crowns, dentures, mouth guards, and other prosthetic and orthodontic devices. A bite pattern descriptor stack is a combination of two general matrices: the bite pattern descriptor matrix and the bite registration descriptor matrix. The bite pattern descriptor stack may comprise two images corresponding to the bite pattern descriptor and the bite registration descriptor. The generation of both descriptors starts with an STL or mesh file that comprises both upper and lower jaw dental anatomy and can be either a full arch, bitewing, or quadrant.

FIGS. 29A and 29B illustrate an example of a bitewing, in accordance with some embodiments. As shown, the bitewing has both upper bitewing and lower bitewing. FIG. 29A illustrates an example of a bitewing with bitewing common centroid and FIG. 29B illustrates an example of cross-sectional slice of a bitewing. An image of each bitewing can be collected using a dental imager individually, i.e. top bitewing and bottom bitewing separately, as well as together in a biting conformation. The biting conformation image can then be used to align the top and bottom bitewing images to create a single mesh file of both bitewings together. Slicing planes through both upper and lower bitewings 0, 1, 2 . . . 142, 143, 144 are shown slicing the dental object along the same plane originating from a bitewing centroid to anchor the upper bitewing and lower bitewing in the resulting bite pattern descriptor stack. It should be noted that the 144 slices are for illustration purposes and that the number of slices may vary depending on the anatomy and desired descriptor matrix quality. Accordingly two mesh files, one for each bitewing, can be used to create a single aligned mesh file which is a representation of the patient's teeth in the biting position. In one example, occlusal radiography can be used to image and/or align the upper and lower bitewing. The merged mesh file can be converted into a single bite pattern descriptor stack of matrixes describing the entirety of the bite pattern. This bite pattern descriptor stack can then be used to automatically evaluate the effectiveness of the bite as well as compare the bite to other bite patterns in the descriptor database for the purposes of finding matching bite patterns for the purpose of remediating problematic bite patterns. For ease of presentation, images of actual teeth in FIG. 29A are not shown, however in practice images of teeth and/or visualization maps of the descriptor matrix or matrices could be presented to a dental professional on a graphical user interface for inspection and analysis.

Figure 30:
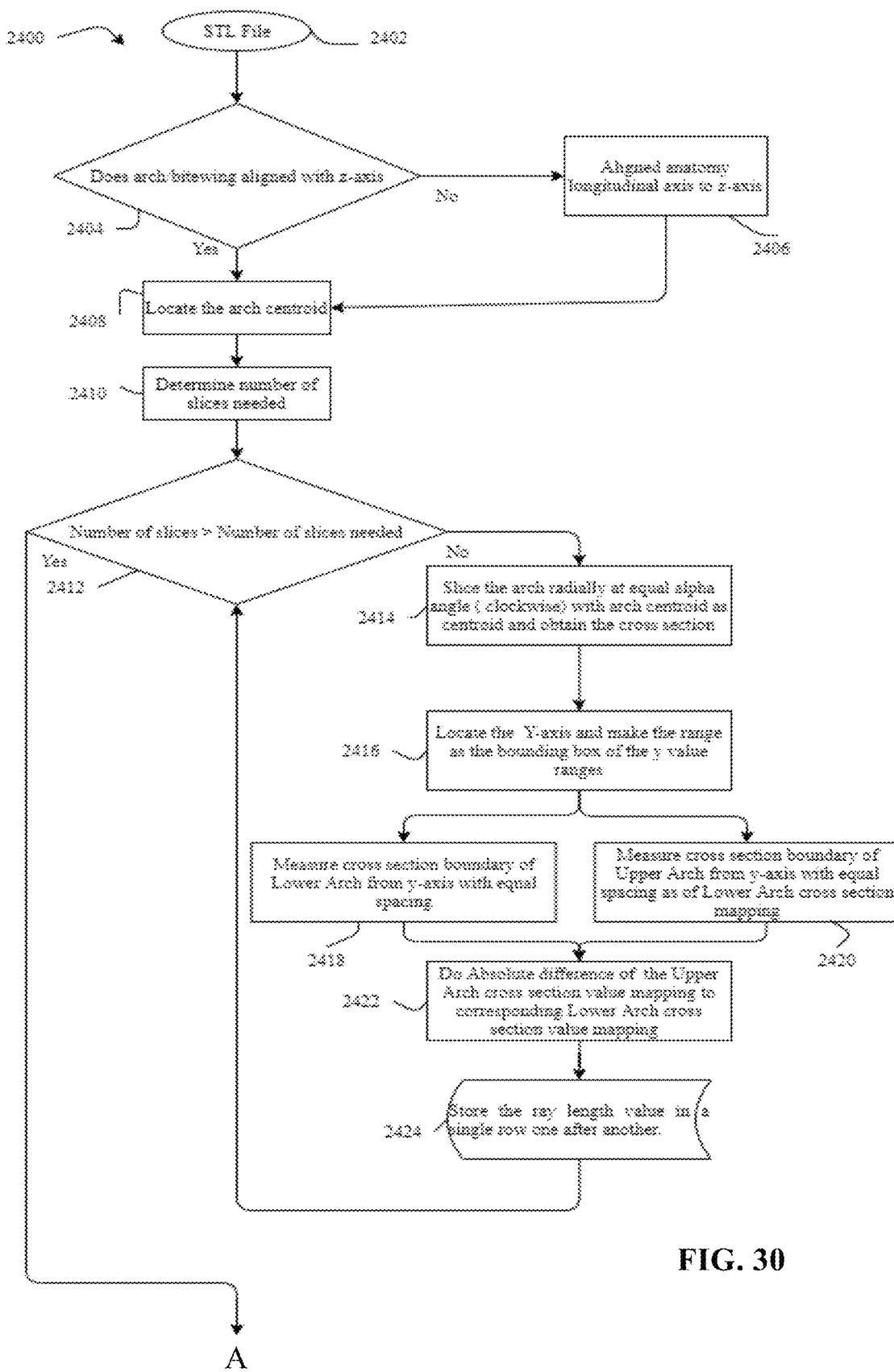
FIG. 30 is a flowchart of an example method of generating a bite pattern descriptor stack.

FIG. 30 illustrates, in a flowchart, an example of a method of generating a bite pattern descriptor stack 2400 and how to obtain both upper and lower descriptor matrixes, in accordance with some embodiments. A three-dimensional STL dental anatomy 2402 as described above is used as an input to the present method. The method queries whether the z-axis is aligned with the anatomy's longitudinal axis 2404. If it is not 2404, the anatomy (e.g., arch, bitewing, quadrant) is aligned with the z-axis 2406. In some embodiments the system automatically aligns the dental anatomy's longitudinal axis to the z-axis. For example, the system may generate a transformation matrix which moves the center of a bounding box of the input STL to the origin. This aligns the dental anatomy's longitudinal axis aligned with the z-axis. The alignment ensures that the data is stored uniformly. FIG. 29A shows the z-axis direction relative to the dental object. Next, arch centroid is located 2408 and the number of slices needed to ensure all features are covered are determined 2410. For example, if the number of slices are too few, then the space between slices may be large enough so that their cross-sections do not show an anomaly or feature of the anatomy. Determining the number of required slicing planes 2410 will determine the quality of the matrix and the image. The method 2400 may now go into a loop based on condition which determines if the number of slicing planes is sufficient for image conversion 2412. If the number of slices is not greater than the number of slices needed 2412 then the dental object or anatomy is sliced radially at an approximately equal alpha angle (see FIG. 29A that shows 144 slices for the bitewing). Dental object slicing is done on a plane normal and in a clockwise direction with the bitewing centroid as a plane origin 2414 to obtain a cross-sectional view for each slice. FIG. 29B shows an example of a bitewing slice cross-section view. It should be noted that the slicing can be from right to left as long as all teeth are sliced consistently in the same manner (i.e., always from left to right, or from right to left). Next, the y-axes are determined for each slice in order to measure the cross-section. It should be noted that in some embodiments the x-axis may be used, however, in this example, the y-axis is selected as a reference. The range of the axis should be the y-axis bounding box value 2416 to ensure that the whole cross-section is covered. The cross-sectional boundaries are measured for both upper bitewing and lower bitewing. The ray length measurements of the cross section boundaries of the upper bitewing 2420 and lower bitewing 2418 arch to the y-axis are then recorded. Once the distance is captured, an absolute value difference between the two distances is taken 2422 and evaluated to show the absolute distance between the corresponding upper and lower bitewing teeth. This provides an output consisting of all of the ray length values for that slice, and the ray lengths can be stored as a single row unit 2424 in a descriptor matrix. By running this loop (steps 2412 to 2424) multiple times single row units for each slice can be obtained and stored in the descriptor matrix format one after another.

Once the number of slices obtained 2412 is greater or equal to the number of slices required (FIG. 30 ctd. following 'A') the resulting descriptor matrix may be stored in the matrix database 2426. The descriptor matrix may also be stored in an image format. A visualization map may be generated by representing the maximum and the minimum values in the matrix to chosen color extreme values, and saving an image file corresponding to the tooth matrix 2428. The image file format is not limited to any single file format, and can be stored in a repository 2430. The tooth database may be linked with the image repository. As the area of interest and site of dental file segmentation is at the bite is where exactly both upper bitewing teeth and lower bitewing teeth touch, the resulting descriptor matrix provides the bite pattern feature in both matrix and image format. The method can also take the same generated descriptor matrix and run it through condition 2432 to evaluate where in the descriptor matrix a particular value is less than or equal to a threshold value of 0.1. Depending upon the situation and feature requirement the threshold value can be varied to provide the desired data. The system can then normalize the descriptor matrix data by replacing values less than the threshold with a one-unit 2436. If not 2432, then the value can be replaced by a zero unit 2434. The resulting descriptor matrix can thereby show the extent of locations in the bite pattern where there is good bite, such as where upper and lower bitewing surfaces meet at a less than threshold distance, and where there is bad bite in locations where the distance is greater. The size or number of cells in the bite pattern descriptor matrix remains the same as there is no change in the number of slices or ray length values, however the amount of data can be greatly reduced with the normalization step. The resulting bite registration descriptor matrix can be stored in the matrix database 2438. This method also allows the storage of the descriptor matrix in image format and can be performed by representing the maximum (one unit in this case) and the minimum value (zero units in this case) in the matrix to the chosen color extreme values. An image file for the corresponding bite pattern tooth descriptor matrix is obtained 2440 and can be stored 2442 with the same descriptor describe above for the tooth database and can be linked with each other. The image file format is not limited to any single file format.

Figure 31A:
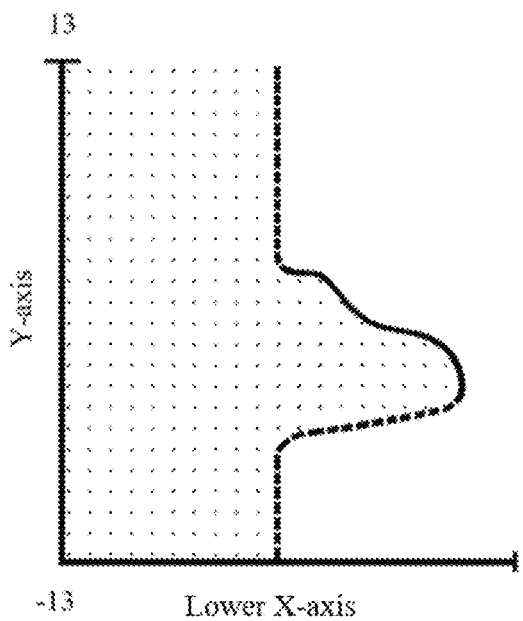
FIG. 31A illustrates measurement of cross section boundaries of a lower arch x-axis.
Figure 31B:
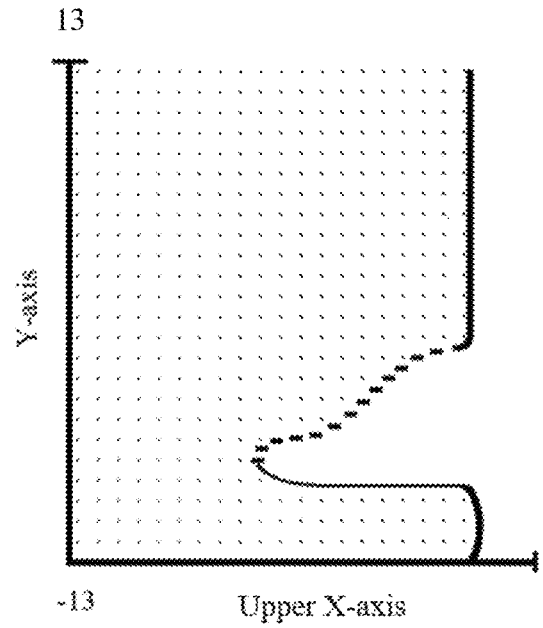
FIG. 31B illustrates measurement of cross section boundaries of a upper arch x-axis.
Figure 31C:
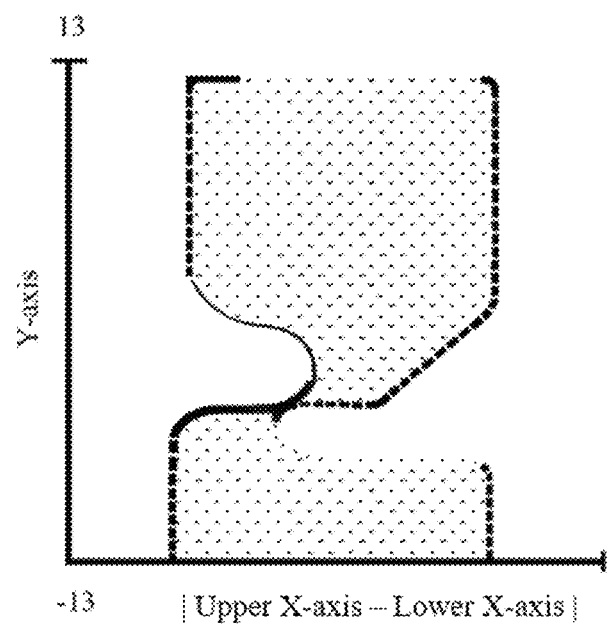
FIG. 31C illustrates an example of a bite pattern for upper and lower arches.

FIG. 31A and FIG. 31B illustrate, in graphs, examples of the measurements of cross section boundaries of the upper and lower arch along the x-axis. FIG. 31C illustrates, in a graph, an example of the bite pattern for upper and lower arches along the x-axis. As shown in FIGS. 31A to 31C, the range of the Y-axis is the same. In this example, the range is −13 to 13 units.

FIGS. 32A to 32C illustrate an example of bite images in a mesh file format, where FIG. 32A is a front view of bite image, FIG. 32B is a side view of bite image, and FIG. 32C is a top view of bottom dental arch bite image. FIGS. 32A-C show the bite taken from the patient's mouth which has full arch upper and lower jaw. FIGS. 32A and 2B illustrate examples of a bite pattern descriptor visualization and a bite pattern registration descriptor visualization, in accordance with some embodiments.

FIG. 33A describes the output of the images of the bite pattern descriptor for a three-dimensional mesh file shown in FIGS. 32A to 32C. In particular, FIG. 33A illustrates an example bite pattern matrix descriptor visualization and FIG. 33B illustrates an example bite pattern registration descriptor visualization. As seen in the middle of FIG. 33A, the gradient white colour structure represents the variation of distance between upper and lower connecting teeth. The images describe the adjacent teeth distance distribution from left to right. FIG. 32B describes the image output of a bite registration descriptor for that three-dimensional file in FIGS. 32A to 32C. The black spots seen along the centerline of FIG. 33B occur when there are upper and lower teeth that are touching (e.g., the distance is <=0.1 in this case). The image thus describes the teeth touching each other from all from left to right (bottom to top in the images shown) and this bite pattern registration descriptor visualization can be used to analyse whether the patient has a good bite by the surface area or pixels of less than threshold as demonstrative of teeth occlusion. This image type and analysis can also be used to match the bite registration before and after a denture prosthetics is constructed.

Figure 34A:
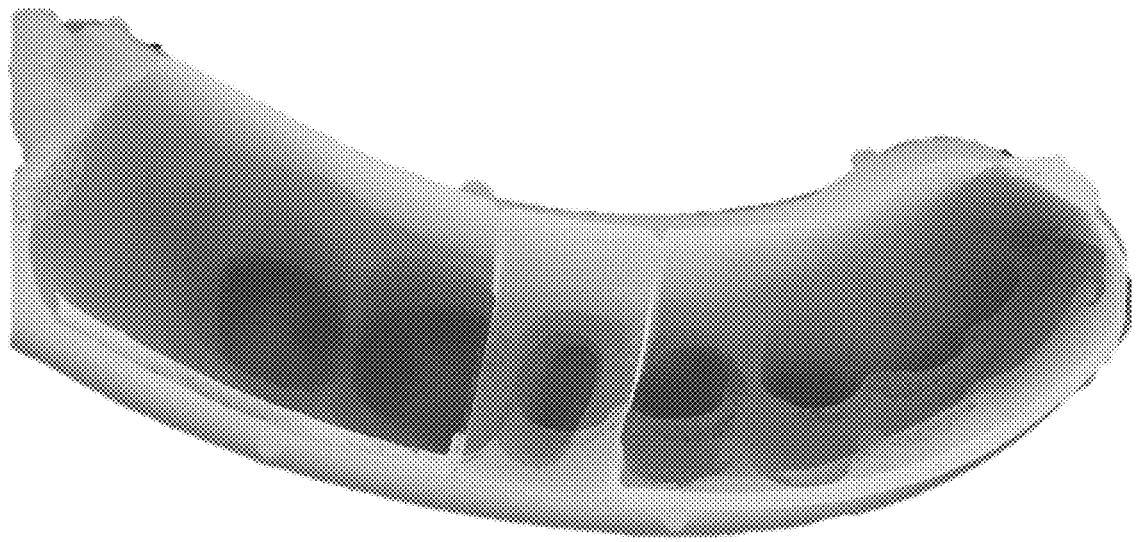
FIG. 34A is a visualization map of an example good bite pattern.
Figure 34B:
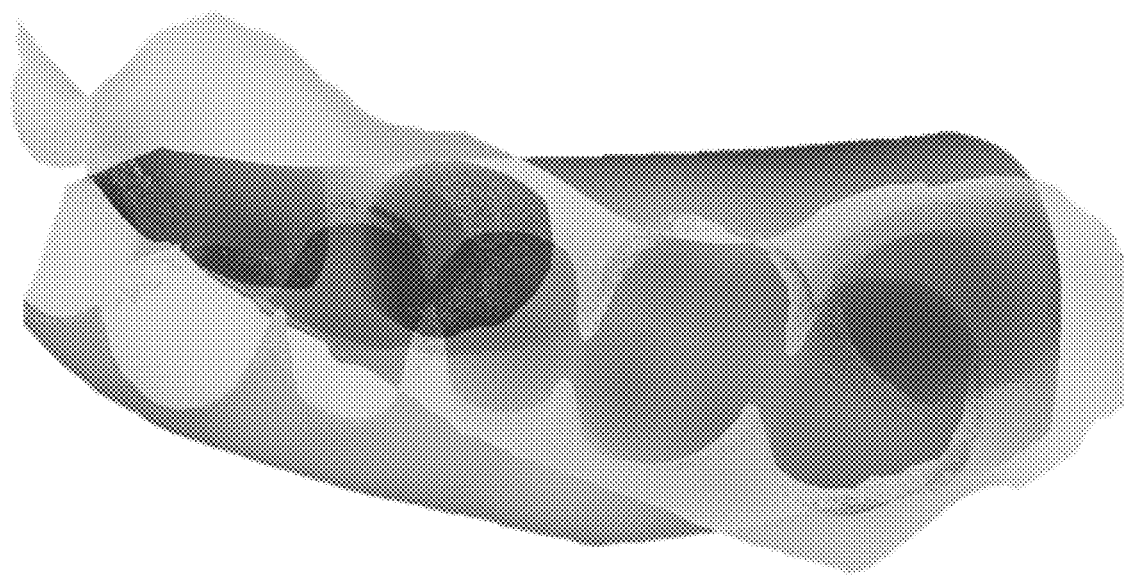
FIG. 34B is a visualization map of an example bad bite pattern.

FIG. 34A is a visualization map of an example good bite pattern obtained from a good bite pattern descriptor matrix and FIG. 34B is a visualization map of an example bad bite pattern obtained from a good bite pattern descriptor matrix. These visualization maps are the product of the present method whereby the 3D mesh images are converted into bite descriptor matrix stacks. To create a visualization map of a bite pattern, a mesh image is obtained of set of teeth comprising an upper subset of adjacent teeth and a corresponding lower subset of adjacent teeth. A reference locus, reference axis, or centroid is assigned outside the 3D representation of the set of teeth. Then a set of indexing rays is extended from the reference locus to determine a plurality of ray lengths between the reference locus and a different point on a portion of the tooth surface, or perimeter of the cross-section if using slicing planes, where the indexing ray length is defined by an axis upper bounding value for the subset of upper teeth and an axis lower bounding value for the subset of lower teeth. An absolute difference between a distance determined for a point on the upper teeth and a distance determined for a corresponding point on the lower teeth can then be determined and the plurality of absolute differences stored in a bite pattern descriptor matrix. In one embodiment, the absolute differences can be stored in a 2D descriptor matrix, where a first dimension of the bite pattern descriptor matrix comprises a number of the plurality of cross-section slices and a second dimension of the bite pattern descriptor matrix comprises a number of the plurality of absolute differences in each slice. The bite pattern descriptor matrix can then be rendered such that each entry in the bite registration descriptor matrix is replaced with a corresponding shade intensity. Absolute difference values greater than a predetermined distance can be given a value of zero, thereby converting the bite registration descriptor matrix to a bite pattern descriptor matrix. As shown, the areas of dental occlusion between the upper and lower bitewings in both visualization maps are shown as black areas and it is evident where occlusion between upper and lower bitewings is occurring, and where it is not. Because the 3D image data has been converted into threshold matrix data a rapid determination of the bite effectiveness of the patient can be automatically provided even without a dental professional looking at the visualization map result, solely based on the mesh image dental object file segmentation and matrix reconstruction. Storage of the bite pattern descriptor matrix is also simplified since the file size of the matrix is much smaller than the original 3D mesh file. For example, 3D mesh files are on the order of 15-40 MB, whereas the present descriptor matrixes can be less than 1 MB.

Figure 35:
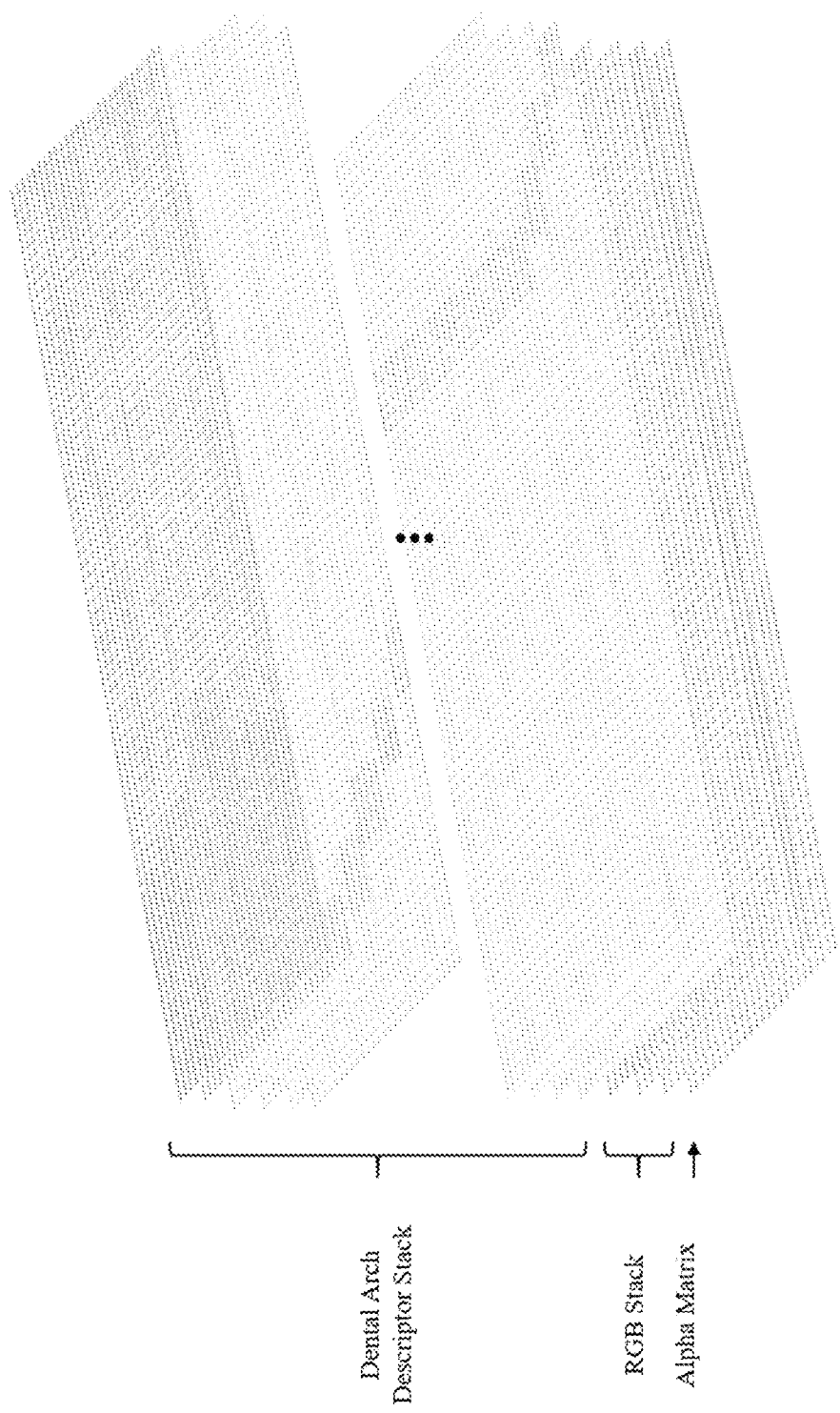
FIG. 35 illustrates an example of a shade pattern descriptor stack.

FIG. 35 illustrates an example of a shade pattern descriptor stack, in accordance with some embodiments. The shade pattern descriptor stack is a stack of matrices and comprises three types of stacks: a descriptor stack, a red-green-blue (RGB) stack, and an alpha matrix. The type of descriptor stack depends upon the type of dental anatomy or dental object under analysis, and can be, for example, a tooth descriptor stack, a quadrant descriptor stack, and/or a dental arch descriptor stack. The RGB stack represents the colour visualization of the selected dental anatomy, and the alpha matrix represents the transparency visualization of the dental anatomy. It has a value range from zero to one. "Zero" (0) represents fully transparent, and "one" (1) represents fully opaque. This descriptor stack can join other types of descriptor stacks, or even a single matrix, to function as desired.

Figure 36:
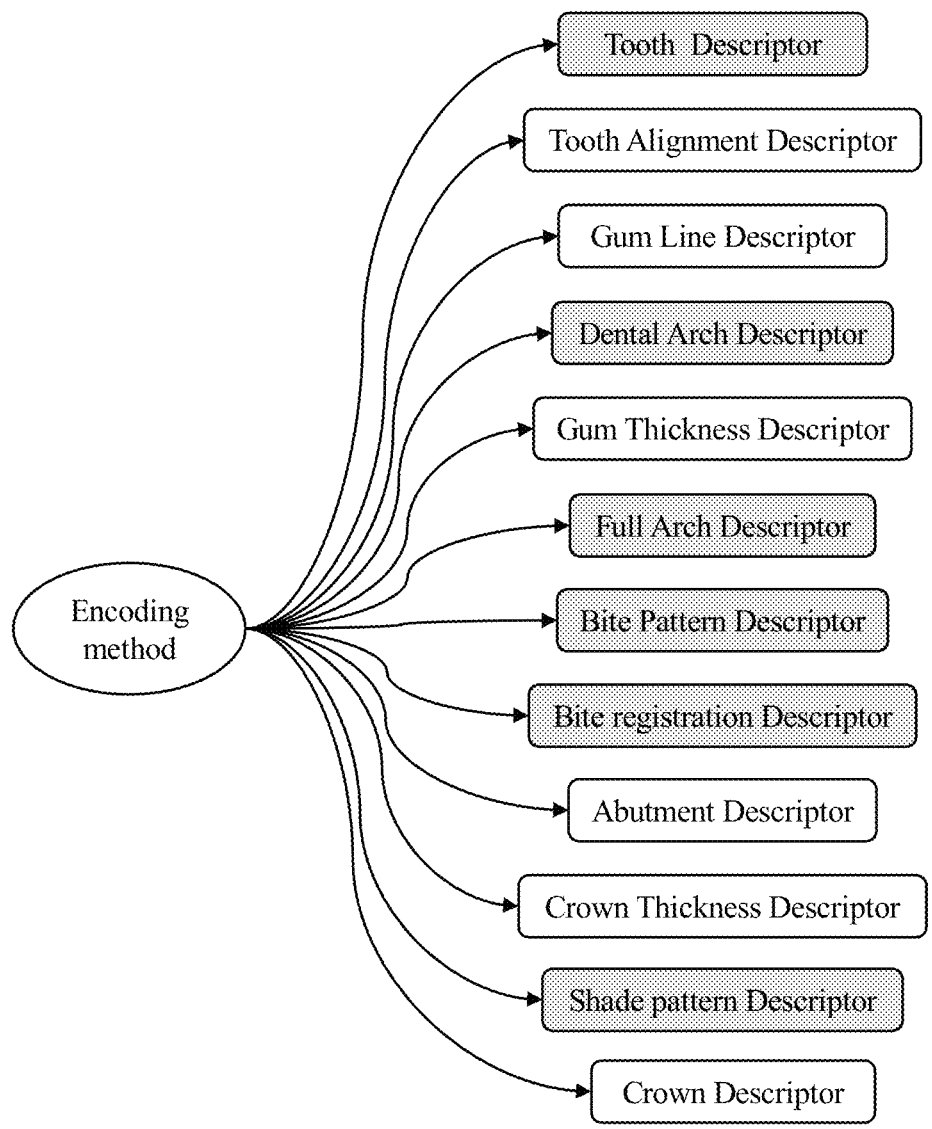
FIG. 36 illustrates an example of a listing of descriptor types in an encoding method.

FIG. 36 illustrates an example of a listing of descriptor types, in accordance with some embodiments. Descriptors can include but are not limited to tooth descriptor, dental arch descriptor, full arch descriptor, bite pattern descriptor, bite registration descriptor, or shade pattern descriptor stacks. Descriptors may also include a tooth alignment descriptor which describes how a tooth is aligned in the dental anatomy concerning each other, a gumline descriptor which can describe where the gumline is located, a gum thickness descriptor which can describe the thickness of the gum, an abutment descriptor which is similar to the quadrant descriptor, a crown thickness descriptor which describes the thickness of the crown, and a crown descriptor which can describe the crown anatomy. Other descriptors may be provided. The encoding method (indexed slicer, radial encoder, Fourier neural operator, and visualization map (image file format) provides the descriptor and each stack of the descriptor, and each descriptor describes features of that dental anatomy.

Figure 37A:
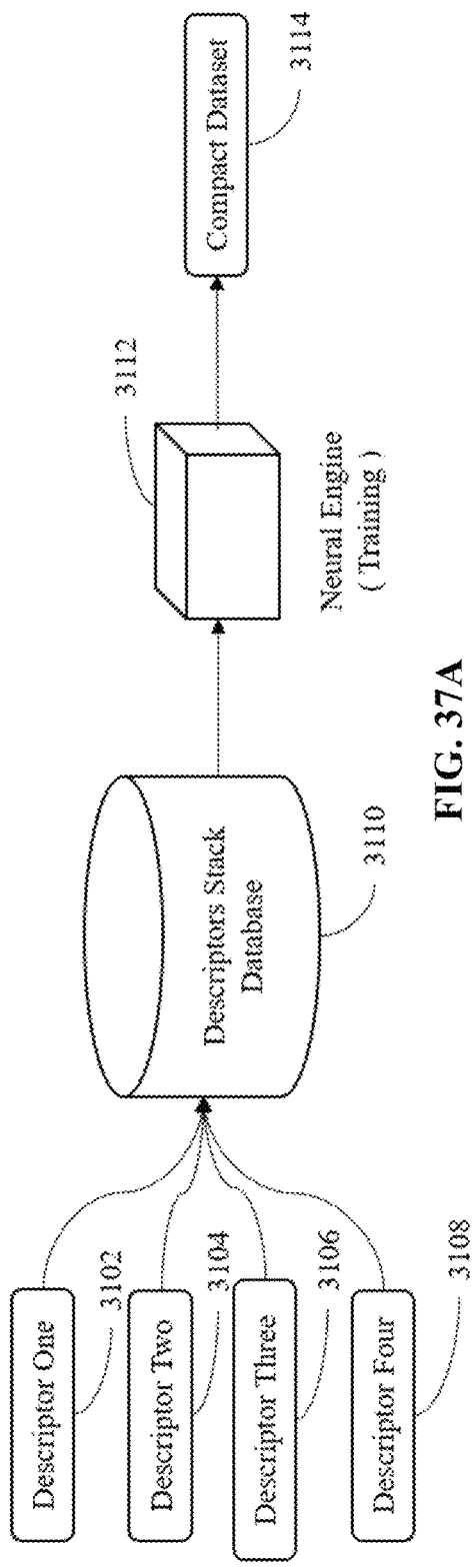
FIG. 37A illustrates a flow diagram of an example of training a dataset.
Figure 37B:
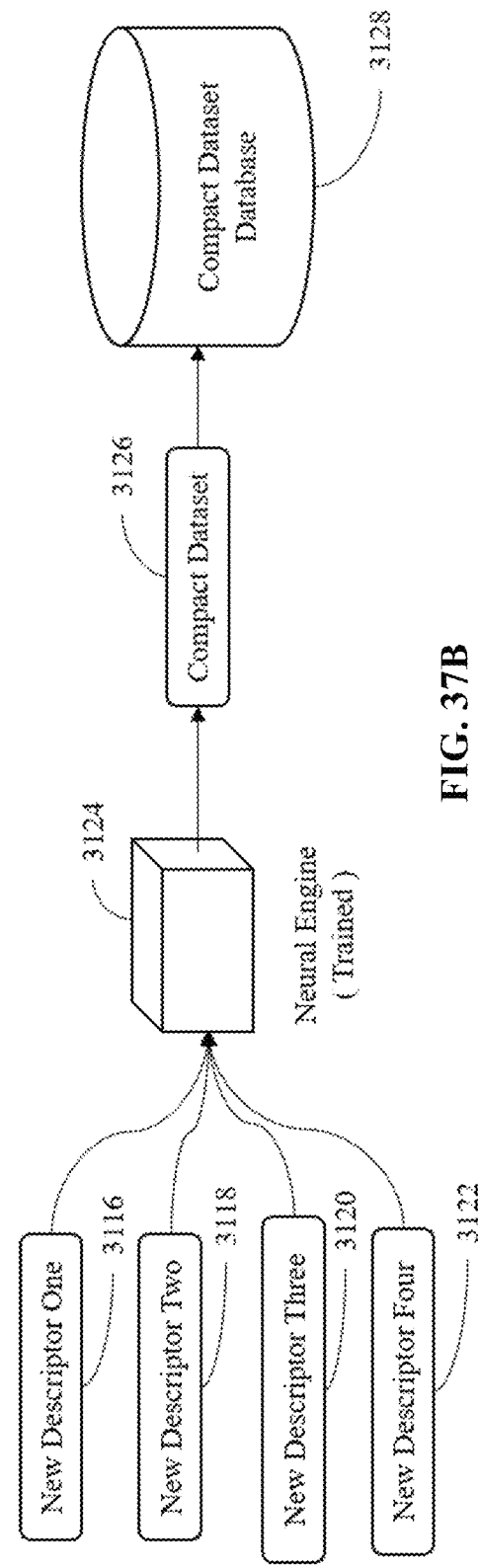
FIG. 37B illustrates a flow diagram of an example of generating a compact data set database.

Depending upon the feature required to describe the dental anatomy or problem, descriptors mentioned above can be used as it is, or they can be stacked with the features desired and stored in a descriptor database. FIG. 37A illustrates, in a flow diagram, an example of using machine learning for training a dataset, in accordance with some embodiments. In one example, four descriptors 3102, 3104, 3106 and 3108, however it should be understood that as few as one descriptor and any number of descriptors may be used. Descriptors are stored in a descriptors stack database 3110. These descriptors are used for training a neural engine 3112 (for example, a convolutional neural network model) to generate a compact dataset 3114. The compact dataset 3114 may be represented as a matrix, and stores the features desired. Its size is small as compared to both STL files and the descriptors matrices. FIG. 37B illustrates, in a flow diagram, an example of generating new compact data set 3126s, in accordance with some embodiments. Once the model is trained then, the trained neural engine model 3124 may be used with new descriptors (e.g., 3116, 3118, 3120 and 3122) to obtain new compact dataset 3126 that can be stored in compact dataset database 3128.

Figure 38:
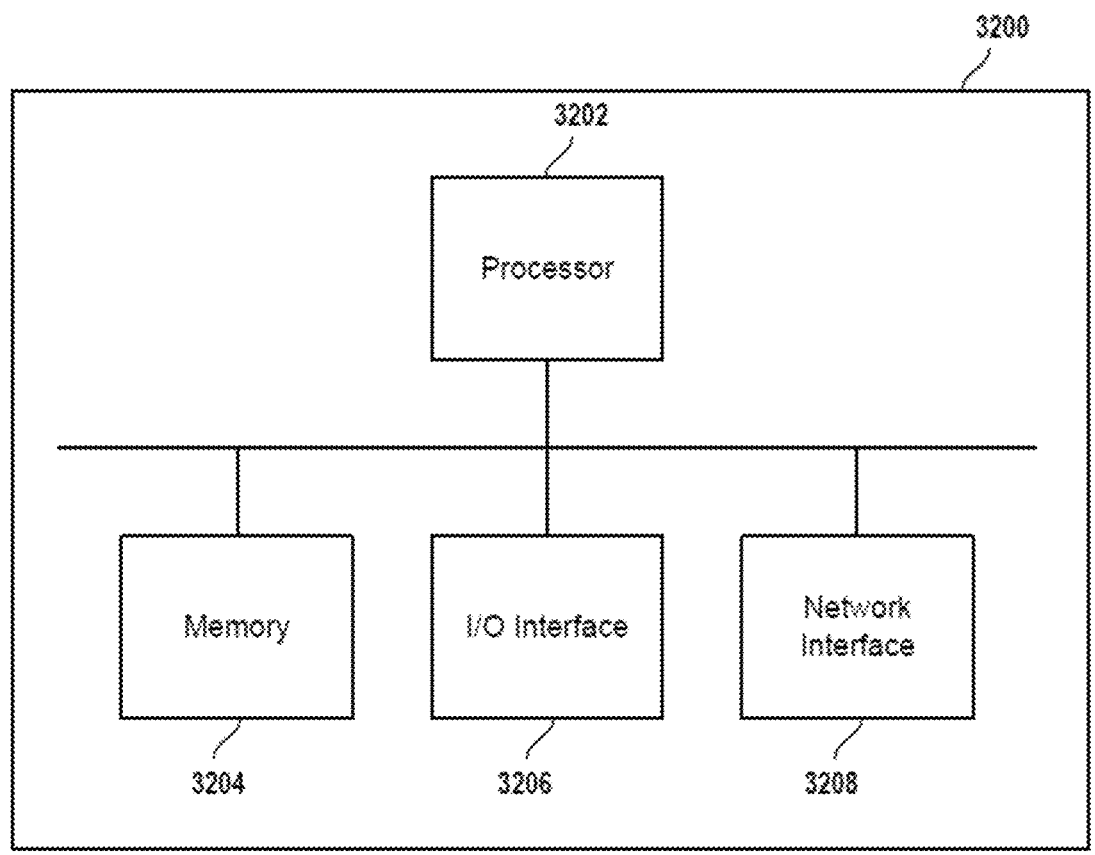
FIG. 38 is a schematic diagram of a computing device such as a server or other computer in a device.

FIG. 38 is a schematic diagram of a computing device 3200 such as a server or other computer in a device. As depicted, the computing device includes at least one processor 3202, memory 3204, at least one input/output (I/O) interface 3206, and at least one network interface 3208. Processor 3202 may be an Intel or AMD x86 or x64, PowerPC, ARM processor, or the like. Memory 3204 may include a suitable combination of computer memory that is located either internally or externally such as, for example, random-access memory (RAM), read-only memory (ROM), compact disc read-only memory (CDROM). Each I/O interface 3206 enables computing device 3200 to interconnect with one or more input devices, such as a keyboard, mouse, camera, touch screen and a microphone, or with one or more output devices such as a display screen and a speaker. Each network interface 3208 enables computing device 3200 to communicate with other components, to exchange data with other components, to access and connect to network resources, to serve applications, and perform other computing applications by connecting to a network (or multiple networks) capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. Wi-Fi, WiMAX), SS7 signaling network, fixed line, local area network, wide area network, and others.

Figure 39A:
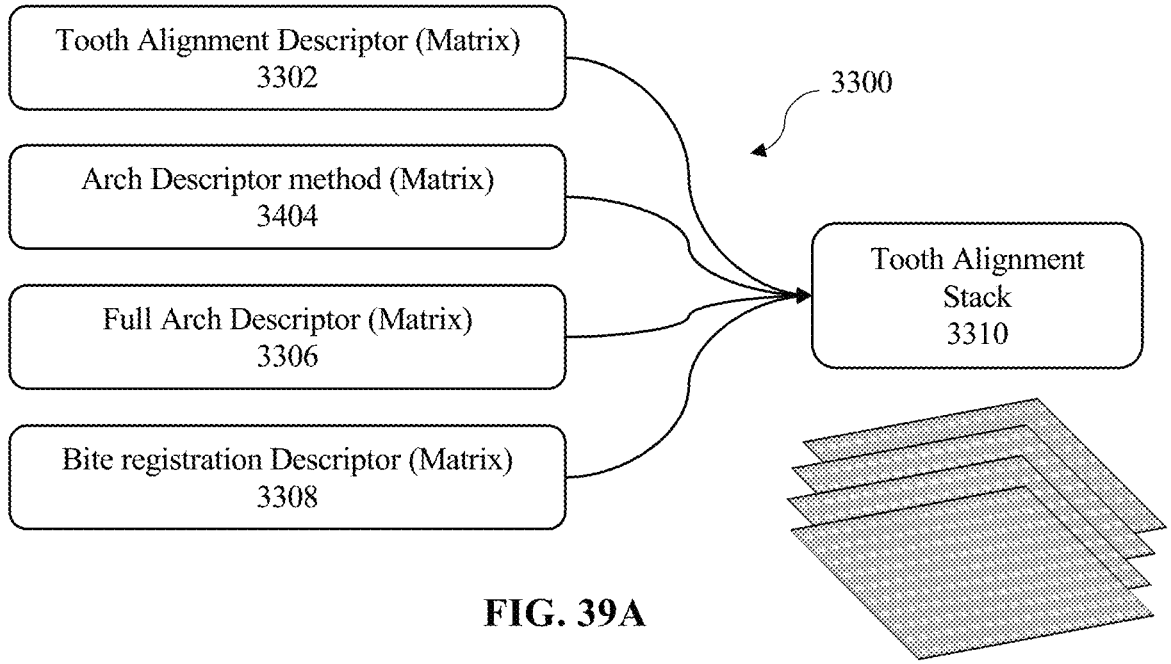
FIG. 39A illustrates a tooth alignment stack and its related descriptors in matrix format.
Figure 39B:
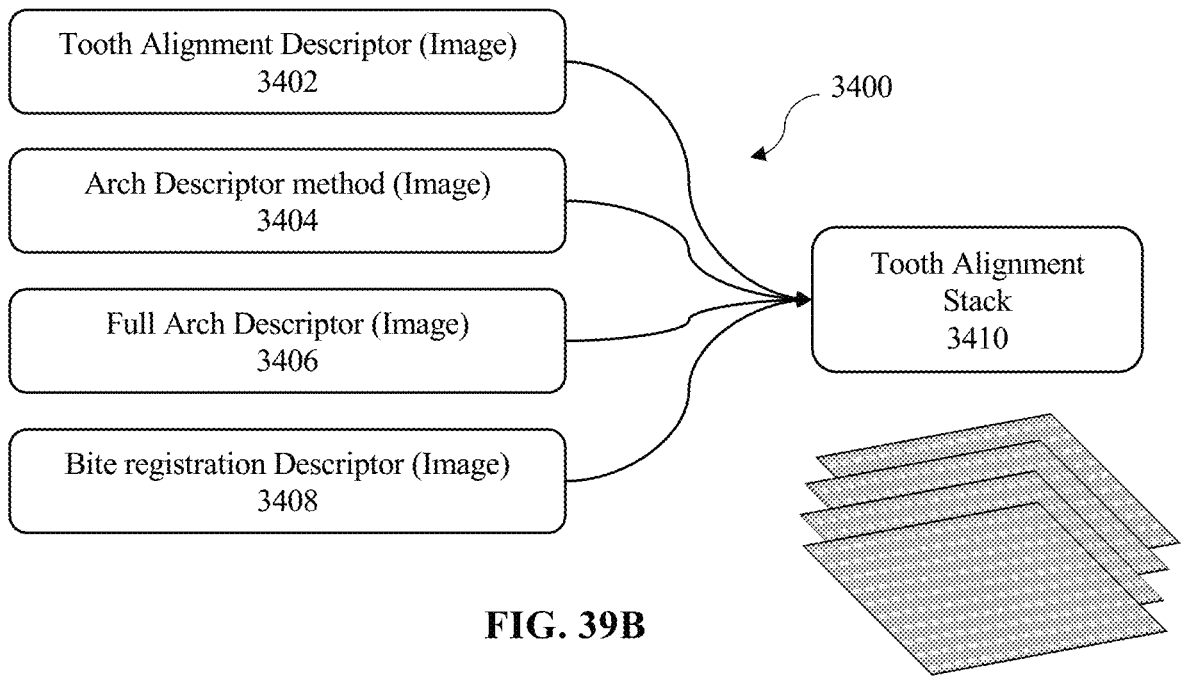
FIG. 39B illustrates a tooth alignment stack and related descriptors in image format.

FIG. 39A illustrates a tooth alignment stack and its concerned descriptors in matrix format in an orthodontic method. In an orthodontics application, a tooth alignment stack is utilized to automate complete tooth alignment treatment. FIG. 39A shows a tooth alignment stack 3300 which is made up of four different descriptors Tooth Alignment Descriptor 3302, Arch Descriptor method (Matrix output) 3304, Full Arch Descriptor (Matrix output) 3306, and Bite registration Descriptor (Matrix output) 3308 which are stacked on top of another. Similarly, FIG. 39B illustrates a tooth alignment stack and its concerned descriptors in image format where the same or similar stacking can be achieved with the same descriptor but with Image 3400 as an output. One can have any number of Tooth Alignment Stacks 3310 or 3410 for different types of dental anatomy, for example, lower or upper of any patient's bitewing, quadrant, full Dental Arch. FIG. 39B shows the Tooth Alignment stack 3400 which is made up of four different descriptors Tooth Alignment Descriptor (Image output) 3402, Arch Descriptor method (Image output) 3404, Full Arch Descriptor (Image output) 3406, and Bite registration Descriptor (Image output) 3408 which are stacked on top of another.

Figure 40:
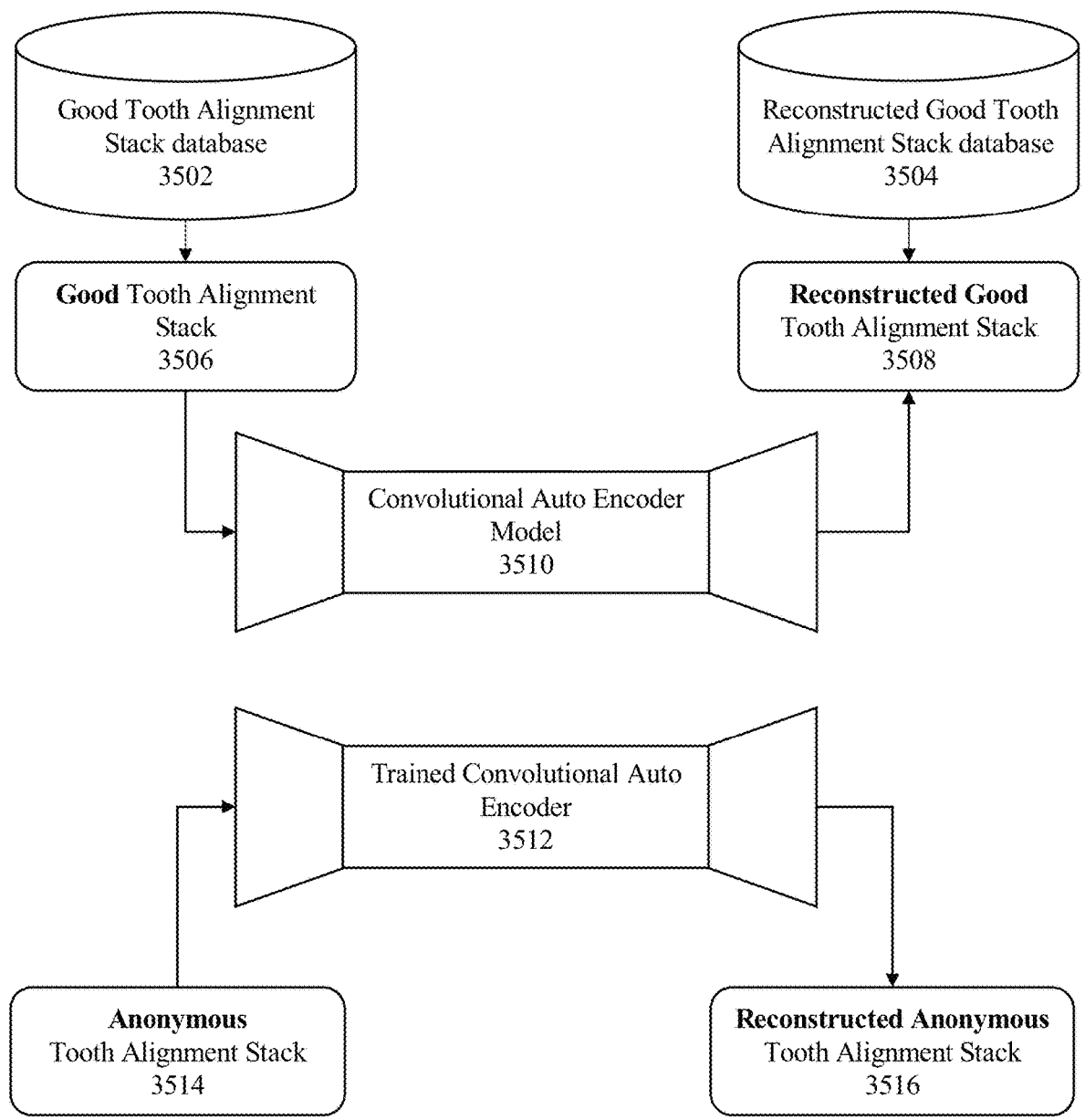
FIG. 40 is a schematic diagram of the training and use of a Convolutional Auto Encoder in a tooth alignment analysis.

FIG. 40 is a schematic diagram of how the convolution Auto Encoder functions. Given a set of bite pattern descriptor matrixes or tooth alignment stacks in an orthodontic application, the next task is to make a database of good tooth alignment stacks 3502. The term "good" means that the dental anatomy whose tooth alignment stacks are stored in the database is in healthy condition. The Good tooth alignment stack 3506 from the Good Tooth Alignment Stack database 3502 goes through Convolutional Auto Encoder 3510, and the Reconstructed Good Tooth Alignment Stack 3508 is generated. The Reconstructed Good Tooth Alignment Stack 3508 is then stored in the Reconstructed Good Tooth Alignment stack database 3504. Once the Convolutional Auto Encoder 3510 is trained, the Trained Convolutional Auto Encoder 3512 can be used to evaluate whether a particular dental stack is good or not. This is done by feeding an Anonymous Tooth Alignment Stack 3514 into the Trained Convolutional Auto Encoder 3512 to provide a Reconstructed Anonymous Tooth Alignment Stack 3516 which can be evaluated.

The computer-implemented method can use augmented intelligence with orthodontic data for the computer-aided design of orthodontic and prosthetic crowns and bridges, in addition to braces, brace fixtures, dental retainers, orthodontic aligners, and other dental and orthodontal implants and devices. Using alignment patterns in the computer aided design of these structures enables optimal realignment of crown, bridges, and other dental prosthetics. Additionally, using dental models and alignment patterns orthodontic aligners can be designed without help of braces and without physical impressions using putty. Further, positioning of teeth along the orthodontic treatment period can be followed and quantified easily and compared to previous images using imaging methods and image data processing methods as herein described by comparing scanned arches taken at different time during treatment. In this way orthodontic treatment can be easily tweaked or adjusted during the treatment period and orthodontic appliances can be quickly designed and redesigned based on up-to-date patient information. A step-by-step orthodontic treatment can also be provided to automatically print pre-designed aligner shells set with current image data, optionally in combination with other dental appliances and/or procedures. Additionally, the present method can also provide a treatment plan for braces, crowns, bridges, and other orthodontic appliances when aligner shells are not effective or require additional complementary alignment, and alignment patterns and protocols can be provided to dental professionals based on the augmented intelligence uncovered by the present models. The present method can also be used for alignment for improving bite registration. Further, orthodontic pattern recognition can detect defective alignment patterns, for example those requiring a corrective action, immediately after a digital impression is made, even if a dental scanner is used by a hygienist, a dental assistant, or a general practitioner. Orthodontic treatment progress can also be quantified automatically by comparing scanned arches taken at different time during treatment.

Figure 41:
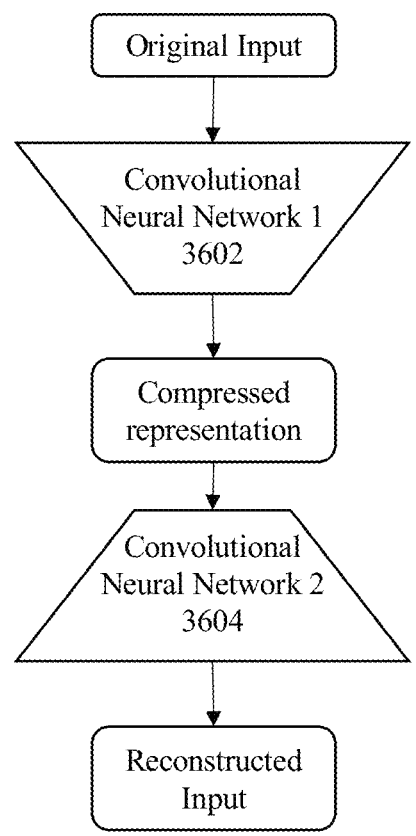
FIG. 41 is a schematic diagram of an example convolution auto encoder components and method in a tooth alignment analysis.

FIG. 41 is a schematic diagram of the convolution Auto Encoder components and shows the Convolutional Auto Encoder in more detail. The Convolutional Auto Encoder is a combination of two Convolutional Neural Networks (CNN) connected to one another, and the output of the second convolutional neural network gives the reconstructed output which is of lower quality and smaller size than the original input. This machine learning model can be used for automated treatment and tooth alignment analysis using dental descriptor matrix stacks. As shown, convolutional neural network 1 3602 takes the original input data. The convolutional neural network 1 has hidden layers which decrease in size as you go from the input layer to the output layer. This part of the model gives a compressed representation, meaning lower dimensional latent representation as the data is processed. Then the compressed output is used as input to another convolutional neural network 2 3604 which gives the reconstructed output of the original file which is of lower quality and smaller size than the original file. The second convolutional neural network has hidden layers that increase in size as you go from the input layer to the output layer and the last layer matches the input layer of the Convolutional Neural Network 1. In combination, the convolution auto-encoder can be used to compare both the original (Good Tooth Alignment Stack), which was an input to the Convolutional Autoencoder to the reconstructed output (Reconstructed Good Tooth Alignment Stack) and measure the reconstruction loss. Based on both database comparisons threshold loss is identified. Now the Convolutional Auto Encoder Model can be trained so that it can be used for treatment. Once the model is trained, the learning of the model is preferably frozen. In practice, an Anonymous Tooth Alignment stack is fed to the trained Convolutional Autoencoder and a Reconstructed Anonymous Tooth Alignment Stack is obtained. Both the original and reconstructed stacks are compared to measure the reconstruction loss and then compared with threshold value as described, and based on the value comparison a dental or orthodontic treatment can be suggested.

In a periodontic analysis a gum descriptor stack can be generated comprising a plurality of different types of descriptor matrixes describing the gum. A periodontic descriptor stack can include, for example, a gum line descriptor, arch descriptor, gum thickness descriptor, and bite registration descriptor. The periodontic descriptor stack can similarly be passed-through a convolutional auto encoders to regenerate the descriptor again and train the convolutional auto encoder. The trained convolutional auto encoder model can then be used for an anonymous periodontic descriptor stack to uncover periodontic and gum health and potential anomalies for prognosis of gum health.

Figure 42A:
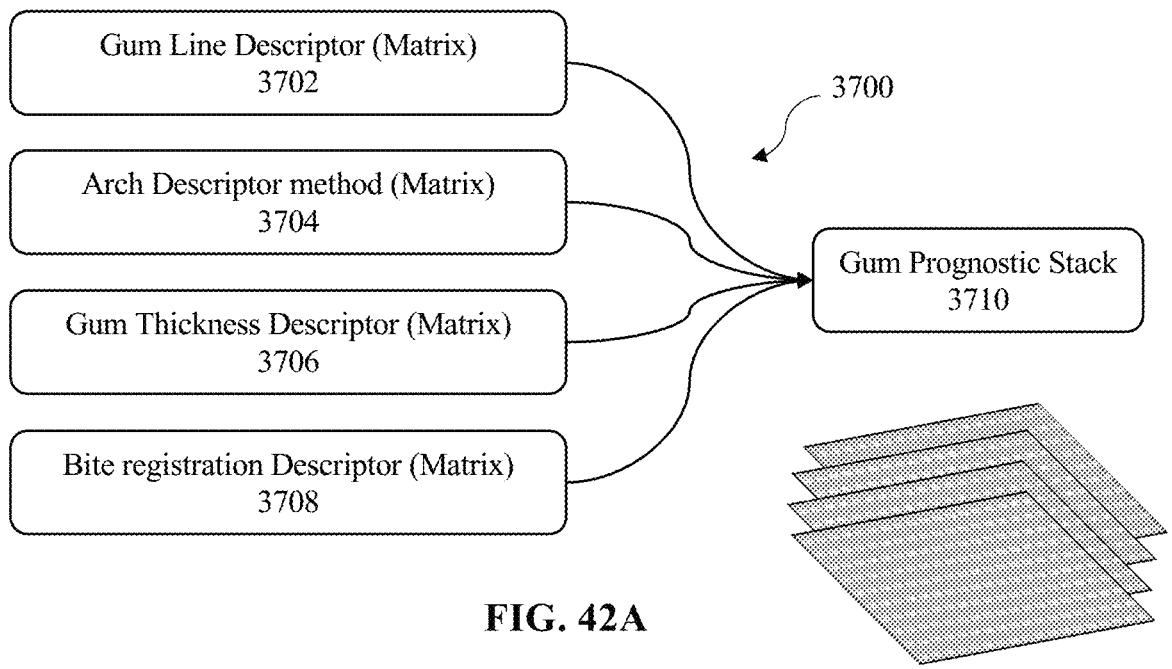
FIG. 42A illustrates a gum prognostic stack and related descriptors in matrix format.
Figure 42B:
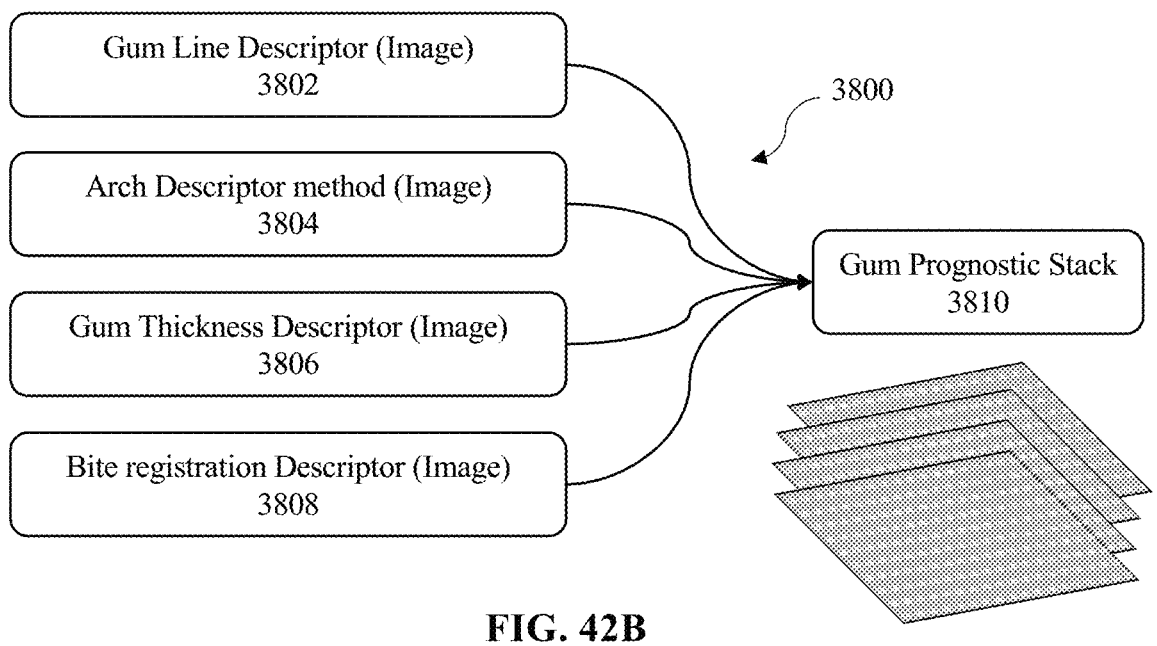
FIG. 42B illustrates a gum prognostic stack and related descriptors in image format.

FIG. 42A illustrates a gum prognostic stack and its concerned descriptors in matrix format, in accordance with some embodiments. One can have any number of Gum Prognostic Stacks 3710 or 3710 for different types of dental anatomy, for example, lower or upper of any patient's bitewing, quadrant, full Dental Arch. A Gum Prognostic stack is utilized to automate complete gum prognostic treatment. FIG. 42A shows the Gum Prognostic stack 3700 which is made up of four different descriptors Gum Line Descriptor (Matrix output) 3702, Arch Descriptor method (Matrix output) 3704, Gum Thickness Descriptor (Matrix output) 3706, and Bite registration Descriptor (Matrix output) 3708 which are stacked on top of another. FIG. 42B illustrates a gum prognostic stack and its concerned descriptors in image format, in accordance with some embodiments. Same stacking can be achieved with the same descriptor but with Image 3700 as an output of the above-mentioned descriptors.

Figure 43:
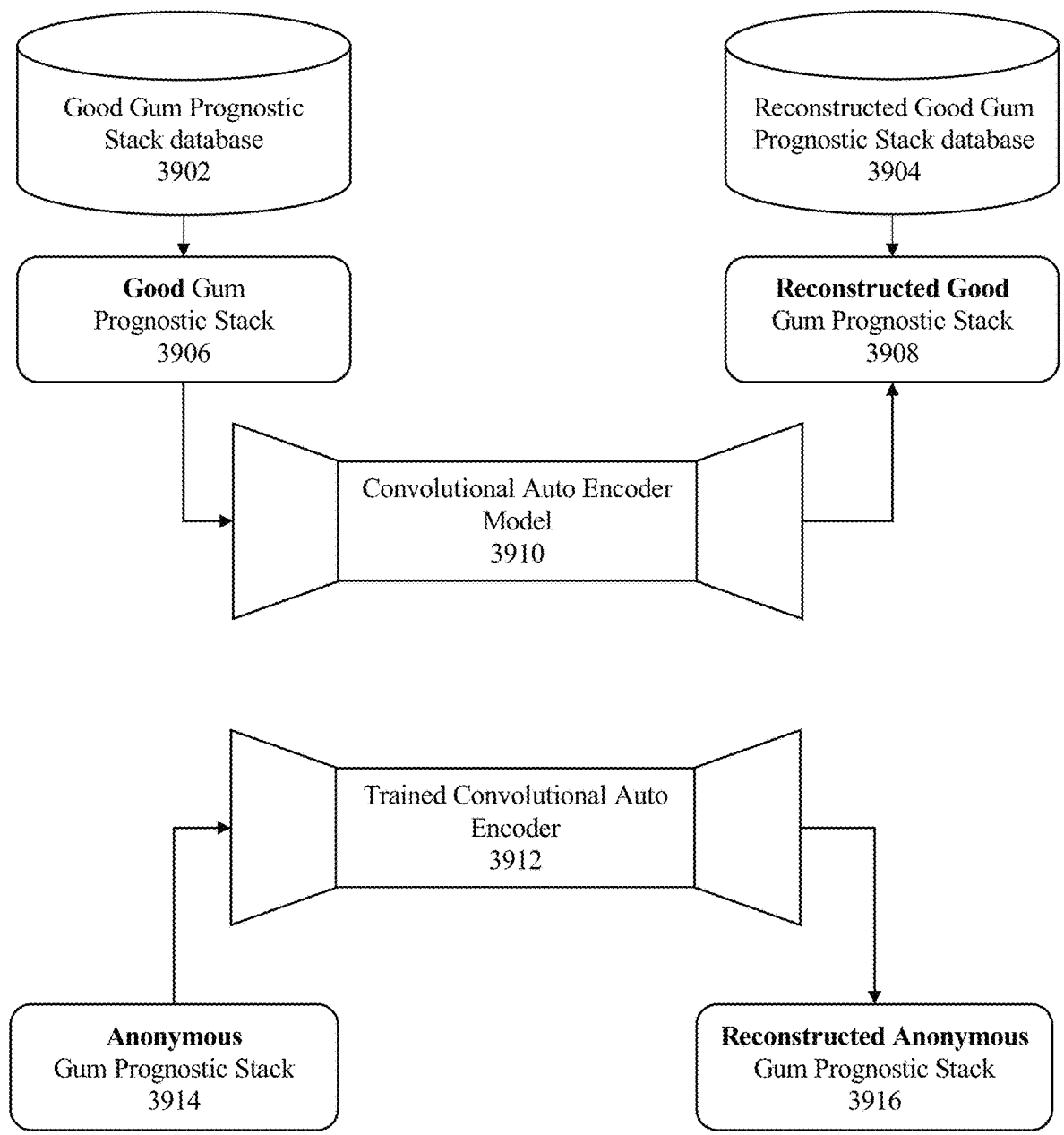
FIG. 43 is a schematic diagram of an example convolution auto encoder components and method in a gum prognostic analysis.

FIG. 43 is a schematic diagram of how the convolution Auto Encoder functions, in accordance with some embodiments. The first task is to make a database of good Gum Prognostic stacks 3902. The term "good" means that the dental anatomy whose Gum Prognostic stacks are stored in the database is in healthy condition, which serves as the training set. Now the set of Good Prognostic stacks 3906 will go through Convolutional Auto Encoder 3910, and each Reconstructed Good Gum Prognostic Stack 3908 is generated. The Reconstructed Good Gum Prognostic Stack 3908 is then stored in the Reconstructed Good Gum Prognostic database 3908. Similar to the structure of the combination of two Convolutional Neural Networks (CNN) as previously described for tooth alignment, a similar structure can be used for gum (periodontic) prognosis. In particular, two CNNs connected to one another can be used. The output of the second Convolutional Neural Network gives a reconstructed output which is a smaller dataset than the original input, and this reconstructed output can be used as a machine learning model for automated treatment. In this method for gum prognosis and treatment, Convolutional Neural Network 1 takes the original input data. The Convolutional Neural Network 1 has hidden layers which decrease in size as we go from the input layer to the output layer. The section of the model gives a compressed representation, meaning the lower dimensional latent representation and now, a compressed output is used as an input to another Convolutional Neural Network 2 in which allows the original file to be reconstructed and gives the reconstructed output of the original file. The output data, or reconstructed input, is a smaller dataset than the original file. The second Convolutional Neural Network has hidden layers that increase in size as you go from the input layer to the output layer and the last layer matches the input layer of the Convolutional Neural Network 1. From this output a comparison of both the original (Good Gum Prognostic Stack), which was an input to the Convolutional Autoencoder to the reconstructed output (Reconstructed Good Gum Prognostic Stack) and the reconstruction loss can be measured. Based on both databases the comparison threshold loss is identified. Now the model has been trained allowing it to be used for treatment. Once the model is trained the learning can be frozen. An Anonymous Gum Prognostic stack can then be fed to the trained Convolutional Autoencoder and a Reconstructed Anonymous Gum Prognostic Stack is obtained. Both the original and reconstructed stacks are compared to measure the reconstruction loss and then it is compared with threshold value as describe and based on the value comparison treatment can be suggested.

The present method can be used in crown and bridge margin modeling, also referred to as gum line, and can be incorporated into, for example, augmented reality guided preparation platforms for periodontic surgery. This can be effected by displaying the gum line and dental image data in a surgery graphical user interface (GUI) by matching patient gum line patterns predicted to result in an improved and healthier gum line. Using reconstructed dental images produced by the present method can also assist in rapid diagnosis of many common gum diseases. In particular a 3D mouth scan is uploaded from an oral scanner as a mesh file and can be compared to previous dental scans of the same patient, dental scans of other patients, and dental patterns indicative of gum disease. One advantage of the present method is that once set up, a non-specialist such as a dental assistant or hygienist can be trained to obtain dental and oral scans sufficient to arrive at accurate diagnoses. Once a diagnosis is reached, treatment progress can be rapidly quantified after a mouth scan is uploaded from an oral scanner to the system. Disease progression and quantification thereof can also be done over time to gauge the effectiveness of treatment. Specifically, numerical values of, for example, gum thickness, position (such as relative to the crown), and line profile of each tooth can be provided in numerical format a few seconds after the mouth scan is uploaded from an oral scanner. The oral scan can take anywhere from 30 seconds to a few minutes to obtain quality images sufficient to provide accurate periodontic diagnosis and prognosis.

The foregoing discussion provides example embodiments of the inventive subject matter. Although each embodiment represents a single combination of inventive elements, the inventive subject matter is considered to include all possible combinations of the disclosed elements. Thus, if one embodiment comprises elements A, B, and C, and a second embodiment comprises elements B and D, then the inventive subject matter is also considered to include other remaining combinations of A, B, C, or D, even if not explicitly disclosed. The embodiments of the devices, systems and methods described herein may be implemented in a combination of both hardware and software. These embodiments may be implemented on programmable computers, each computer including at least one processor, a data storage system (including volatile memory or non-volatile memory or other data storage elements or a combination thereof), and at least one communication interface. Program code is applied to input data to perform the functions described herein and to generate output information. The output information is applied to one or more output devices. In some embodiments, the communication interface may be a network communication interface. In embodiments in which elements may be combined, the communication interface may be a software communication interface, such as those for inter-process communication. In still other embodiments, there may be a combination of communication interfaces implemented as hardware, software, and combination thereof.

Numerous references are made regarding servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions.

The technical solution of embodiments may be in the form of a software product. The software product may be stored in a non-volatile or non-transitory storage medium, which can be a compact disk read-only memory (CD-ROM), a USB flash disk, or a removable hard disk. The software product includes a number of instructions that enable a computer device (personal computer, server, or network device) to execute the methods provided by the embodiments. The embodiments described herein are implemented by physical computer hardware, including computing devices, servers, receivers, transmitters, processors, memory, displays, and networks. The embodiments described herein provide useful physical machines and particularly configured computer hardware arrangements.

As can be understood, the examples described above and illustrated are intended to be exemplary only. All publications, patents and patent applications mentioned in this specification are indicative of the level of skill of those skilled in the art to which this invention pertains and are herein incorporated by reference. The reference to any prior art in this specification is not, and should not be taken as, an acknowledgement or any form of suggestion that such prior art forms part of the common general knowledge.

Although the embodiments have been described in detail, it should be understood that various changes, substitutions and alterations can be made herein. Moreover, the scope of the present application is not intended to be limited to the particular embodiments of the process, machine, manufacture, composition of matter, means, methods and steps described in the specification. Such variations are not to be regarded as a departure from the scope of the invention, and all such modifications as would be obvious to one skilled in the art are intended to be included within the scope of the following claims.

What is claimed is:

1. A computer-implemented method for dental object description comprising:
   receiving, by a processor, a three dimensional (3D) mesh file representation of a dental object comprising a plurality of related surfaces;
   extending a plurality of indexing rays from a reference locus through the 3D mesh file such that the indexing ray intersects with the plurality of related surfaces at a surface boundary;
   creating a 2D descriptor matrix for each surface of the plurality of related surfaces by:
      for each of the plurality of indexing rays, measuring a length from the reference locus to the surface boundary to generate a plurality of indexing ray lengths; and
      storing the plurality of indexing ray lengths in a 2D matrix to create the 2D descriptor matrix of the surface; and
   storing the 2D descriptor matrix for each surface of the plurality of related surfaces as a matrix descriptor stack,
   wherein the cell of each row and column in each 2D descriptor matrix of the plurality of related surfaces corresponds with the same indexing ray such that the 2D descriptor matrix for each of the plurality of related surfaces is stacked in space.

2. The method of claim 1, further comprising slicing the 3D mesh file into an plurality of two dimensional (2D) cross-sectional slicing planes, wherein the plurality of indexing rays are coplanar with a cross-sectional slicing plane.

3. The method of claim 2, wherein the slicing planes are parallel to the reference locus or extend radially from the reference locus.

4. The method of claim 1, wherein the reference locus is a common centroid or a common z-axis.

5. The method of claim 1, further comprising training a convolutional autoencoder model using a convolutional neural network to identify matching 2D descriptor matrixes in a descriptor database.

6. The method of claim 1, further comprising assigning a dental object type to each 2D descriptor matrix and matching the 2D descriptor matrix to a matched 2D descriptor matrix describing a matching dental object having the same dental object type.

7. The method of claim 1, wherein the related surfaces are one or more of gumline, gum surface, neighbouring tooth surface, occlusal tooth surface on an opposite jaw to the dental object, arch surface, inside prosthetic surface, post surface, outside prosthetic surface, and appliance surface.

8. The method of claim 1, wherein the reference locus is a common centroid or a reference axis.

9. The method of claim 1, wherein the dental object comprises one or more of a tooth, a plurality of teeth, a bitewing, a gumline, and a dental arch.

10. The method of claim 1, further comprising applying a visualization scheme to visualize each 2D descriptor matrix.

11. The method of claim 1, further comprising using the matrix descriptor stack in dental tracking, orthodontic tracking, periodontic tracking, oral diagnostics, dental prosthetic design, orthodontic device design, dental implant design, or surgery planning.

12. The method of claim 1, wherein the dental object is a group of adjacent teeth described by a group descriptor matrix, and wherein the matrix descriptor stack comprises a tooth submatrix for each tooth in the group of adjacent teeth, each submatrix comprising the same dimensions as the group descriptor matrix and zero or null entries for the other teeth in the group of teeth.

13. The method of claim 12, further comprising creating a visualization map for the overall group descriptor submatrix and for each tooth submatrix.

14. The method of claim 1, wherein the dental object comprises an upper subset of adjacent teeth and a corresponding lower subset of adjacent teeth, the method further comprising:
- determining an absolute difference between an upper tooth and a corresponding point on a lower teeth;
- storing the plurality of absolute differences in a bite pattern descriptor matrix.

15. The method of claim 14, further comprising rendering the bite registration descriptor matrix in a visualization map such that each entry in the bite registration descriptor matrix is replaced with a corresponding shade intensity.

16. A method of measuring dental change comprising:
- obtaining a first mesh image of a dental object and a second mesh image of the dental object after a time lapse;
- aligning the first mesh image and the second mesh image and assigning a common reference locus;
- for each of the first mesh image and the second mesh image, extending a plurality of indexing rays from the reference locus to a surface boundary;
- creating a 2D descriptor matrix for each of the first mesh image and the second mesh image by:
  - for each of the plurality of indexing rays, measuring a length from the reference locus to the surface boundary to generate a plurality of indexing ray lengths; and
  - storing the plurality of indexing ray lengths in a 2D matrix to create the 2D descriptor matrix; and
- storing the 2D descriptor matrix for the dental object and the dental object after a time lapse as a matrix descriptor stack, wherein the cell of each row and column in each 2D descriptor matrix corresponds with the same indexing ray such that the 2D descriptor matrixes are stacked in space; and
- comparing the 2D descriptor matrixes to determine deviation after the time lapse.

17. The method of claim 16, wherein the dental change is one or more of orthodontic shift, periodontal change, and tooth degradation.

18. A method of measuring dental occlusion comprising:
- obtaining an occlusal three-dimensional (3D) mesh image comprising a top bitewing and bottom bitewing in occlusal alignment, the mesh image comprising a top occlusal surface and a bottom occlusal surface;
- extending a plurality of indexing rays from a reference locus through the mesh such that each of the plurality of indexing rays intersects with the top bitewing and the bottom bitewing;
- creating a bite pattern descriptor matrix by:
  - for each of the plurality of indexing rays, measuring a length from the reference locus to a surface of the bottom bitewing and a surface of the top bitewing to generate a plurality of indexing ray lengths; and
  - storing the plurality of indexing ray lengths as a measurement of absolute distance between the surface of the bottom bitewing and the surface of the top bitewing to generate the bite pattern descriptor matrix of the occlusal surface.

19. The method of claim 18, further comprising applying a threshold to the bite pattern descriptor matrix to identify loci below a certain threshold indicative of locations of good occlusal interaction between the upper bitewing and the lower bitewing.

20. The method of claim 18, wherein the occlusal three-dimensional (3D) mesh image is obtained using occlusal radiography or computed tomography.

21. The method of claim 20, further comprising matching the bite pattern descriptor matrix to similar the bite pattern descriptor matrixes in a descriptor database using a trained convolutional neural network to evaluate the degree of dental occlusion.

* * * * *